United States Patent [19]
Hood et al.

[11] Patent Number: 5,318,570
[45] Date of Patent: Jun. 7, 1994

[54] ULTRASONIC TOOL

[75] Inventors: Larry L. Hood, Laguna Hills; James T. Caillouette, Newport Beach; Robert C. Klapper, Los Angeles; Gregg Hughes, El Toro; Ted Carlson, Mission Viejo, all of Calif.; John Berkman, Grants Pass, Oreg.

[73] Assignee: Advanced Osseous Technologies, Inc., Aliso Viejo, Calif.

[21] Appl. No.: 713,959

[22] Filed: Jun. 11, 1991

Related U.S. Application Data

[63] Continuation-in-part of Ser. No. 665,418, Mar. 5, 1991, which is a continuation-in-part of Ser. No. 304,820, Jan. 31, 1989, Pat. No. 5,019,083.

[51] Int. Cl.$^5$ .................................................. A61F 2/46
[52] U.S. Cl. ................................... 606/99; 606/169; 601/2
[58] Field of Search ................... 606/169, 82, 99, 92, 606/102, 104, 176, 177, 178, 179, 84; 128/24 A; 623/16, 23

[56] References Cited

U.S. PATENT DOCUMENTS

| | | |
|---|---|---|
| 33,530 | 10/1861 | Leisen . |
| 165,403 | 7/1875 | Blatt . |
| 446,078 | 2/1891 | Rouse . |
| 804,831 | 11/1905 | Cunnius . |
| 1,096,763 | 5/1914 | Smith . |
| 1,390,904 | 9/1921 | Hazelton . |
| 1,451,970 | 4/1923 | Taylor . |
| 1,483,164 | 2/1924 | Driggs . |
| 1,967,145 | 7/1934 | Fisher . |
| 2,138,245 | 11/1938 | Smith . |
| 2,257,327 | 4/1941 | Bradford . |
| 2,517,364 | 8/1950 | Torresen . |
| 2,714,890 | 8/1955 | Vang . |
| 2,784,637 | 3/1957 | Smisko . |
| 2,828,662 | 4/1958 | Antal . |
| 2,840,404 | 6/1958 | Weber, Jr. . |
| 3,006,003 | 10/1961 | Johnson, Jr. . |
| 3,076,904 | 2/1963 | Kleesattel et al. . |
| 3,086,288 | 4/1963 | Balamuth et al. . |
| 3,101,210 | 8/1963 | Johnson . |
| 3,184,353 | 5/1965 | Balamuth et al. . |
| 3,346,279 | 10/1967 | Stachiw et al. . |
| 3,401,446 | 9/1968 | Obeda et al. . |
| 3,407,454 | 10/1968 | Myatt . |
| 3,526,219 | 9/1970 | Balamuth . |
| 3,589,363 | 6/1971 | Banko et al. . |
| 3,683,736 | 8/1972 | Loose . |
| 3,693,613 | 9/1972 | Kelman . |

(List continued on next page.)

FOREIGN PATENT DOCUMENTS

| | | |
|---|---|---|
| 1014454 | 7/1977 | Canada . |
| 121491 | 3/1983 | European Pat. Off. . |
| 133393 | 8/1983 | European Pat. Off. . |
| 243298 | 4/1986 | European Pat. Off. . |

(List continued on next page.)

OTHER PUBLICATIONS

"Theory and Analysis of Sectional Concentrators" by L. G. Merkulov and A. V. Kharitonov, Apr. 18, 1958.

(List continued on next page.)

*Primary Examiner*—Robert A. Hafer
*Assistant Examiner*—David J. Kenealy
*Attorney, Agent, or Firm*—Knobbe, Martens, Olson & Bear

[57] ABSTRACT

Disclosed is a mechanical junction for facilitating the rapid attachment and removal of ultrasonic surgical components for the transfer of ultrasonic energy across the junction from an ultrasonic transducer to an ultrasonically activated tool bit. The junction achieves a high, evenly distributed compressive force to optimize propagation of the ultrasonic energy from the transducer to a tool bit, while maintaining a relatively small outside diameter of the ultrasonic tool. Also disclosed are a plurality of ultrasonic energy activated tool tips for introducing and removing an orthopedic prosthesis.

31 Claims, 45 Drawing Sheets

U.S. PATENT DOCUMENTS

| | | |
|---|---|---|
| 3,710,641 | 1/1973 | Anderson . |
| 3,809,977 | 5/1974 | Balamuth et al. . |
| 3,823,717 | 7/1974 | Pohlman et al. . |
| 3,862,630 | 1/1975 | Balamuth . |
| 3,889,166 | 6/1975 | Scurlock . |
| 3,902,495 | 9/1975 | Weiss et al. . |
| 3,990,452 | 11/1976 | Murry et al. . |
| 4,041,947 | 8/1977 | Weiss et al. . |
| 4,056,761 | 11/1977 | Jacoby et al. . |
| 4,063,557 | 12/1977 | Wuchinich et al. . |
| 4,184,510 | 1/1980 | Murry et al. . |
| 4,188,952 | 2/1980 | Loschilov et al. . |
| 4,248,232 | 2/1981 | Engelbrecht et al. . |
| 4,260,180 | 7/1981 | Halushka . |
| 4,277,710 | 7/1981 | Harwood et al. . |
| 4,298,074 | 11/1981 | Mattchen . |
| 4,418,583 | 12/1983 | Taig . |
| 4,425,115 | 1/1984 | Wuchinich . |
| 4,600,343 | 7/1986 | Frerejacques . |
| 4,636,219 | 1/1987 | Pratt et al. . |
| 4,679,959 | 7/1987 | Cavallaro . |
| 4,686,971 | 8/1987 | Harris et al. . |
| 4,705,038 | 11/1987 | Sjostrom et al. . |
| 4,705,500 | 11/1987 | Reimels et al. . |
| 4,750,488 | 6/1988 | Wuchinich et al. . |
| 4,768,496 | 9/1988 | Kreizman et al. . |
| 4,778,469 | 10/1988 | Lin et al. . |
| 4,781,507 | 11/1988 | Duenas . |
| 4,828,566 | 5/1989 | Griss . |
| 4,832,683 | 5/1989 | Idemoto et al. . |
| 4,834,081 | 5/1989 | Van Zile . |
| 4,846,161 | 7/1989 | Roger . |
| 4,850,755 | 7/1989 | Spencer et al. . |
| 5,007,917 | 4/1991 | Evans ............ 604/22 |
| 5,019,083 | 5/1991 | Klapper et al. . |
| 0424231 | 4/1991 | European Pat. Off. . |
| 2741107 | 9/1977 | Fed. Rep. of Germany . |
| 3131496 | 8/1981 | Fed. Rep. of Germany ....... 606/79 |
| 2083148 | 12/1971 | France . |
| 2508306 | 12/1982 | France . |
| 2614524 | 4/1987 | France . |
| 8802250 | 4/1988 | PCT Int'l Appl. . |
| 9004362 | 5/1990 | PCT Int'l Appl. . |
| 9111965 | 8/1991 | PCT Int'l Appl. . |
| 9202658 | 2/1992 | PCT Int'l Appl. . |
| 659798 | 3/1977 | U.S.S.R. . |
| 1128943 | 4/1982 | U.S.S.R. ............ 606/169 |
| 929088 | 5/1982 | U.S.S.R. . |
| 1229467 | 8/1984 | U.S.S.R. . |
| 692041 | 5/1953 | United Kingdom . |
| 1371335 | 10/1974 | United Kingdom . |
| 2140345 | 11/1984 | United Kingdom . |

"Mechanical Transformers for Producing Very Large Motion" by E. A. Neppiras, Acustica, vol. 13, Mar. 26, 1963.

"Complete Replacement Arthroplasty of the Hip by the Ring Prosthesis", The Journal of Bone and Joint Surgery, P. A. Ring, pp. 720–731 (British) vol. 50B, No. 4, Nov. 1968.

"Ultrasonic Cataract Extraction With Acoustic Horn" by Douglas McG. Clarkson and Calbert I. Phillips, Transactions of the Ophthalmological Society of the United Kingdom (1975) 95,477.

"Femoral Fractures in Conjunction With Total Hip Replacement" by Richard D. Scott et al., The Journal of Bone and Joint Surgery, vol. 57-A, No. 4, Jun. 1975.

"A Sonic Tool for Spinal Fusion" by Edmund B. Weis, Jr., M.D., Orthopedic Clinics of North America, vol. 8, No. 1, Jan. 1977.

Orthopedic Catalog-Richards Manufacturing Co., Inc., pp. 10, 14 and 20, 1981.

"A New Technique for Removal of Broken Femoral Stems in Total Hip Replacement" by William H. Harris, et al., The Journal of Bone and Joint Surgery, vol. 63-A, No. 5, Jun. 1981.

"Piezoelectric Ceramics: Characteristics and Applications" by Don Berlincourt, Acoustical Society of America, vol. 70, No. 6, Dec. 1981.

"A Model System to Demonstrate the Role of Cavitational Activity in Ultrasonic Scaling" by A. D. Walmsky; W. R. E. Laird and A. R. Williams, J Dent Res 63(9): 1162–1165, Sep. 1984.

Biological Fixation of the Porocoat AML® Hip-Manual for Pre–Operative Planning and Recommended Surgical Technique (1984) by Charles A. Engh, M.D. and J. Dennis Bobyn, Ph.D.

"Posterior Lumbar Interbody Fusion Technique: Complications and Pitfalls" by Paul M. Lin, M.D., Clinical Orthopaedics and Related Research, No. 193, Mar. 1985.

"The Stepped Horn" by John F. Belford—Clevite Electronic Components Division of Clevite Corporation, Dec. 12, 1985.

Technical Support Package on "Quick–Connect Heavy-Duty Fastener", NASA Tech Brief, vol. 10, No. 2, Item #34, Mar./Apr. 1986.

(List continued on next page.)

OTHER PUBLICATIONS

"Atraumatic Removal of a Well-Fixed Porous Ingrowth Hip Prostehesis" by Shearwood J. McClelland, et al., Orthopaedic Review, vol. XV, No. 6, Jun. 1986.

"The Window Technique for the Removal of Broken Femoral Stems in Total Hip Replacement" by John R. Moreland, et al., Clinical Orthopaedics and Related Research, No. 212, Nov. 1986.

"Development of a Bone-Fixation Prosthetic Attachment" by Lester J. Owens, NASA Kennedy Space Center, pp. 281, 283, 285, 287, 289, 291 and 293.

Technical Support Package for Tech Brief Lar-12232, "Quick-Connect Threaded Attachment Joint", Langley Research Center, NASA.

"Work-in-Progress #1: The Lithotriptor and Its Potential Use in the Revision of Total Hip Arthroplasty" by Robert R. Karpman, et al., Orthopaedic Review, vol. XVI, No. 1, Jan. 1987.

"Controlled Perforation: A Safe Method of Cement Removal from the Femoral Canal" by Sam V. Sydney, et al., Surgical Rounds for Orthopaedics, pp. 17-19, Jan. 1989.

"Proximal Fermoral Osteotomy in Difficult Revision Hip Surgery: How to Revise the Unrevisable" by Hugh H. Cameron, Ph.D., Contemporary Orthopaedics, May 1989, vol. 18, No. 5.

"Symposium: Advanced Biomaterials-The Future of Orthopaedics" by John P. Collier, D.E.; Charles A. Engh, M.D.; Jack Lemons, Ph.D., Contemporary Orthopaedics, Aug. 1989, vol. 19, No. 2.

"Femoral Fracture During Non—Cemented Total Hip Arthroplasty", John A. Schwartz, Jr., et al., The Journal of Bone and Joint Surgery, Incorporated, pp. 1135-1142, Sep. 1989, vol. 71-A, No. 8.

"Effect of Press-Fit Femoral Stems on Strains in the Femur: A Photoelastic Coating Study", X. M. Zhou et al., The Journal of Arthroplasty, Mar. 1990, vol. 5, No. 1A.

"The Use of Ultrasonic Tools In Revision Arthroplasty Procedures", Contemporary Orthopaedics by Robert C. Klapper, M.D. and James T. Caillouette, M.D., Mar. 1990, vol. 20, No. 3.

Piezoceramics Applications Data (Undated), pp. 3-10.

"Piezoelectric Displacement Generators—Status and Low Frequencies" by D. Berlincourt, Channel Industries, Inc. (Undated).

*Fracture Appliances* by DePuy, Inc., 1964.

Photographs 1-3 illustrating an ultrasonic aspiration surgical tool used in neural surgery, designed by Dr. David Wuchinich and disclosed in 1967.

Photographs 4-15 illustrating three ultrasonic surgical tools manufactured by Quinton and distributed by Howmedica, Inc. in 1985.

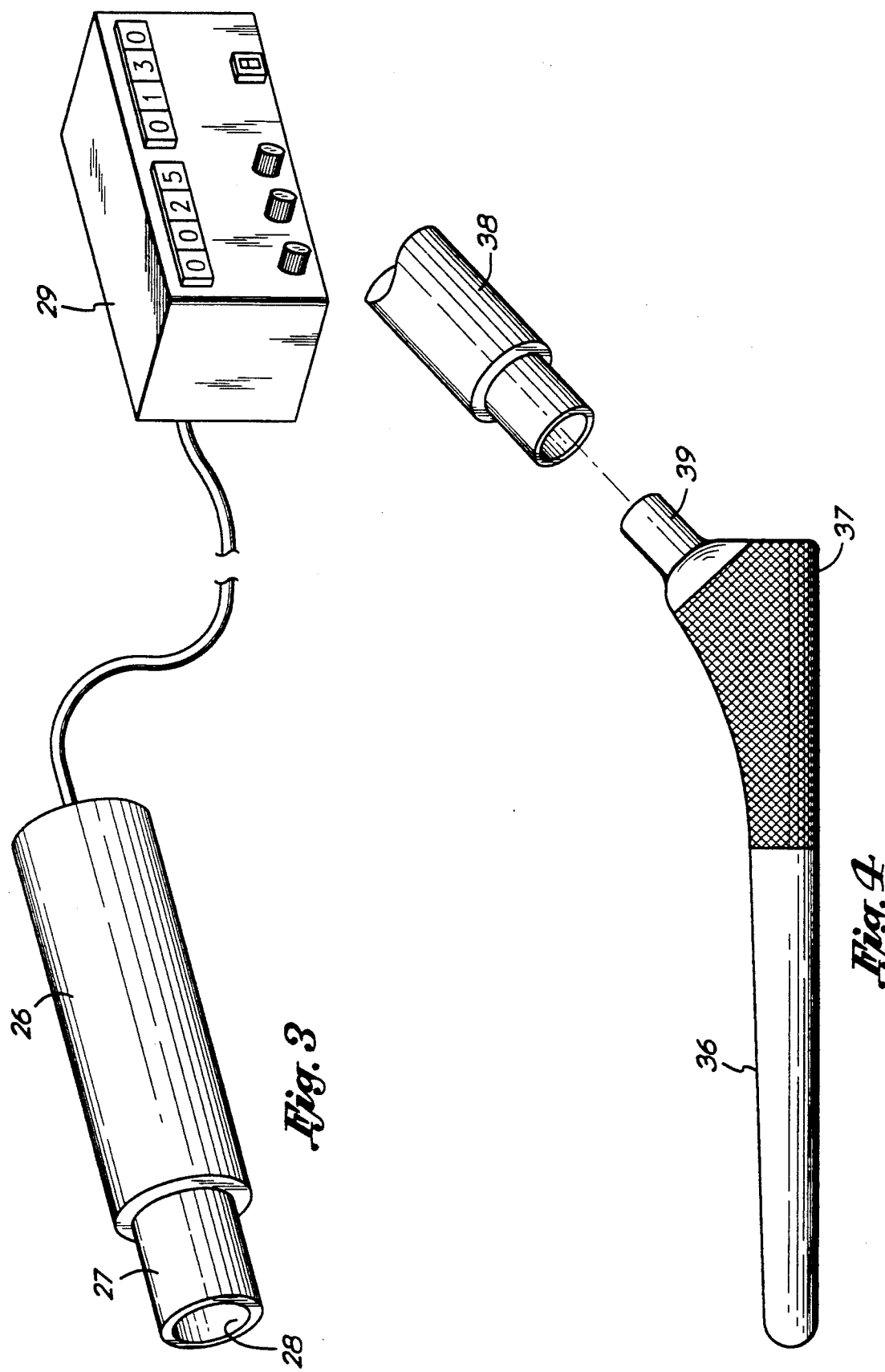

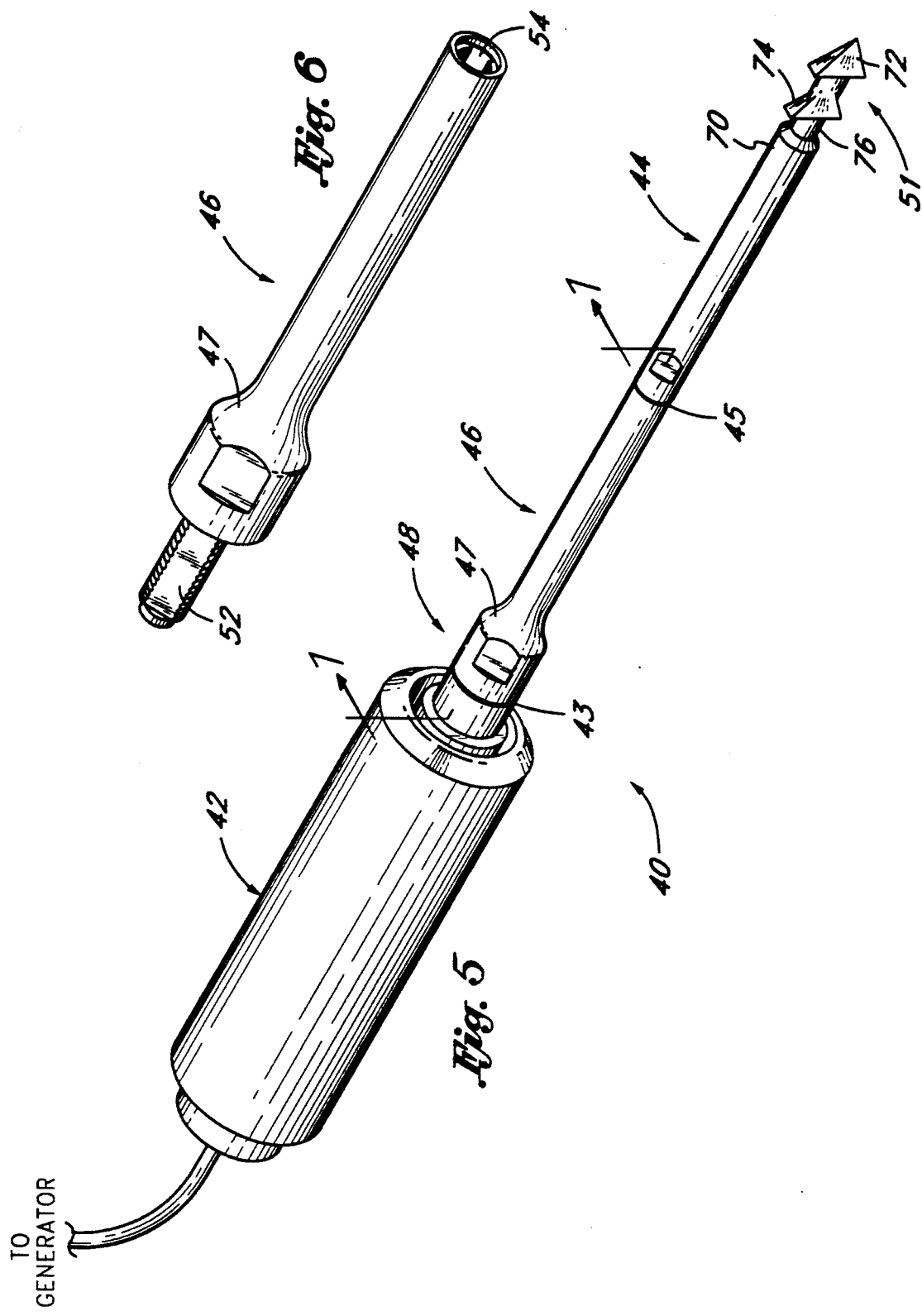

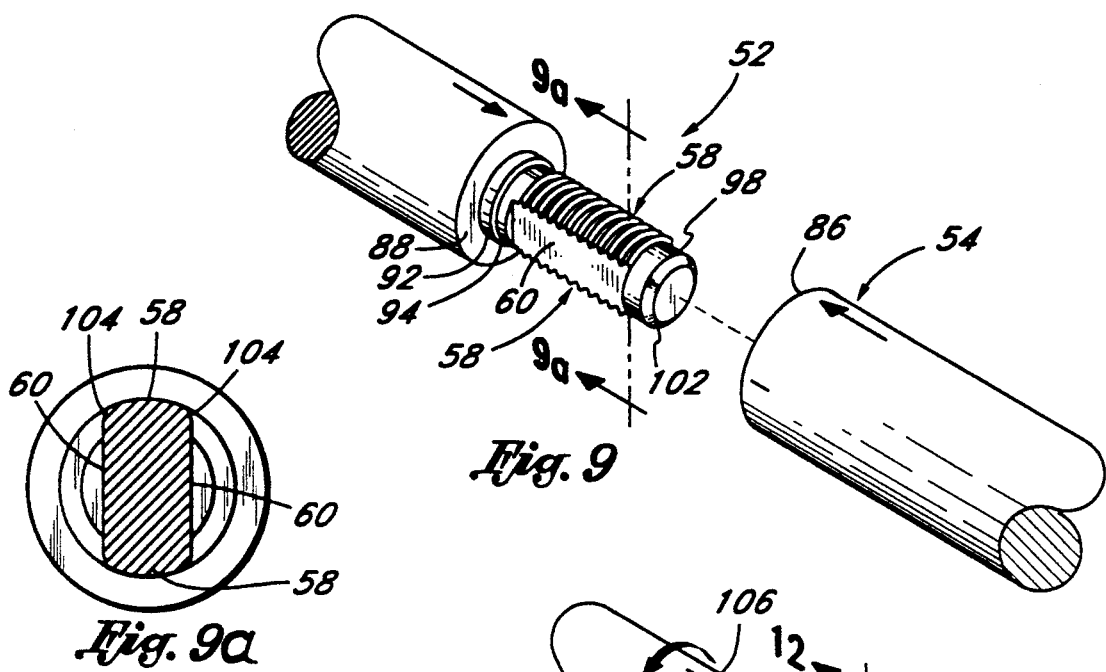
Fig. 9
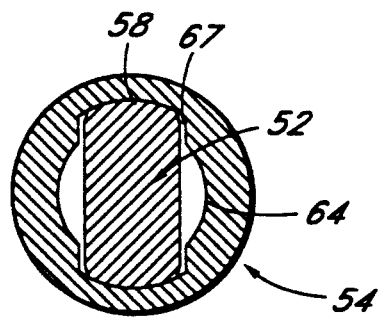
Fig. 9a
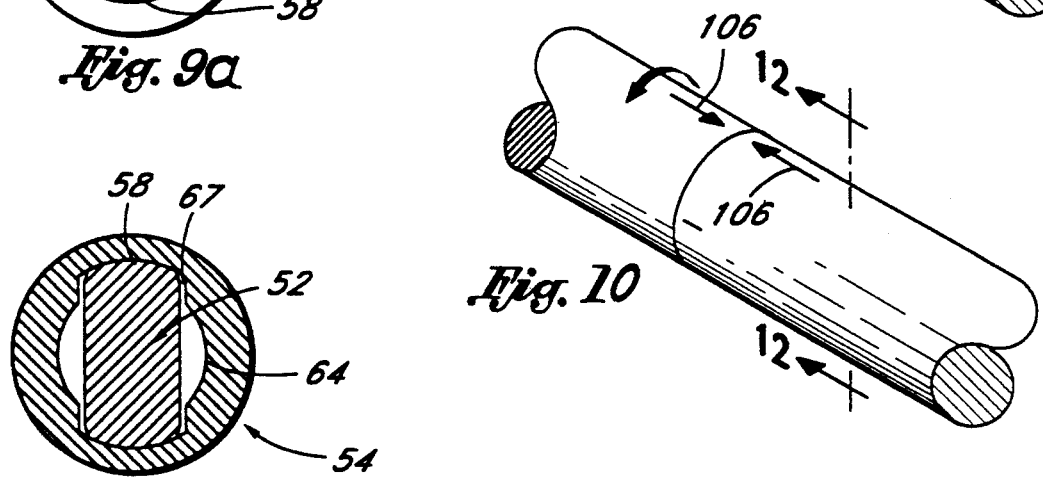
Fig. 10
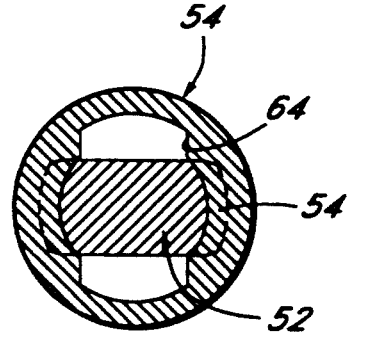
Fig. 12
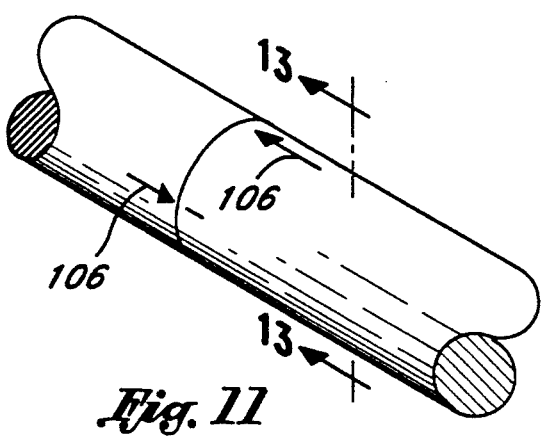
Fig. 13
Fig. 11

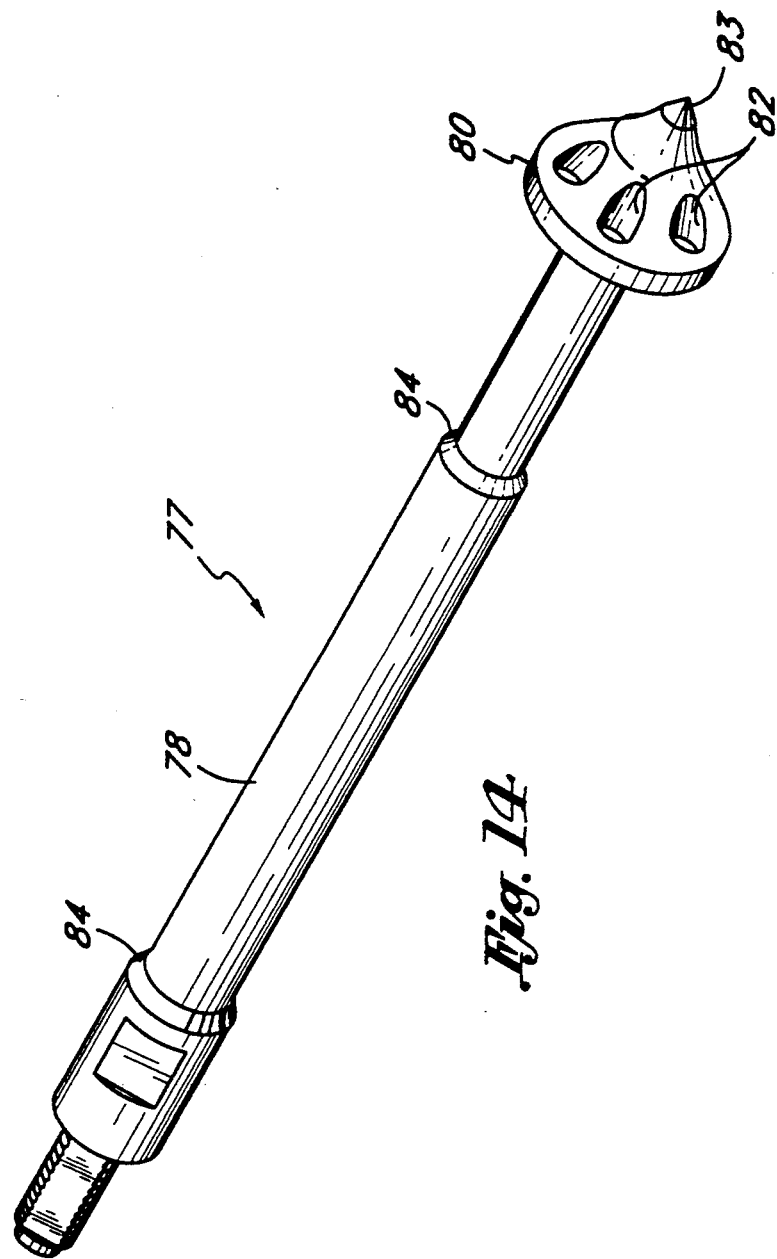

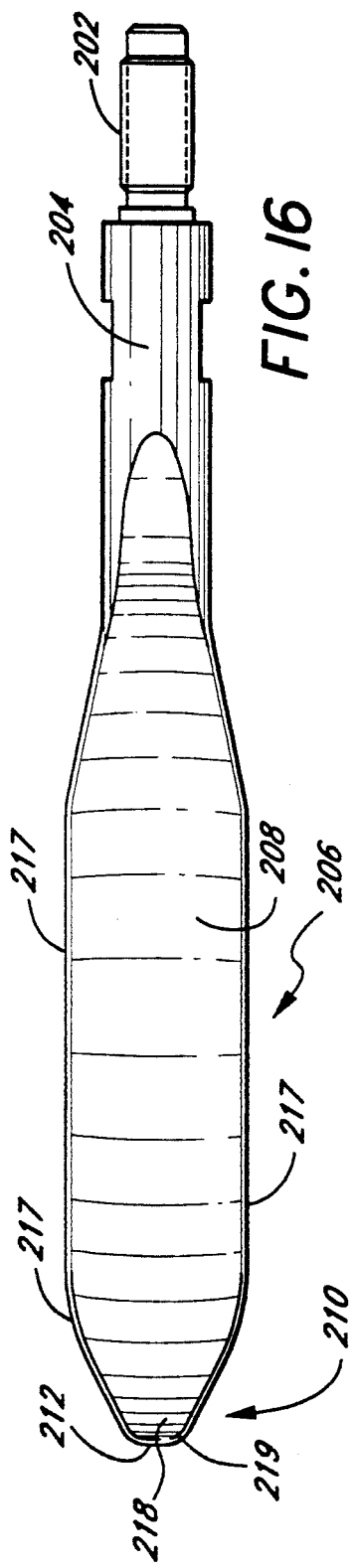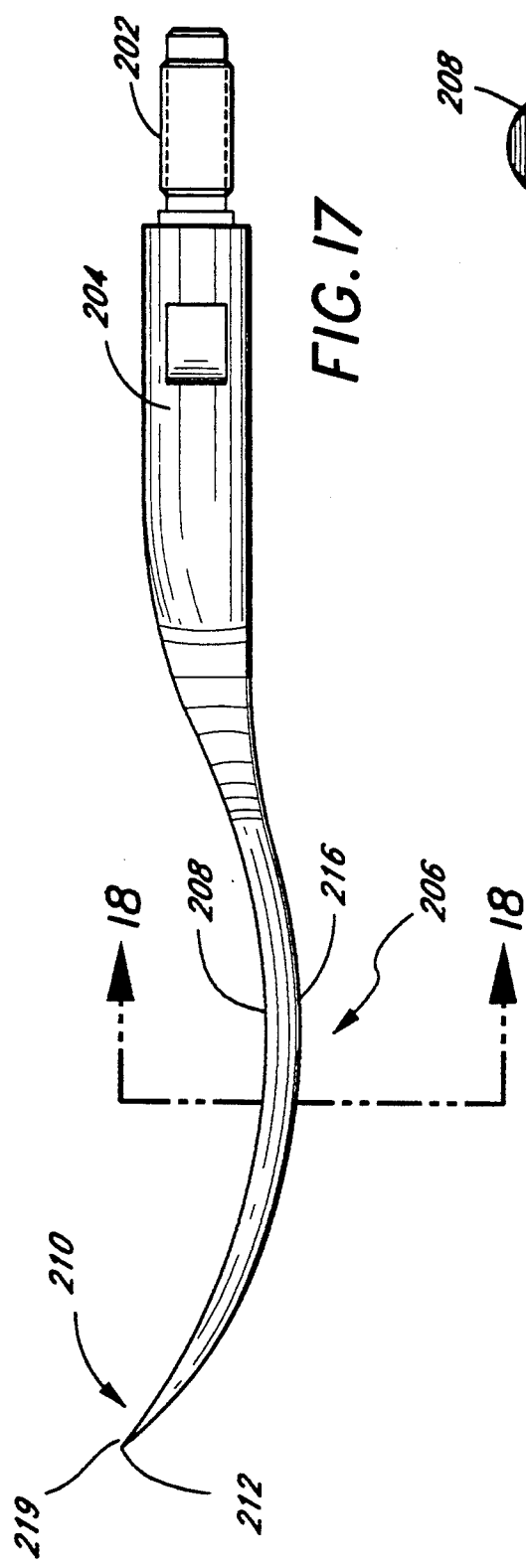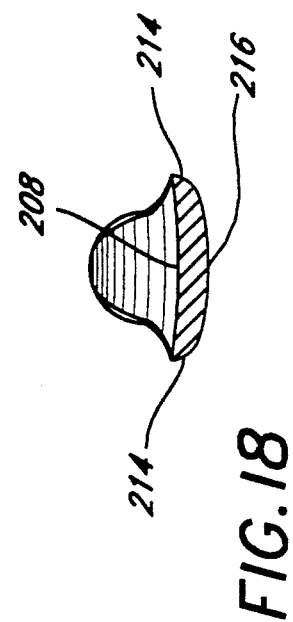

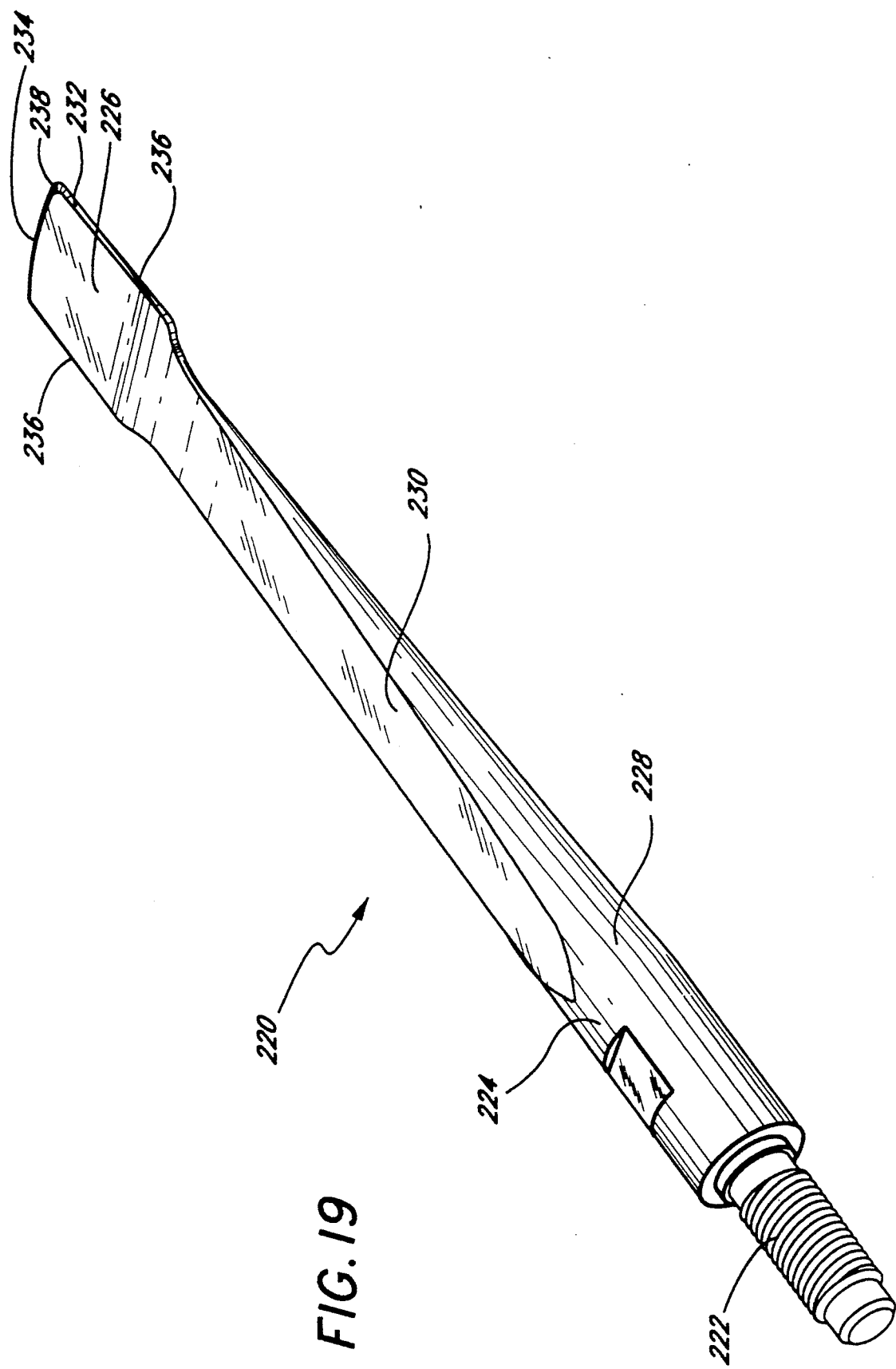

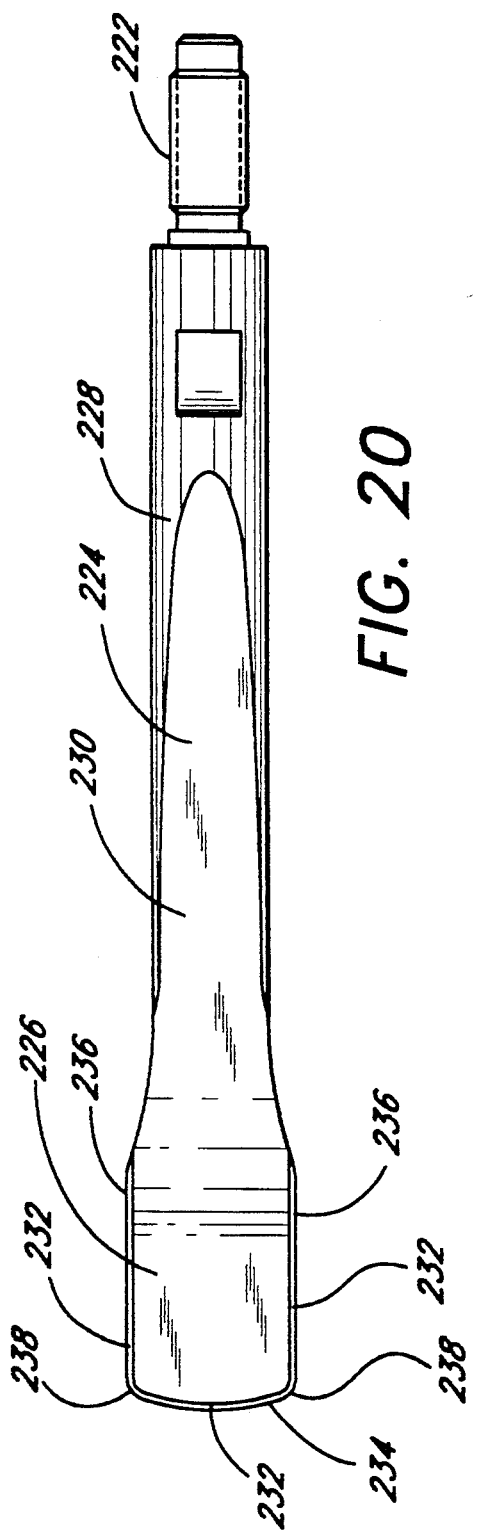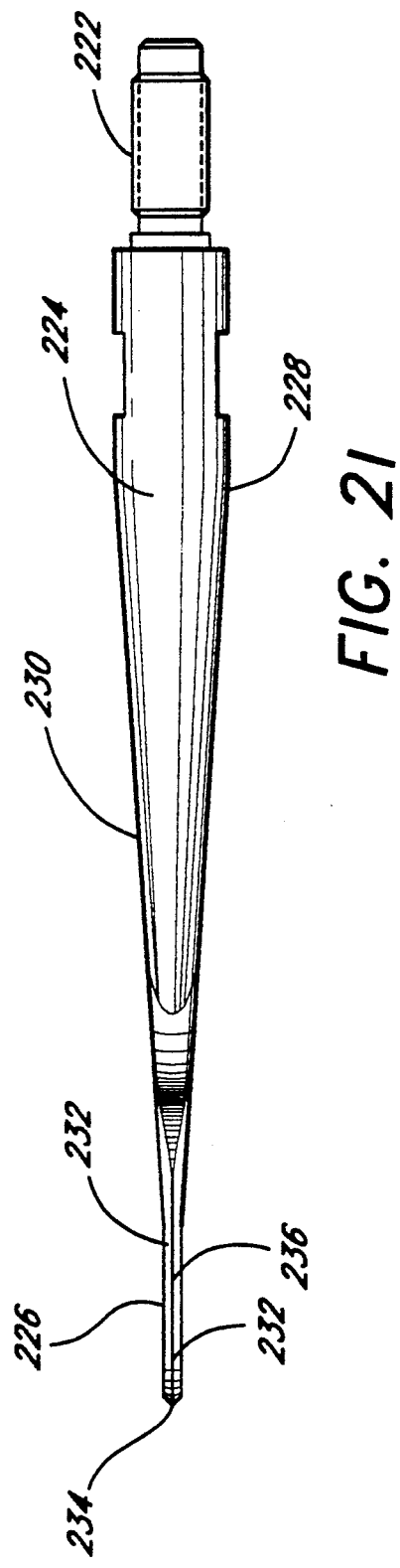

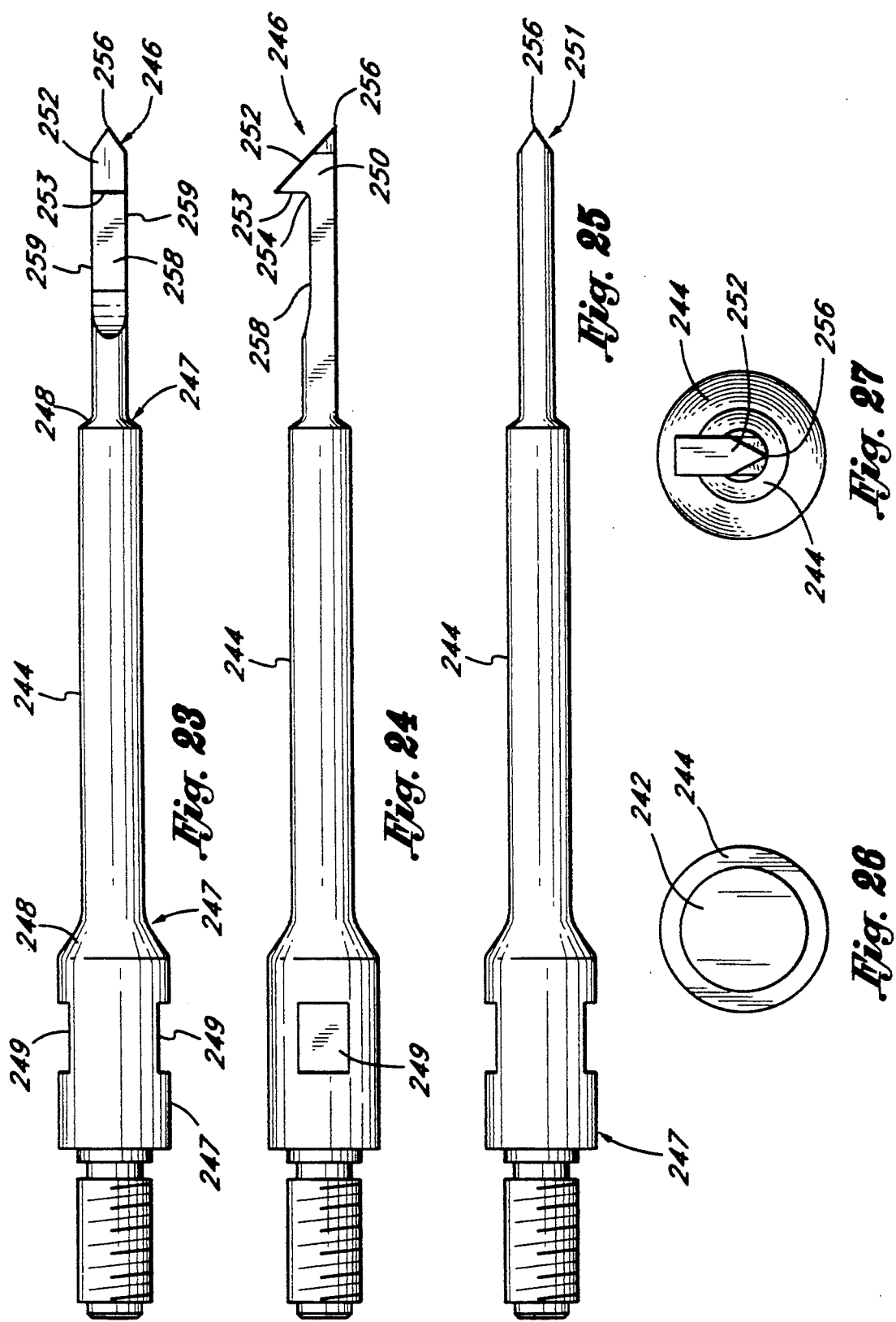

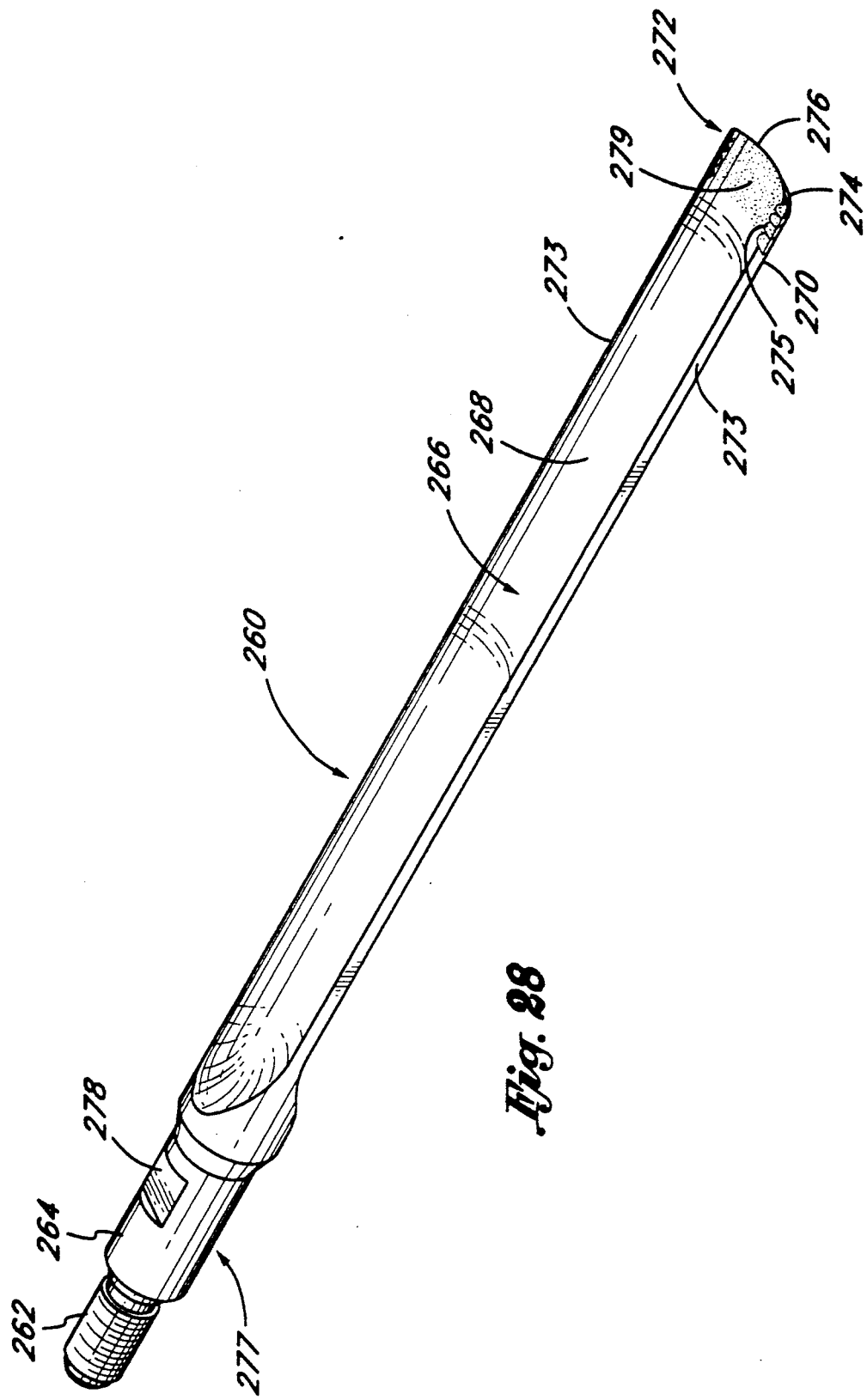

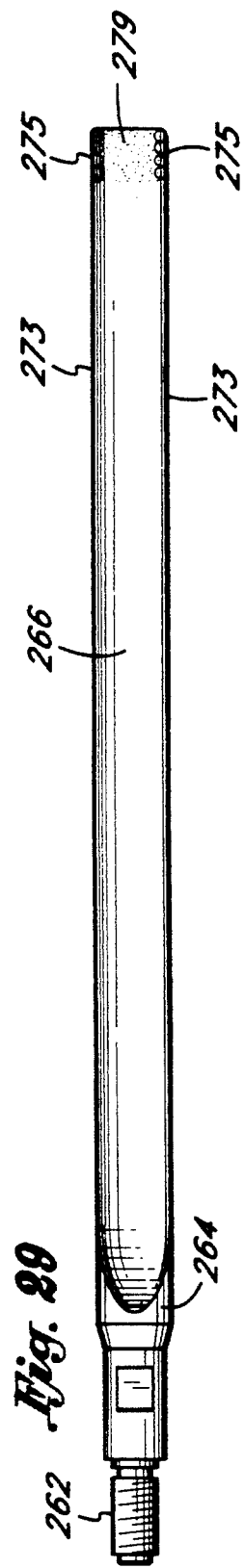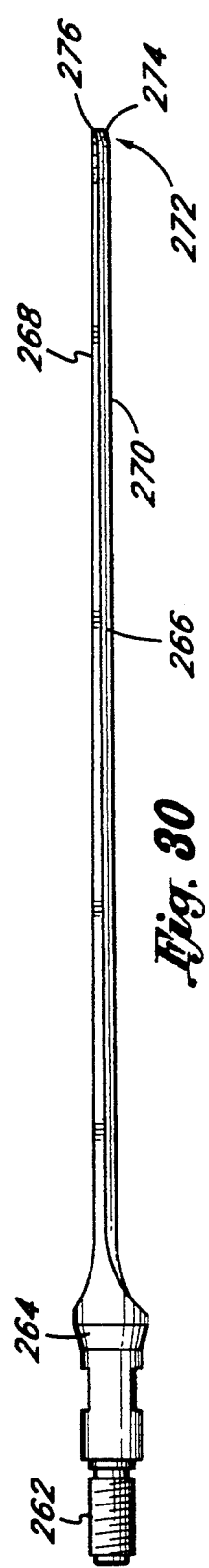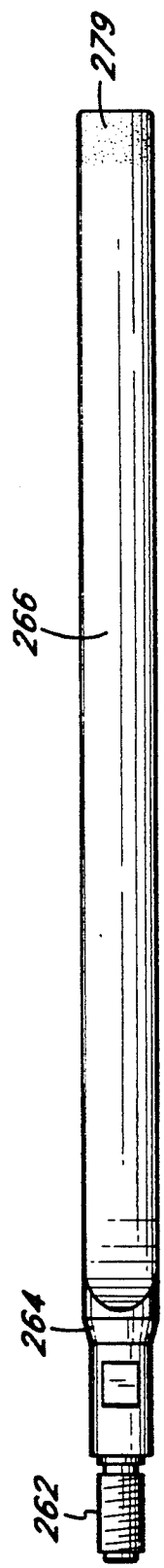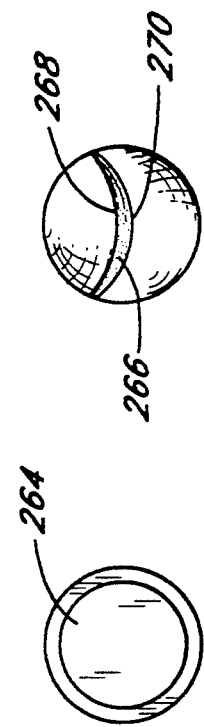

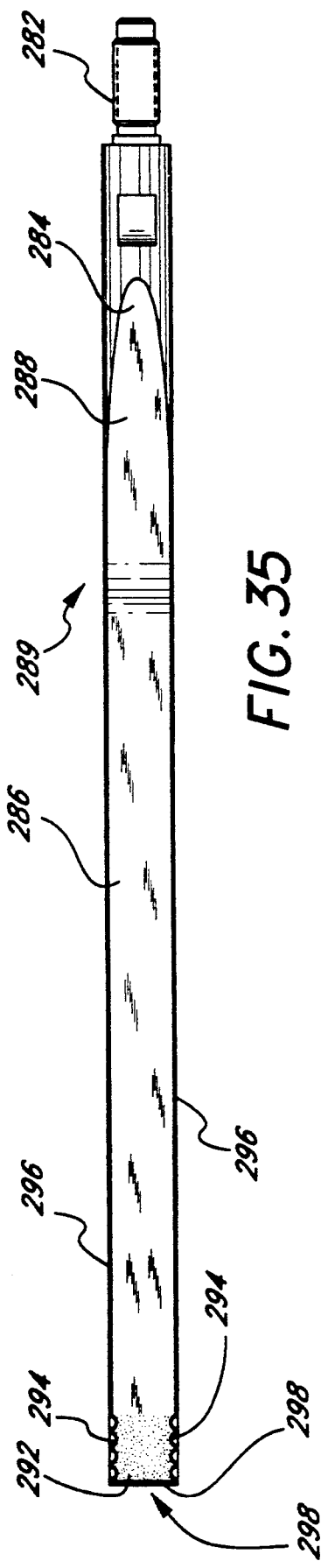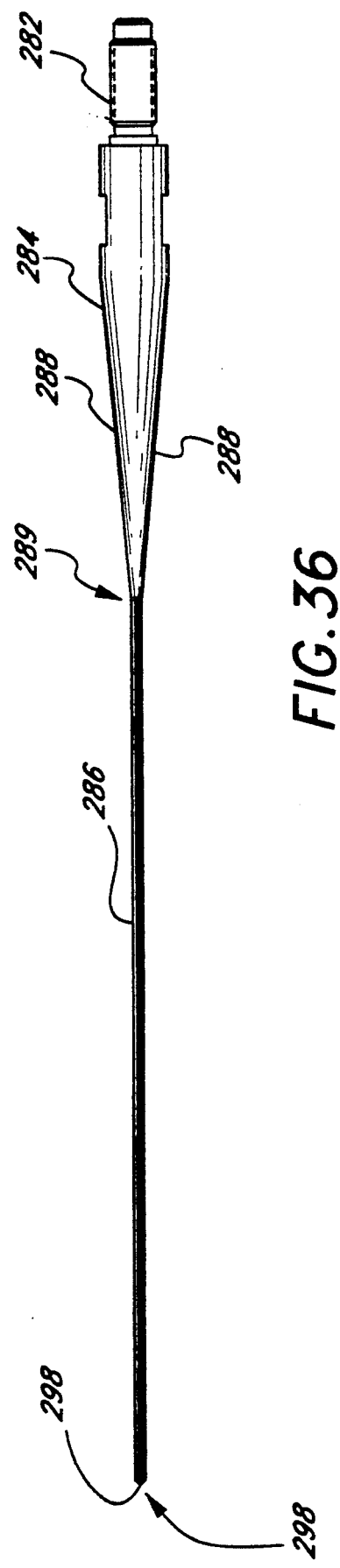

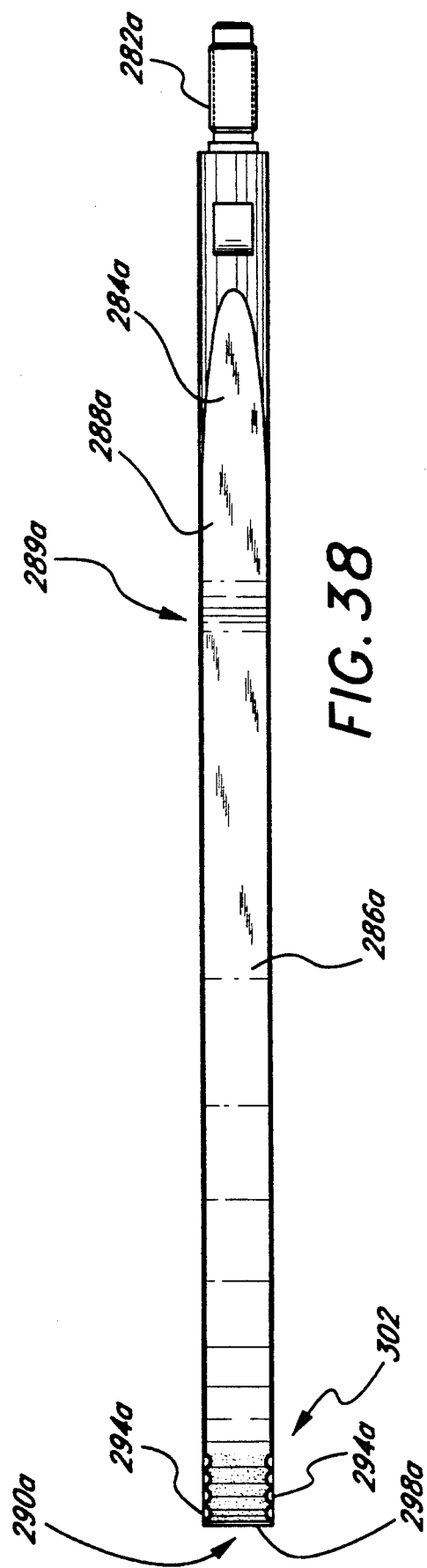
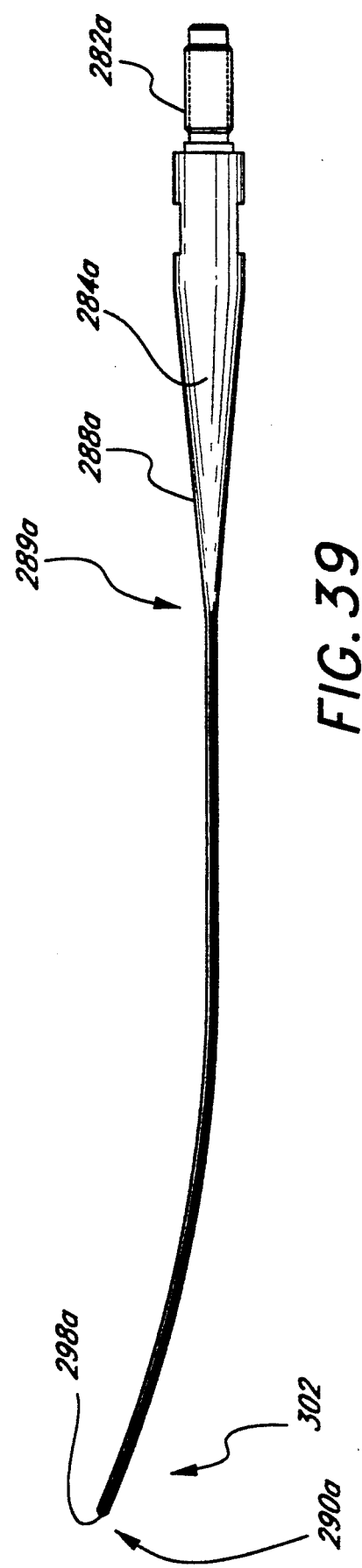

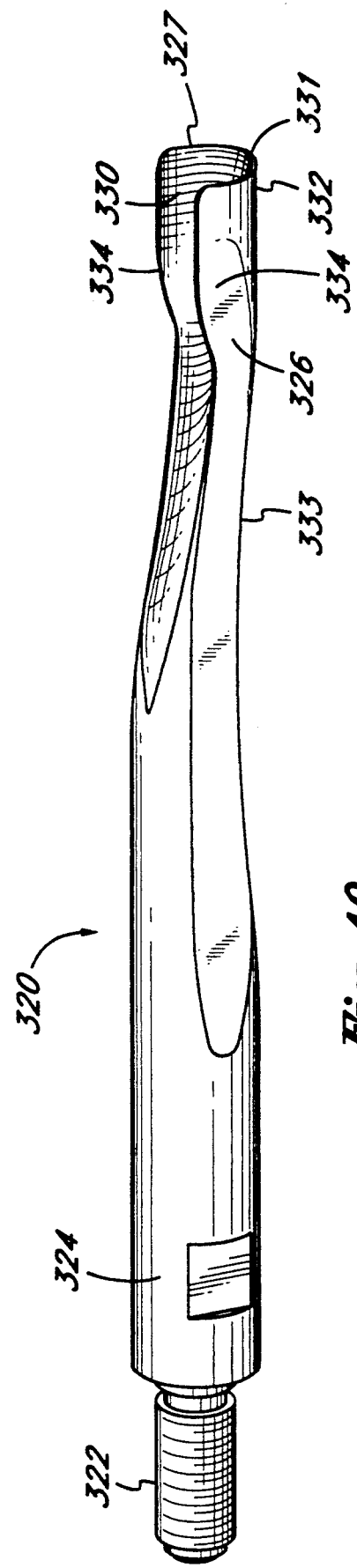

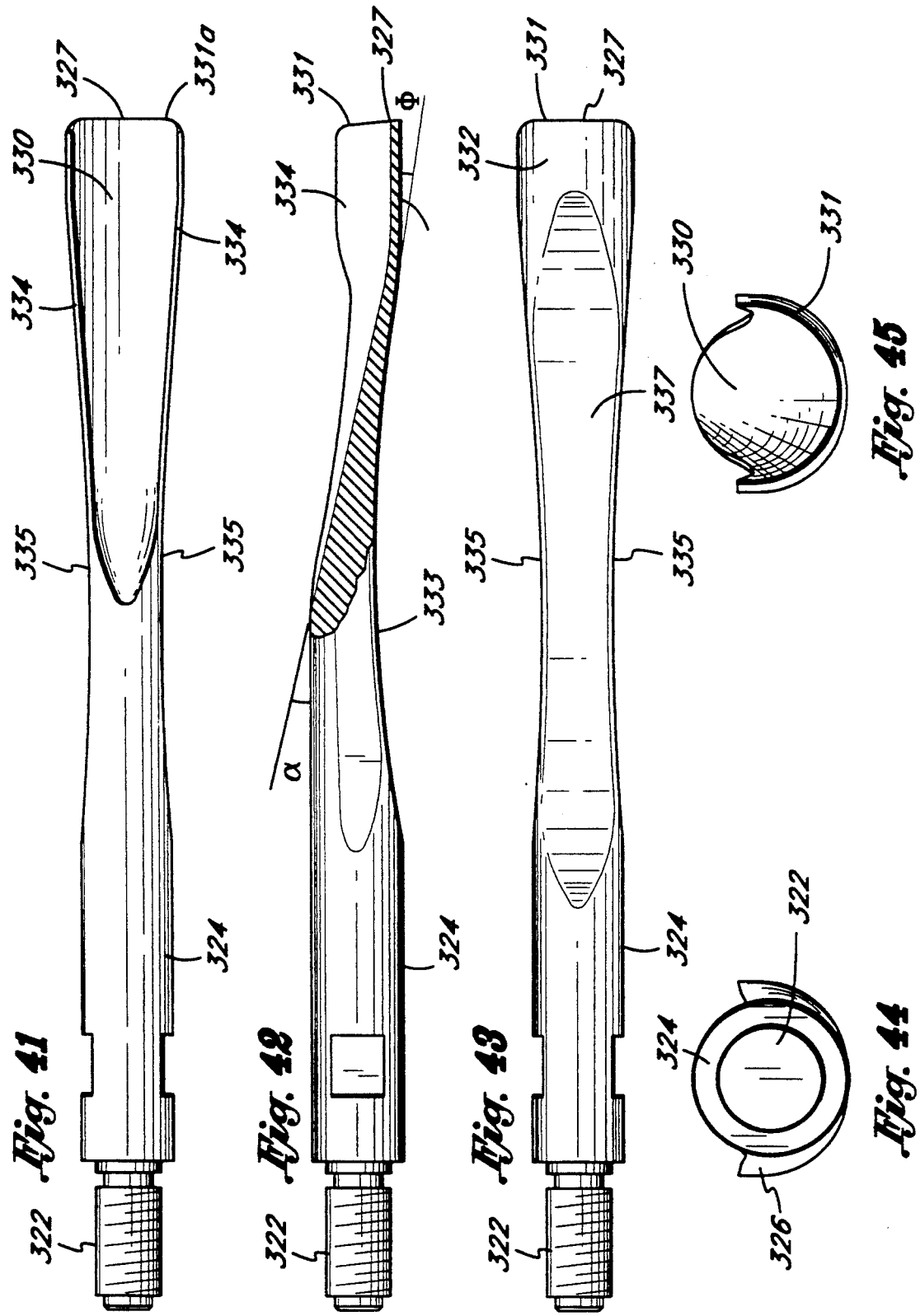

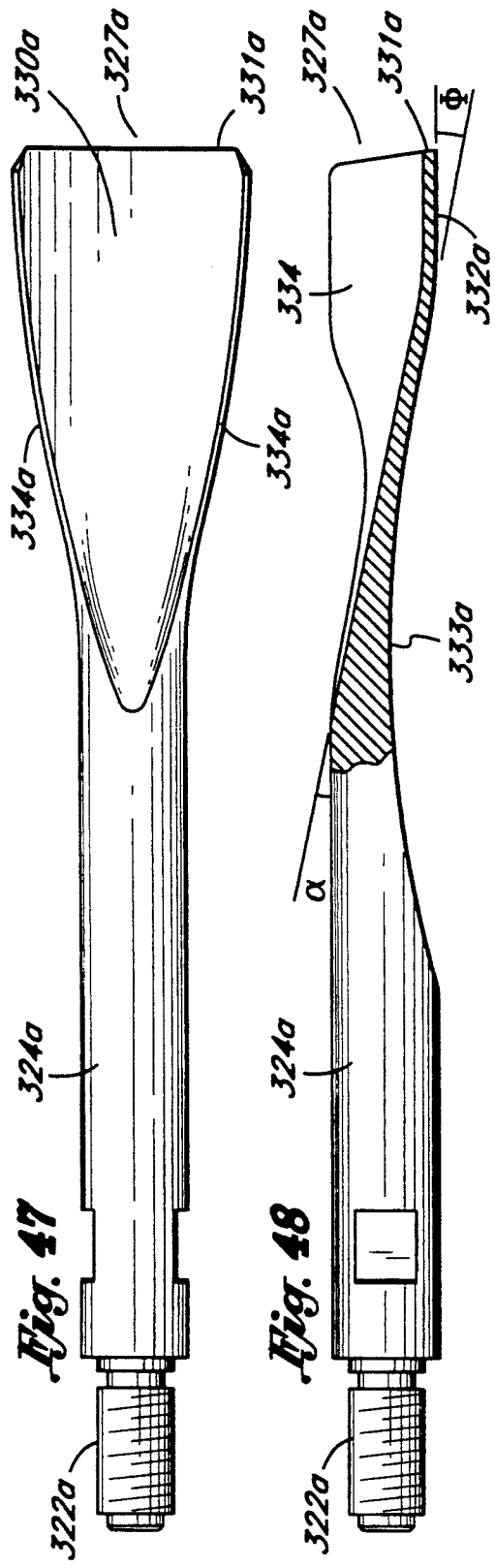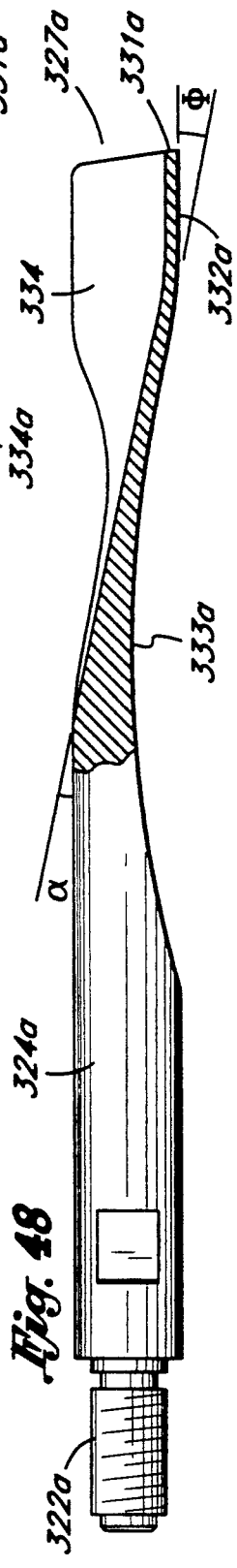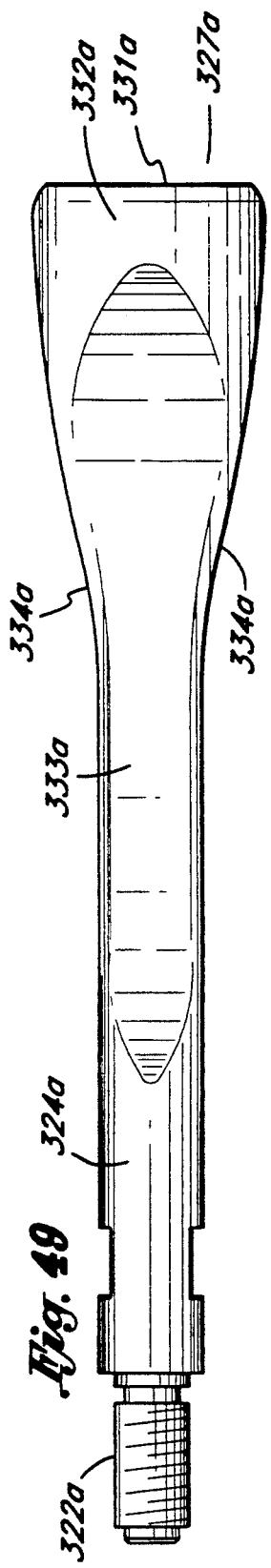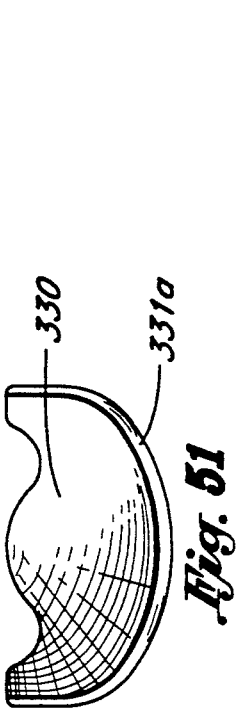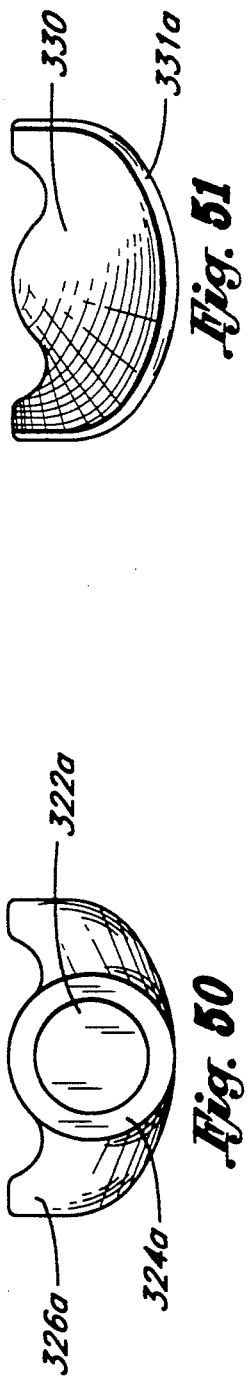

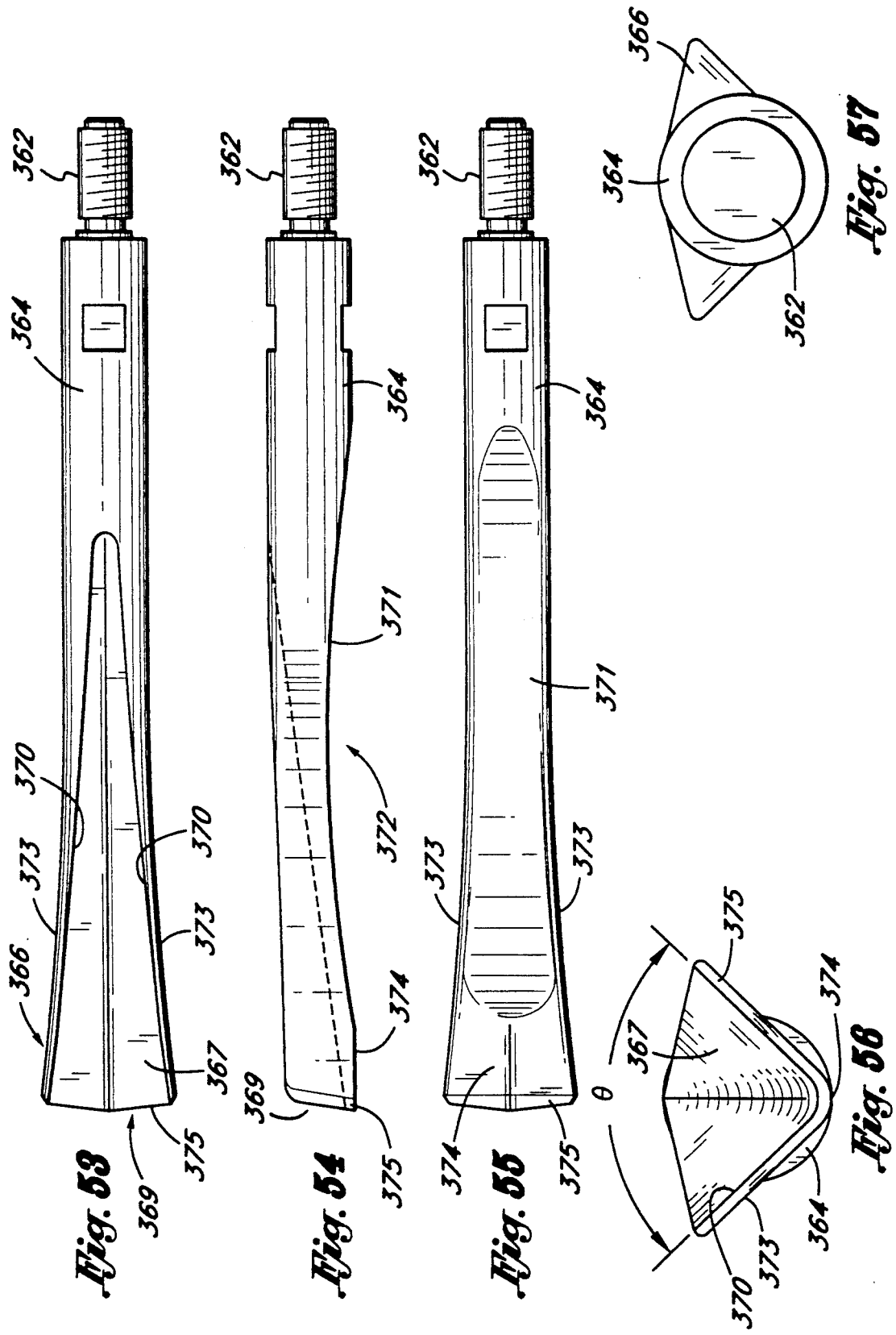

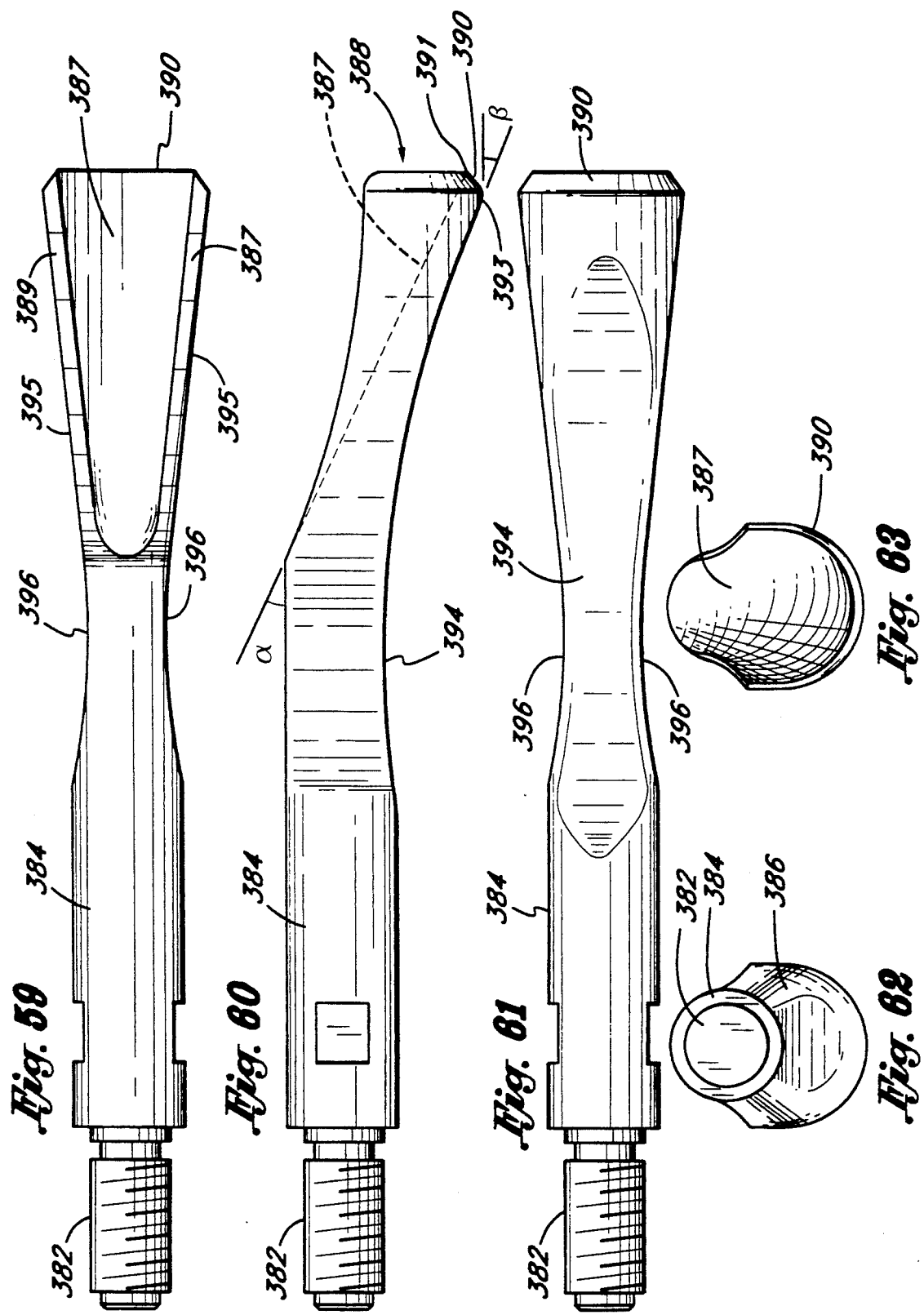

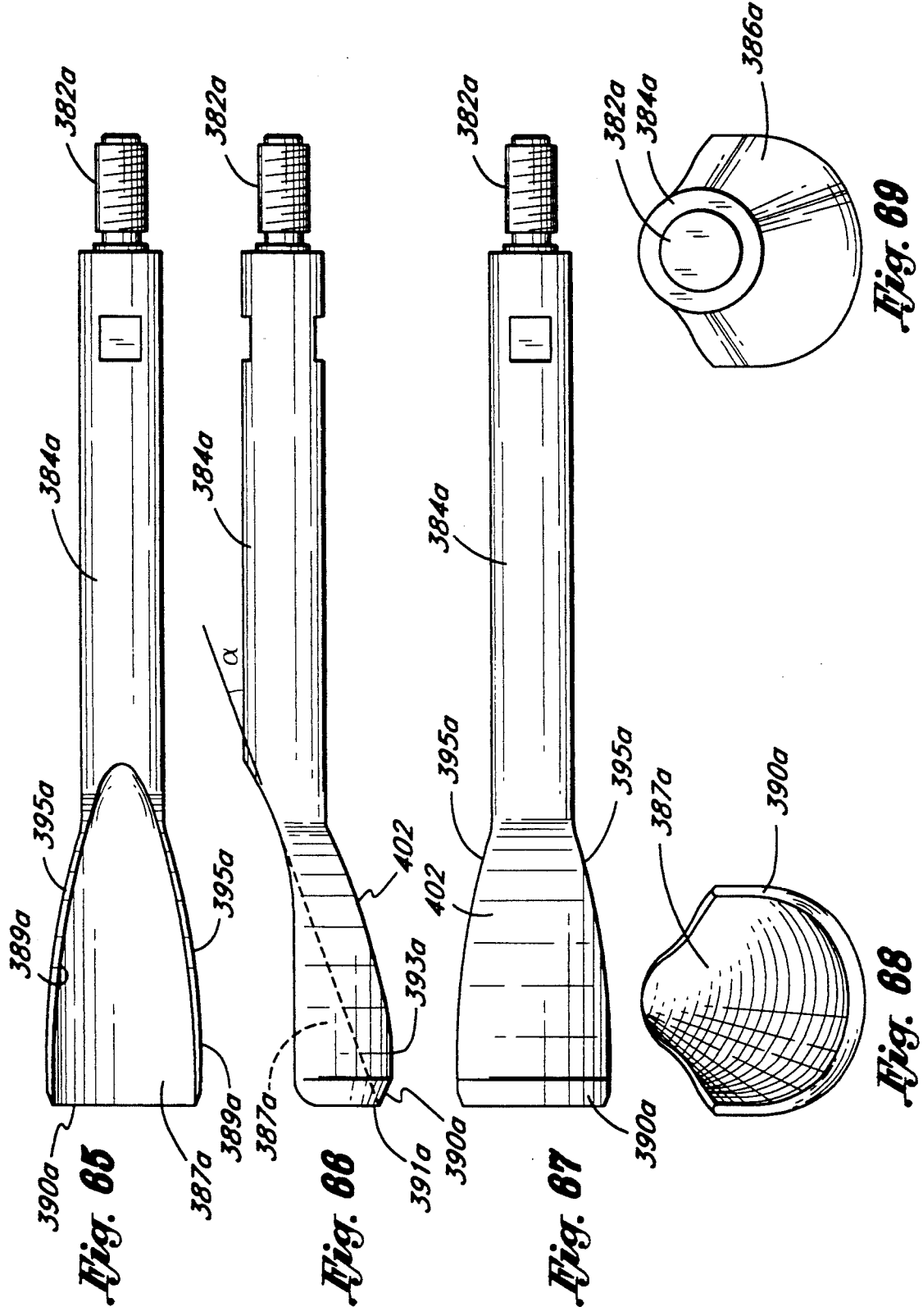

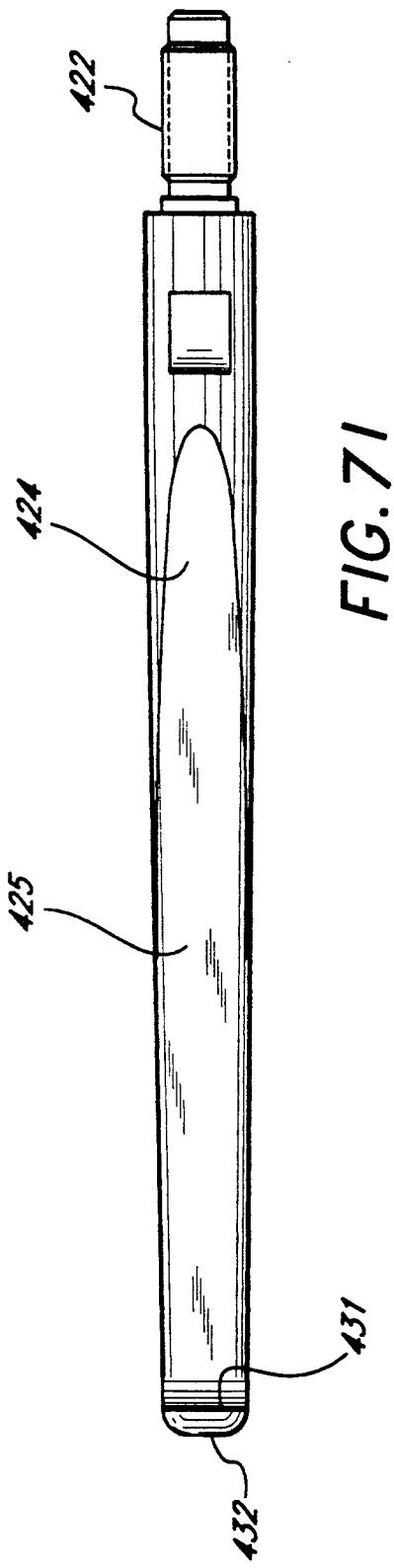
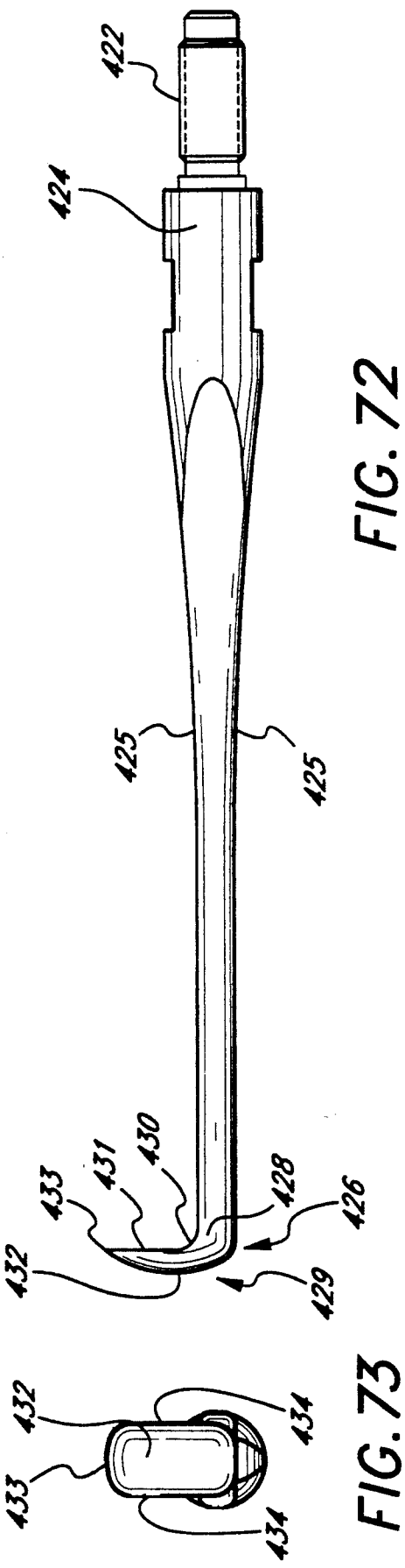

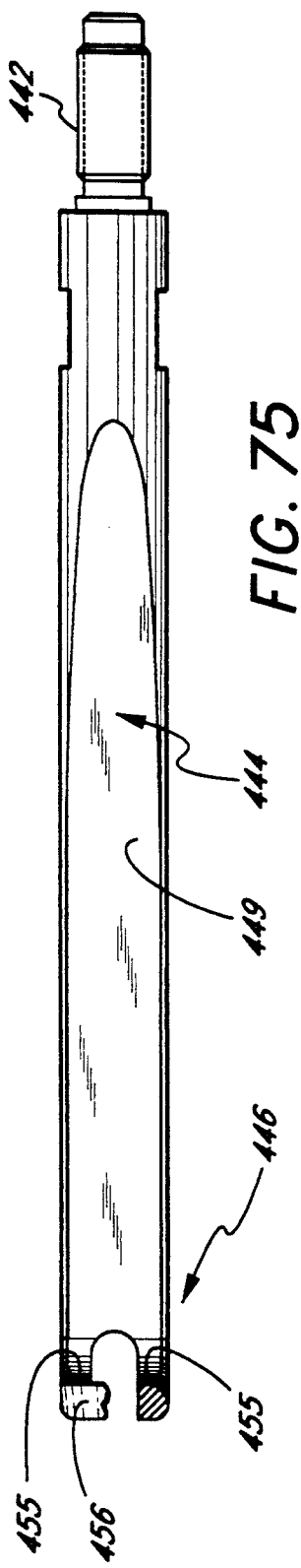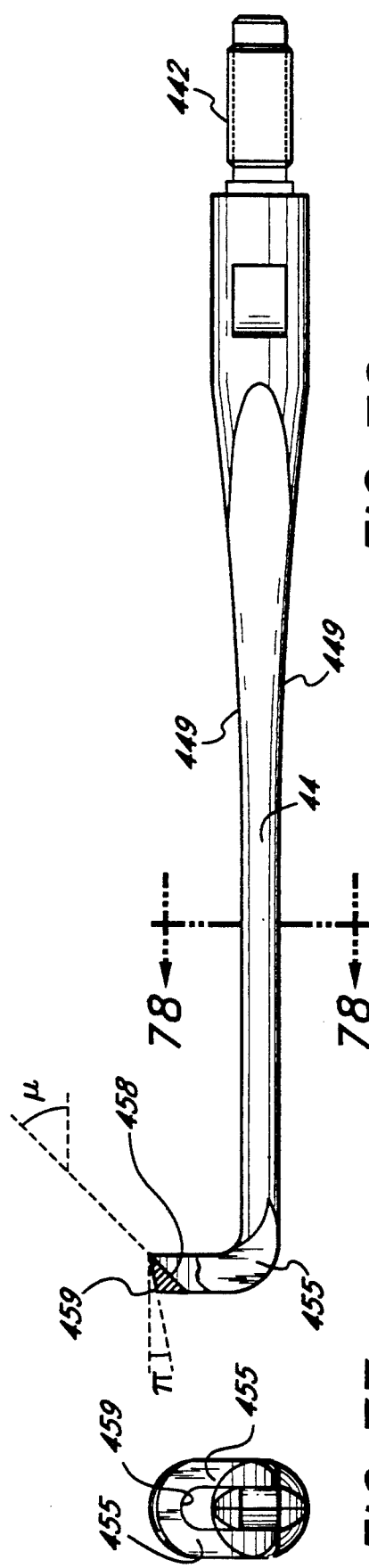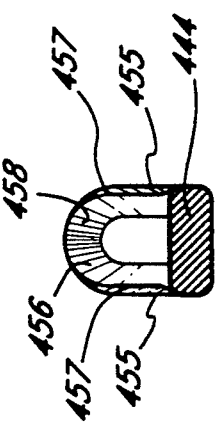
FIG. 75
FIG. 76
FIG. 77
FIG. 78

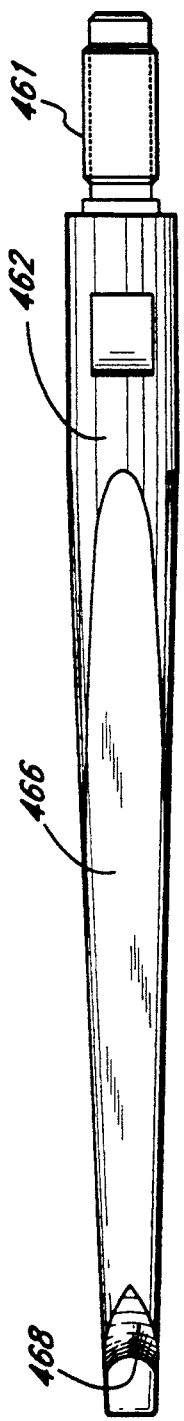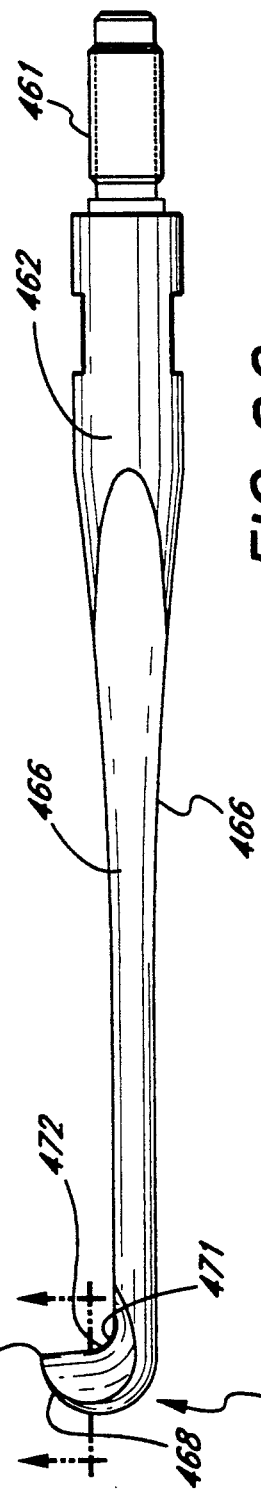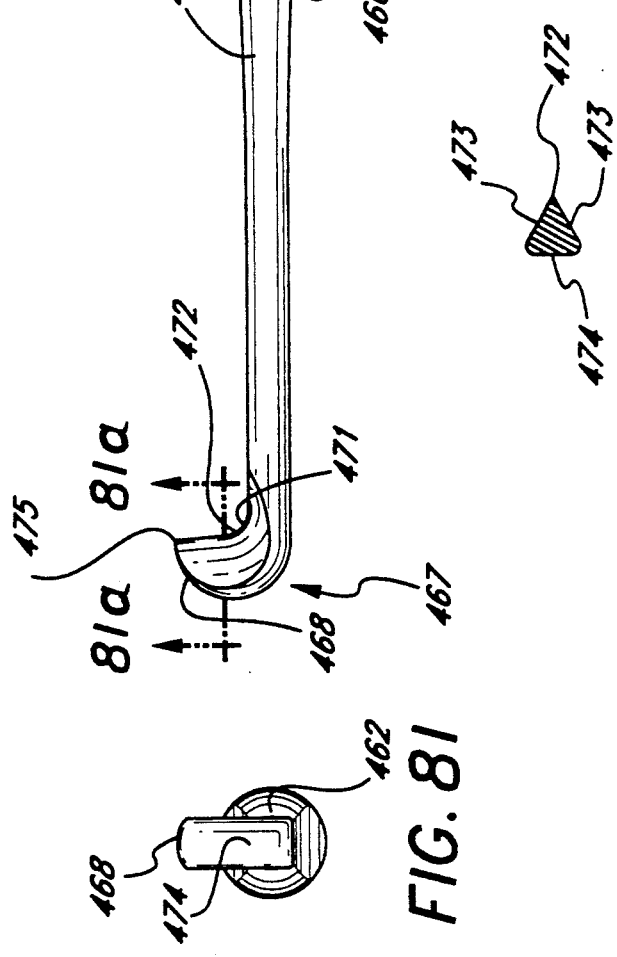

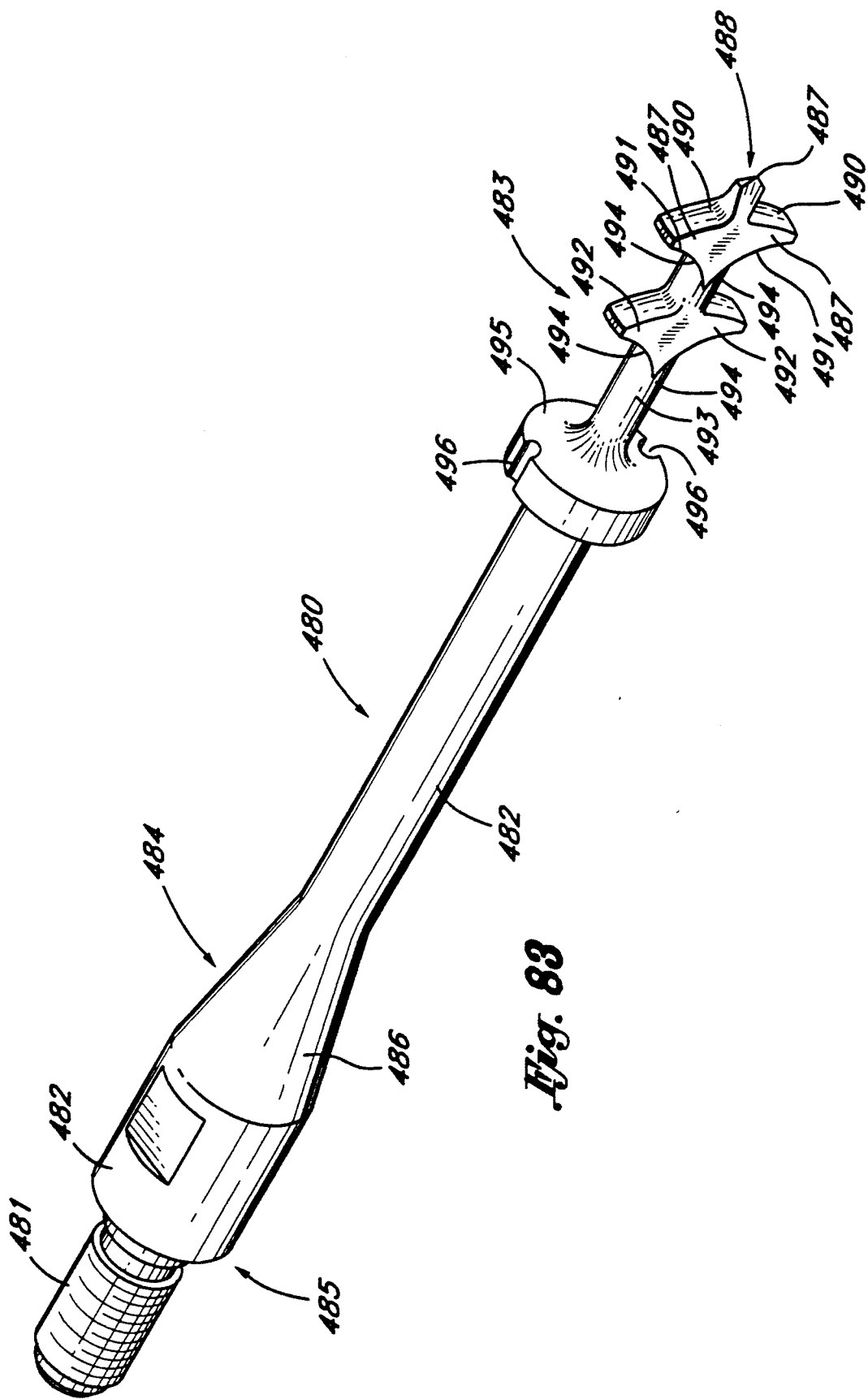

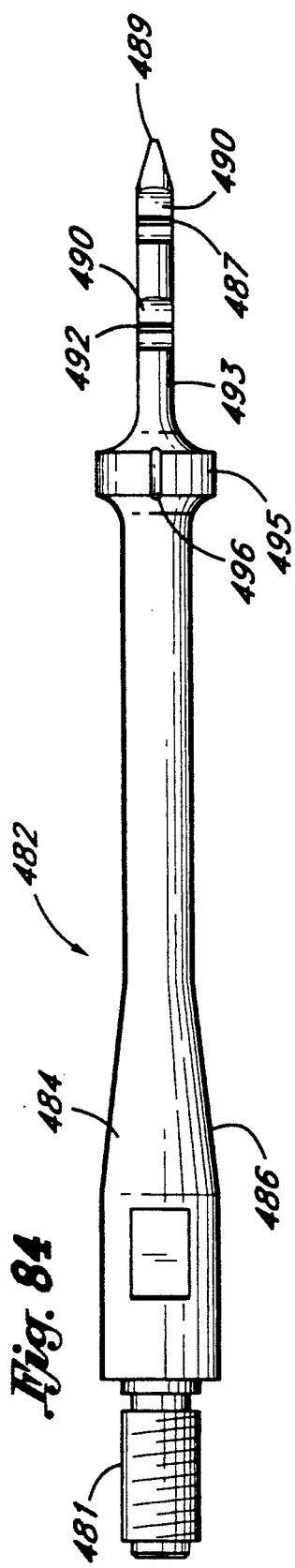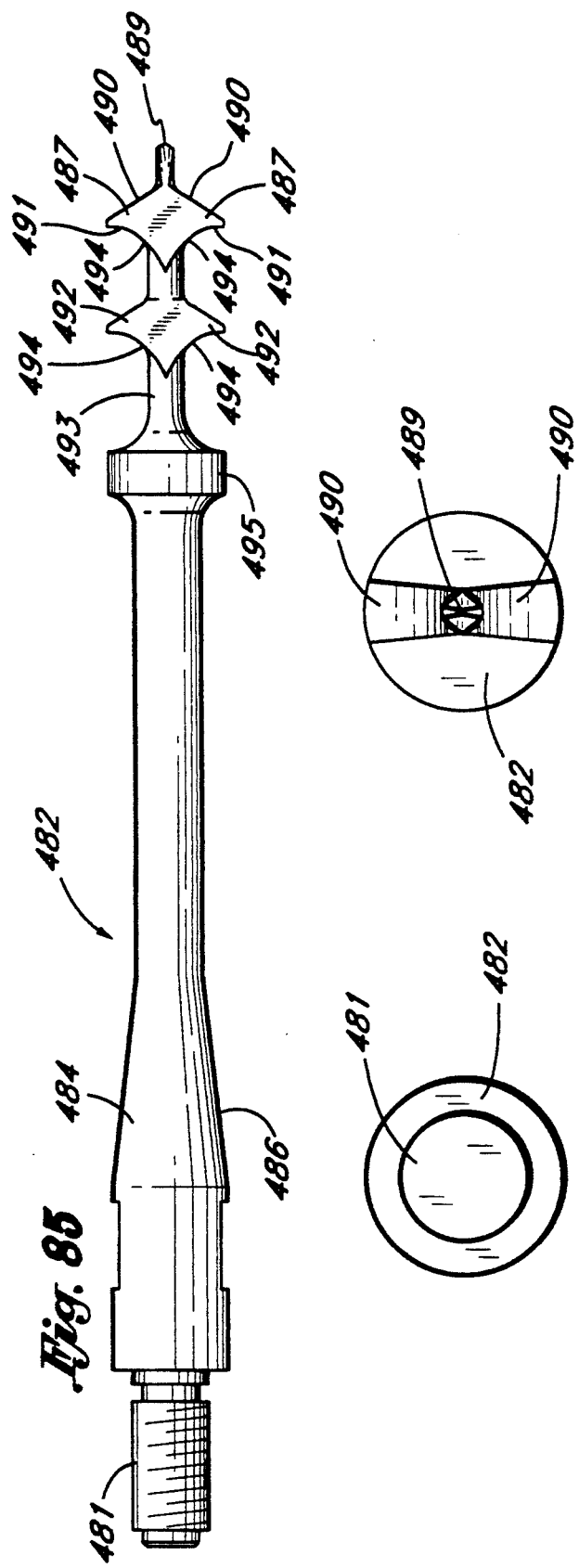

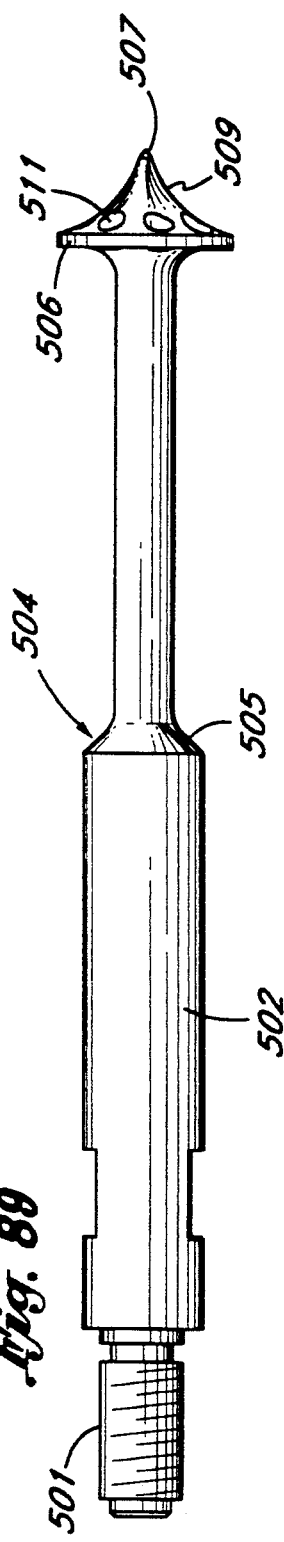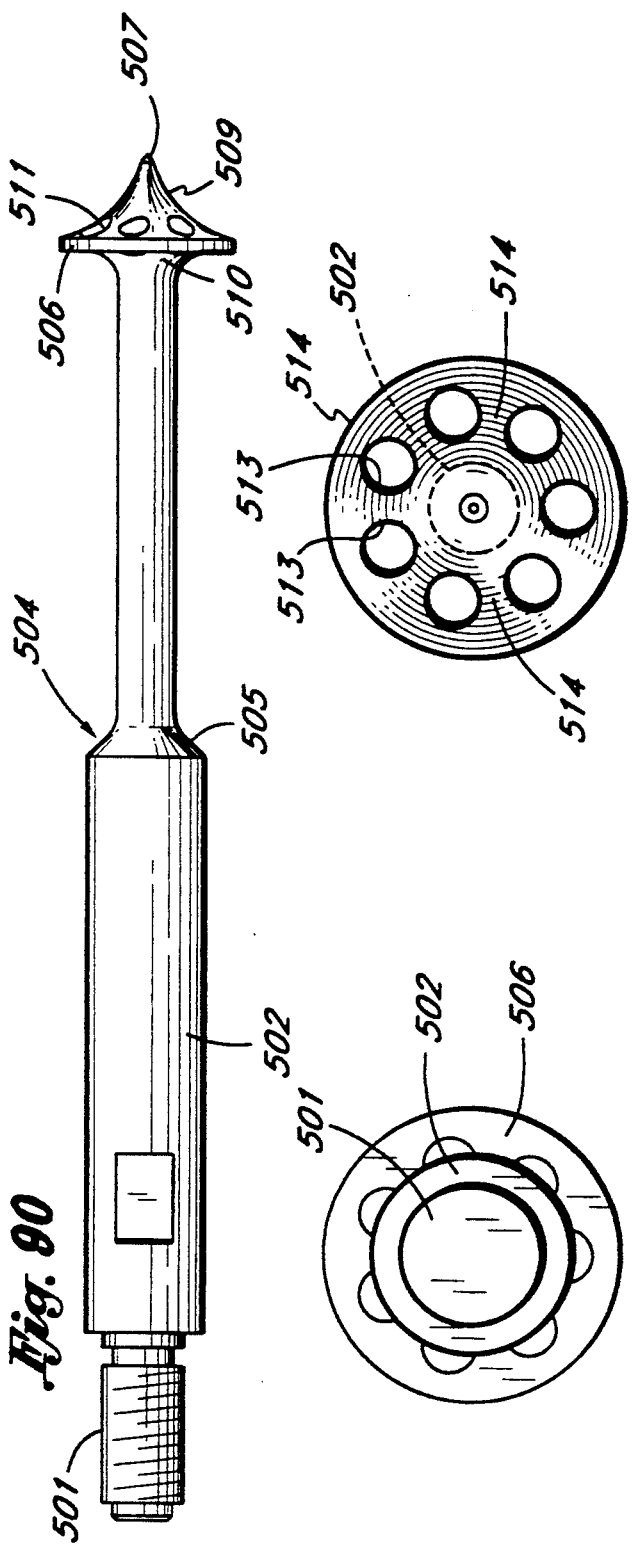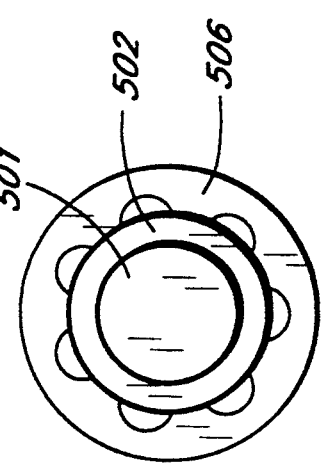

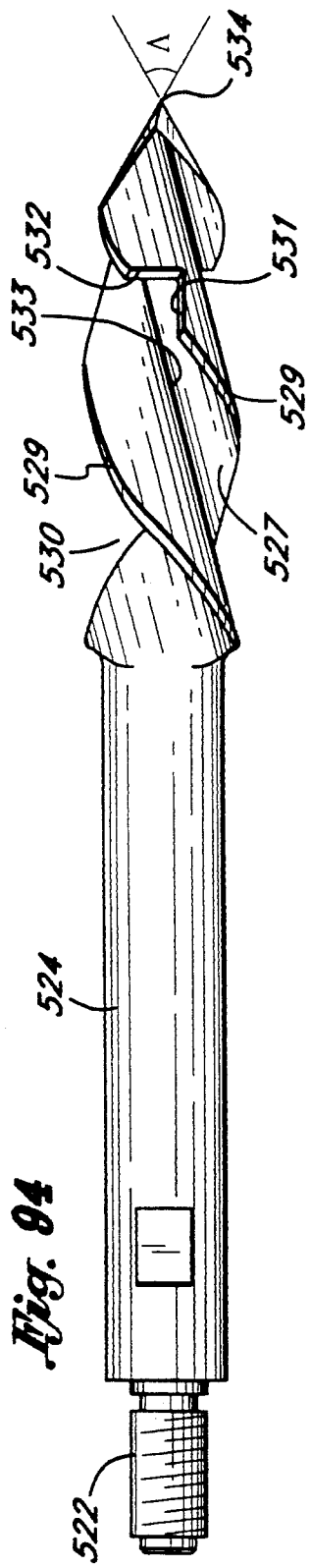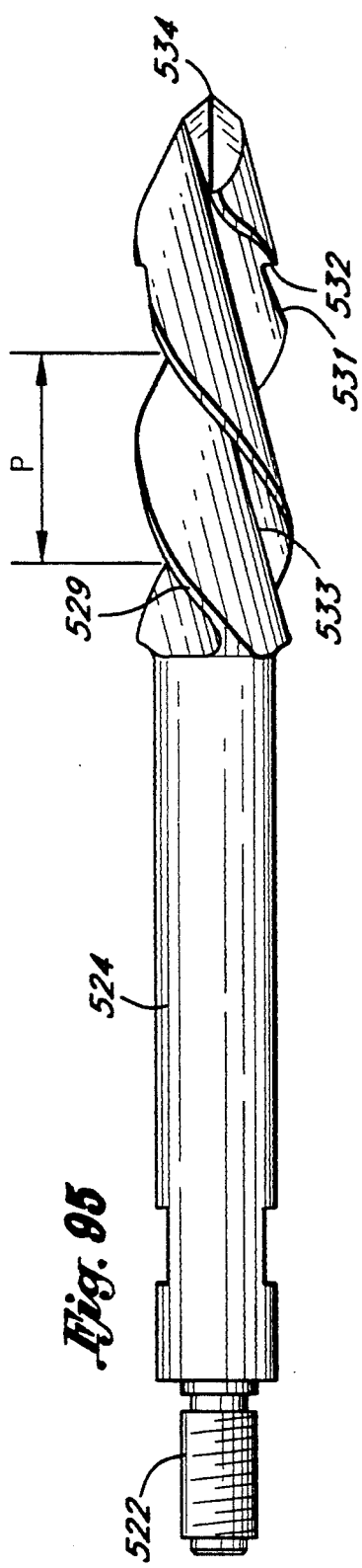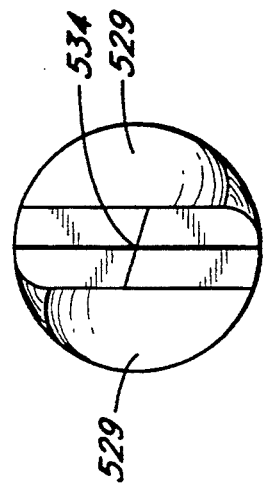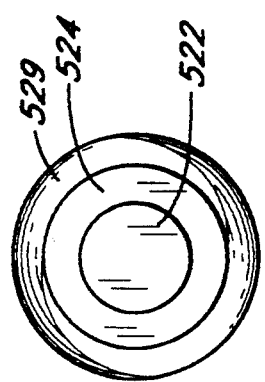

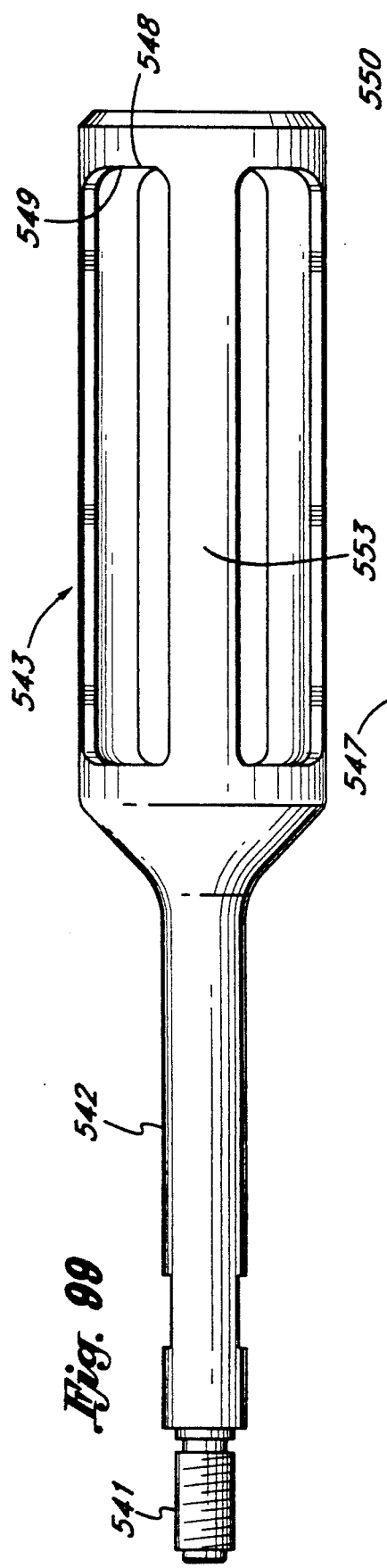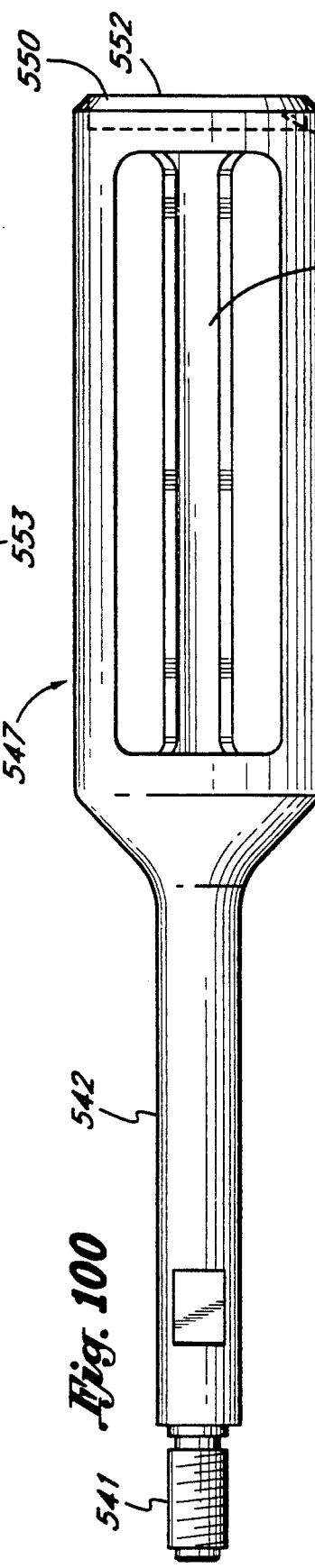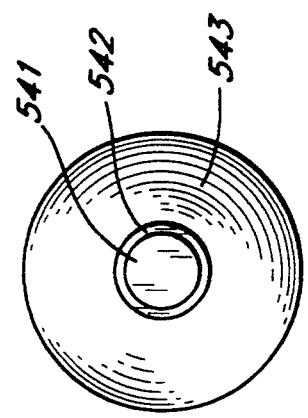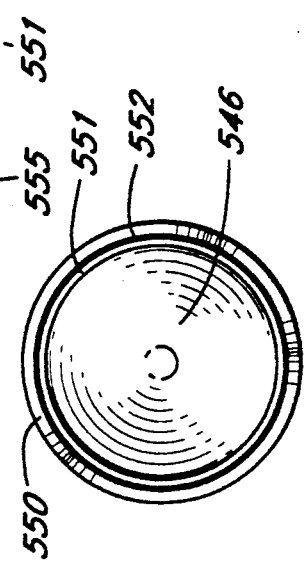

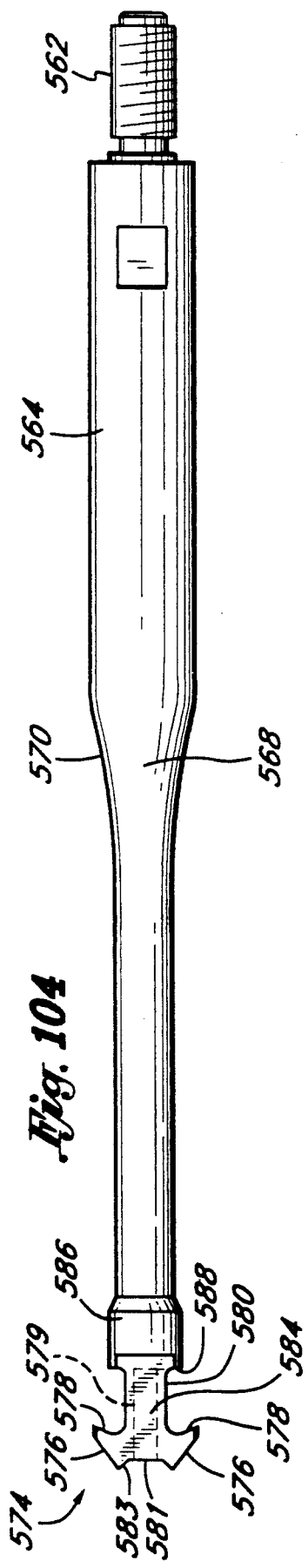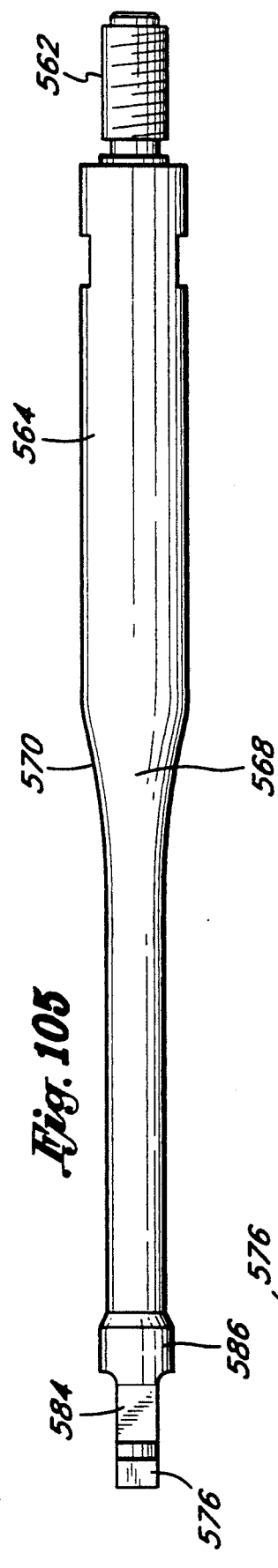

ULTRASONIC TOOL

RELATED APPLICATIONS

The present application is a continuation-in-part of a co-pending application, Ser. No. 665,418, filed Mar. 5, 1991 which is a continuation-in-part of Ser. No. 304,820, filed Jan. 31, 1989, now U.S. Pat. No. 5,019,083, issued May 28, 1991.

FIELD OF THE INVENTION

This invention relates to techniques and apparatus for introducing and removing an orthopedic prosthesis such as a femoral component of a hip joint replacement, acetabular cup, knee joint, shoulder joint, or the like.

BACKGROUND OF THE INVENTION

It has been over sixty years since the first use of replacement parts for hip joints. There have been many advances in the prosthetic components, materials, surgical techniques and the like, so that total hip joint replacement has become relatively commonplace. Related techniques have also been used for replacing knee and shoulder joints.

There are two principal components to a hip replacement prosthesis. One is an acetabular cup which is implanted in the acetabulum. The acetabular cup provides a spherical socket which is the bearing surface for the replacement joint. The other component comprises a femoral stem which is fitted into the medullary canal of the femur and a femoral head on the steam having a spherical surface which meets with the acetabular socket.

The femoral portion of the prosthesis is inserted by cutting off the femoral neck with or without removing the greater trochanter. The medullary canal is then prepared using drills, reamers and successively larger rasps to produce a cavity which is closely complementary to the femoral stem. After cleaning, the femoral stem is driven into place in the canal with what is essentially a press fit. Preparing the cavity to fit the stem is tedious and prolongs the period the patient must be kept under anaesthesia.

The femoral stem may be held in place by a polymethylmethacrylate cement (PMMA) or it may be provided with a porous surface on the shank which accommodates ingrowth of cancellous bone which secures the femoral component in the femur.

The acetabular cup is implanted after grinding a socket in the pelvis to receive it. The acetabular cup may be secured with cement, or may be fastened to the bone with screws after a press fit. Similar techniques, differing in detail are used for implanting replacement shoulder joints, knees and the like.

Despite advances in the technology of hip replacement, it is found that a substantial number of "revisions" are required. Such revisions involve removing components of the hip joint and replacing them. Such revisions may be required shortly after the original surgery due to complications. More commonly they occur eight or ten years after the original surgery due to any of a number of problems that may arise. Such revisions are traumatic for the patient, tedious for the surgeon, and quite time consuming for surgical staff and facilities.

A principal problem in revisions is removal of the femoral component. Some such components are made with transverse holes or threaded holes for connection of tools to extract the femoral stem from the medullary canal. Repeated hammer blows may be applied for driving the stem out of the cavity. Sometimes a window is cut in the femoral cortex near the distal end of the shank, and a punch and hammer are used for driving the shank toward the open end of the femur. Trauma to the patient can be severe and breakage of parts of the femur is not unusual. The techniques employed for removing the femoral component have been characterized as barbaric.

Another technique that has been attempted is removal of the polymethylmethacrylate with an ultrasonically vibrated osteotome. Such a technique is described in U.S. Pat. No. 4,248,232 by Engelbrecht. The osteotome is used for scooping out polymethylmethacrylate cement softened by the ultrasonic vibrations.

Other techniques involve use of long, thin osteotomes for cutting either the cement used for securing the prosthesis in the medullary canal or cancellous bone in the case of an ingrowth prosthesis. In effect, the osteotomes are long chisels which are tapped to disintegrate the cancellous bone or cement and free the prosthesis from the surrounding cortex. For example, in a paper entitled "Atraumatic Removal of a Well-Fixed Porous Ingrowth Hip Prosthesis," Orthopedic Review, Vol. 15, No. 5, June 1986, page 387, Doctors McClelland, James and Simmons describe removal of a femoral component "by the use of an oscillating saw and long, thin osteotomes to carefully separate the prosthesis from its intra-medullary environment. This portion of the procedure was both tedious and somewhat time-consuming, but no iatrogenic damage to the cortical tube of the proximal femur resulted. After the proximal half of the prosthesis had been freed up in this manner, the prosthesis was then extractable, using multiple heavy hammer blows applied to vise grips attached to the end of a McReynolds-wedge extractor."

It is clear that faster and less traumatic techniques are desirable for removing components of prostheses inserted in the medullar canal. It is also desirable to provide quicker and easier techniques for implanting prostheses. In addition, there remains a need for a quick release connector for permitting the rapid connection and disconnection of surgical tool tips and extenders to a source of ultrasonic energy, which permits the efficient propagation of ultrasonic energy therethrough.

SUMMARY OF THE INVENTION

There is provided in accordance with one aspect of the present invention a junction for rapidly connecting and disconnecting ultrasonic surgical components for the transfer of ultrasonic energy across said junction from a source thereof to an ultrasonically activated working tip. The junction comprises a generally cylindrical male component having at least two axially-extending splines spaced apart by at least two axially-extending flats. A female component is provided having a generally cylindrical recess with at least two axially-extending flats and at least two axially-extending splines on the interior circumference thereof in a corresponding relationship with the male component.

The female component is adapted to receive and be rotated with respect to the male component to interlock the corresponding splines and to provide a relatively high compression junction therebetween to enable an efficient transfer of ultrasonic energy. Preferably, axial compressions in excess of about 300 pounds will be achieved. More preferably, axial compressions in excess of about 600 pounds, and most preferably in excess of about 1,000 pounds will be achieved. In addition, the foregoing axial compressions are preferably achieved by a rotation of the male component with respect to the female component of approximately 90° plus or minus 10°.

In accordance with another aspect of the present invention, an ultrasonic medical tool is provided. The ultrasonic medical tool comprises an ultrasonic transducer, an ultrasonic energy activated tip, and at least one extender extending between the transducer and the tip for conducting ultrasonic energy from the transducer to the tip. The extender is connected to the tip by means of at least one junction of the type defined above.

In accordance with a further aspect of the present invention, there is provided a method for conducting a medical procedure, of the type using a plurality of different ultrasonic energy activated working tips. In accordance with the medical procedure method, an ultrasonic energy transducer is provided which is coupled to a first ultrasonic energy activated working tip by at least one junction of the type defined above. The transducer is activated to transmit ultrasonic energy to the tip, and at least a portion of the medical procedure is performed.

Thereafter, the first ultrasonic energy activated tip is removed by rotation of the tip with respect to the transducer. A second ultrasonic energy activated tip is thereafter selected, and coupled to the transducer by way of a rotation of the second tip with respect to the transducer. The medical procedure is thereafter continued, utilizing the second ultrasonic energy activated tip. Preferably, the medical procedure comprises the implantation or the removal of an endoprosthesis from the medullary canal. Alternatively, the medical procedure comprises the removal of cement from the medullary canal.

In accordance with a further aspect of the present invention, there is provided a method of removing cement or adhesive from the interior surface of the medullary canal. In accordance with the adhesive removal method, an ultrasonic transducer is coupled to an ultrasonic energy activated adhesive cutting tool. The coupling is accomplished by inserting a male component in communication with one of the transducer and the tool within a recess in communication with the other of the transducer and the tool, and rotating the tool with respect to the transducer through an angle of about 90°. The cutting tool is thereafter positioned in contact with the adhesive and activated so that the adhesive may be cut with the cutting tool.

In accordance with another aspect of the present invention, there is provided a plurality of polymethylmethacrylate (PMMA), polymer and tissue modification tools ultrasonically activated to remove orthopedic prostheses and PMMA cement from the human skeleton. The tools efficiently propagate ultrasonic energy and minimize the amount of heat transferred to the surrounding tissue at the surgical site.

Each tool is adapted to couple with an ultrasonic transducer to oscillate a distal end of the tool at a frequency which resonates the mechanical bond between the PMMA cement and bone (e.g., cancellous or cortical bone) interface, between the bone and a prostheses interface, or in the cement.

In accordance with another aspect of the present invention, there is provided a method for removing a cylindrical cement mantle from an orthopedic prosthesis canal. A surgeon debulks the cement mantle to a wall thickness of about 2 to 10 mm and sections the cylindrical cement mantle into segmental lengths. The surgeon also severs the cylindrical mantle longitudinally to break the hoop strength of the mantle, and effectively produce an arcuate layer of cement easily divided and pried away from the adjacent tissue.

These and other features and advantages of the present invention will become apparent from the detailed description of preferred embodiments which follows, when considered together with the attached drawings and claims.

BRIEF DESCRIPTION OF THE DRAWINGS

FIG. 3 is a schematic view of a medical device including a power supply and an ultrasonic transducer equipped for coupling to a femoral component as illustrated in FIG. 2;

FIG. 4 is a side view of a femoral component including rasp-like teeth;

FIG. 5 is a schematic illustration of an ultrasonic medical tool of the present invention showing a handpiece, an extender and a cement plug removal tool bit;

FIG. 6 is a perspective view of the extender of FIG. 5;

FIG. 7 is a partial cross-sectional view of the ultrasonic medical tool of FIG. 5 taken along line 7—7 illustrating two junctions of the present invention;

FIG. 9 is an exploded perspective view of one of the junctions of FIG. 7, illustrating the generally cylindrical male component on the proximal end of a surgical tool having a pair of splines interrupted by a pair of flats;

FIG. 9a is a cross-sectional view of the junction of FIG. 9 taken along line 9a–9a.

FIG. 10 is an assembly perspective view of the junction of FIG. 9 with a male component inserted into a female component;

FIG. 11 is an assembly perspective view of the junction of FIG. 10 with the components rotated to engage corresponding splines of each component;

FIG. 12 is a cross-sectional view of the junction of FIG. 10 taken along lines 12—12;

FIG. 13 is a cross-sectional view of the junction of FIG. 11 taken along lines 13—13;

FIG. 14 is a perspective view of a disk drill tool tip.

FIG. 16 is plan view of the acetabular tool bit of FIG. 15;

FIG. 17 is a side view of the acetabular tool bit of FIG. 15;

FIG. 18 is a sectional view of the acetabular tool bit taken along line 18—18 of FIG. 17;

FIG. 19 is a perspective view of an osteotome of the present invention;

FIG. 20 is a plan view of the osteotome of FIG. 19;

FIG. 21 is a side view of the osteotome of FIG. 19;

FIG. 23 is a top plan view of the barb tool bit of FIG. 22;
FIG. 24 is a side view of the barb tool bit of FIG. 22;
FIG. 25 is a bottom plan view of the barb tool bit of FIG. 22;
FIG. 26 is a left end view of the barb tool bit of FIG. 24;
FIG. 27 is a right end view of the barb tool bit of FIG. 24;
FIG. 28 is a perspective view of a porous gouge of the present invention;
FIG. 29 is a top plan view of the porous gouge of FIG. 28;
FIG. 30 is a side view of the porous gouge of FIG. 28;
FIG. 31 is a bottom plan view of the porous gouge of FIG. 28;
FIG. 32 is a left end view of the porous gouge of FIG. 30;
FIG. 33 is a right end view of the porous gouge of FIG. 30;
FIG. 35 is a plan view of the long osteotome of FIG. 34;
FIG. 36 is a side view of the long osteotome of FIG. 34;
FIG. 38 is a plan view of the long, curved osteotome of FIG. 37;
FIG. 39 is a side view of the long, curved osteotome of FIG. 37;
FIG. 40 is a perspective view of a gouge of the present invention;
FIG. 41 is a top plan view of the gouge of FIG. 40;
FIG. 42 is a partial cross-sectional side view of the gouge of FIG. 40;
FIG. 43 is a bottom plan view of the gouge of FIG. 40;
FIG. 44 is a left end view of the gouge of FIG. 42;
FIG. 45 is a right end view of the gouge of FIG. 42;
FIG. 47 is a top plan view of the gouge of FIG. 46;
FIG. 48 is a partial cross-sectional side view of the large gouge of FIG. 46;
FIG. 49 is a bottom plan view of the gouge of FIG. 46;
FIG. 50 is a left end view of the large gouge of FIG. 48;
FIG. 51 is a right end view of the large gouge of FIG. 48;
FIG. 53 is a top plan view of the V-gouge of FIG. 52;
FIG. 54 is a side view of the V-gouge of FIG. 52;
FIG. 55 is a bottom plan view of the V-gouge of FIG. 52;
FIG. 56 is a left end view of the V-gouge of FIG. 54;
FIG. 57 is a right end view of the V-gouge of FIG. 54;
FIG. 59 is a top plan view of the scoop of FIG. 58;
FIG. 60 is a side view of the scoop of FIG. 58;
FIG. 61 is a bottom plan view of the scoop of FIG. 58;
FIG. 62 is a left end view of the scoop of FIG. 60;
FIG. 63 is a right end view of the scoop of FIG. 60;
FIG. 65 is a top plan view of the large scoop of FIG. 64;
FIG. 66 is a side view of the large scoop of FIG. 64;
FIG. 67 is a bottom plan view of the large scoop of FIG. 64;
FIG. 68 is a left end view of the large scoop of FIG. 66;
FIG. 69 is a right end view of the large scoop of FIG. 66;
FIG. 71 is a plan view of the hoe tool bit of FIG. 70;
FIG. 72 is a side view of the hoe tool bit of FIG. 70;
FIG. 73 is an end view of the hoe tool bit of FIG. 72;
FIG. 75 is a plan view of the dual slitter tool bit of FIG. 74;
FIG. 76 is a side view of the dual slitter tool bit of FIG. 74;
FIG. 77 is an end view of the dual slitter tool bit of FIG. 76;
FIG. 78 is a cross-sectional view of the dual slitter tool bit taken along line 78—78 of FIG. 76;
FIG. 80 is a plan view of the single slitter tool bit of FIG. 79;
FIG. 81 is a side view of the single slitter tool bit of FIG. 79;
FIG. 81a is a cross-sectional view of the single slitter tool bit taken along line 81a—81a of FIG. 81;
FIG. 82 is an end view of the single slitter tool bit of FIG. 81;
FIG. 83 is a perspective view of a plug puller tool bit of the present invention;
FIG. 84 is a plan view of the plug puller tool bit of FIG. 83;
FIG. 85 is a side view of the plug puller tool bit of FIG. 83;
FIG. 86 is a left end view of the plug puller tool bit of FIG. 85;
FIG. 87 is a right end view of the plug puller tool bit of FIG. 85;
FIG. 89 is a plan view of the disk drill of FIG. 88;
FIG. 90 is a side view of the disk drill of FIG. 88;
FIG. 91 is a left end view of the disk drill of FIG. 90;
FIG. 92 is a right end view of the disk drill of FIG. 90;
FIG. 94 is a plan view of the push drill of FIG. 93;
FIG. 95 is a side view of the push drill of FIG. 93;
FIG. 96 is a left end view of the push drill of FIG. 95;
FIG. 97 is a right end view of the push drill of FIG. 95;
FIG. 99 is a plan view of the trephine of FIG. 98;
FIG. 100 is a side view of the trephine of FIG. 98;

FIG. 101 is a left end view of the trephine of FIG. 100;

FIG. 102 is a right end view of the trephine of FIG. 100;

FIG. 104 is a plan view of the poly-plug puller tool bit of FIG. 103;

FIG. 105 is a side view of the poly-plug puller tool bit of FIG. 103;

FIG. 106 is a left end view of the poly-plug puller tool bit of FIG. 104;

FIG. 107 is a right end view of the poly-plug puller tool bit of FIG. 104;

DETAILED DESCRIPTION

Figures 1, 2:
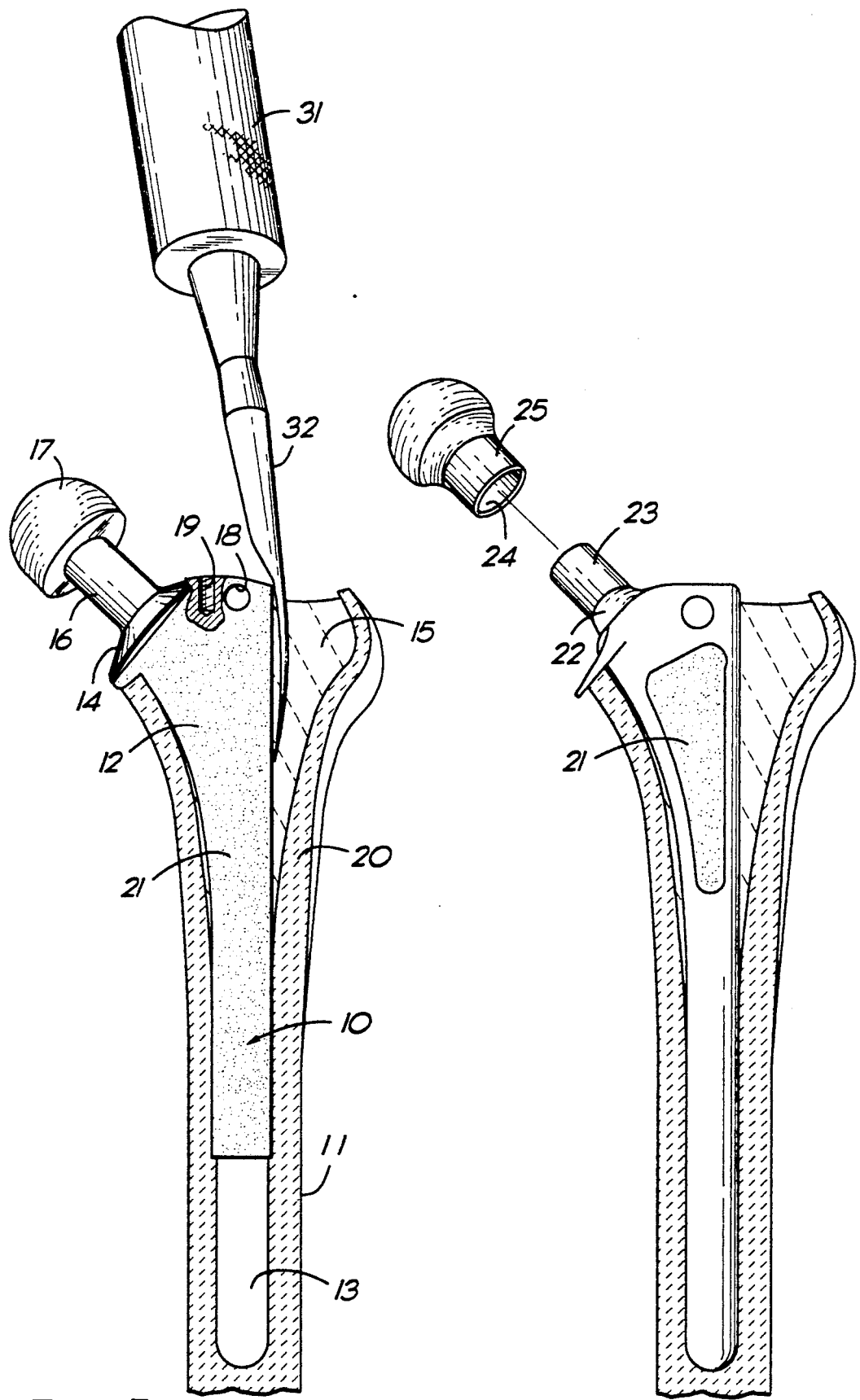
FIG. 1 is a side view partly in cross section of an exemplary femoral implant component of a hip replacement joint as implanted in a femur with an osteotome for disrupting cancellous bone.
FIG. 2 is a side view of another embodiment of a femoral component of a hip replacement joint implanted in a femur, with the head of the component exploded from the body.
Figure 2:
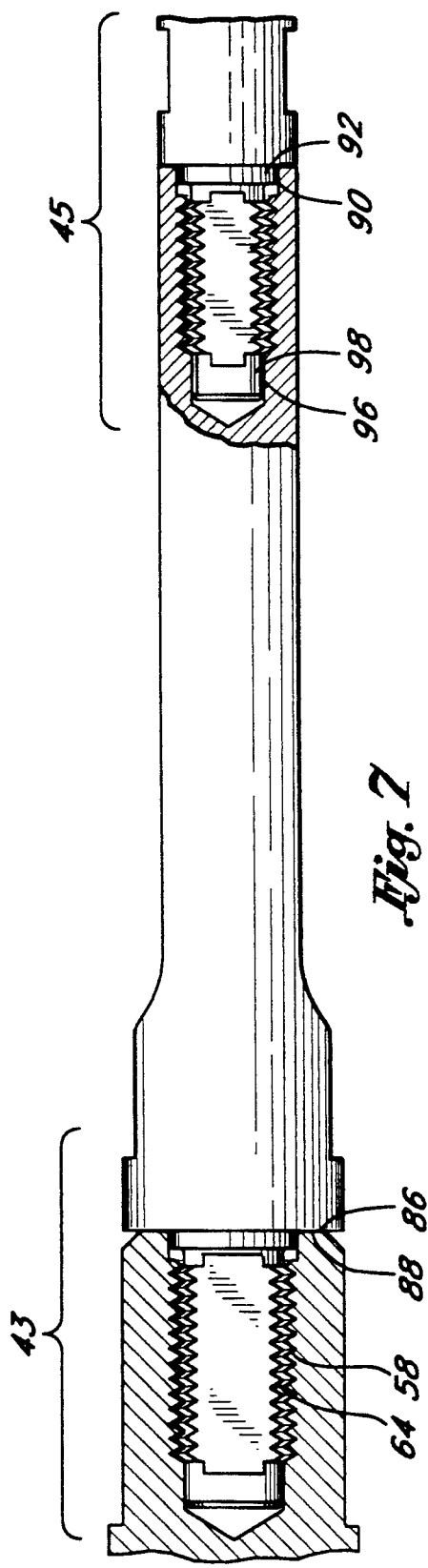

FIG. 1 illustrates an exemplary femoral component 10 of a hip prosthesis joint implanted in the end of a femur which has the trochanter osteotomized. The body 12 of the prosthesis and at least a portion of the shank 13 which extends along the medullary canal have a porous surface. Such a porous surface is provided on the prosthesis by some manufacturers in the form of metal beads having the same composition as the prosthesis which are sintered onto the solid metal of the prosthesis. Other manufacturers employ a mat of metal wires sintered onto the surface. In either type, the porous surface portion provides a substrate into which growth of cancellous bone 15 may occur for rigidly securing the prosthesis to the femur. Some prostheses have a collar 14 which bears against the cortex 20 at the end of the femur. Collarless prostheses are also used.

A neck 16 connects a ball or head 17 to the body of the prosthesis. The spherical head provides the bearing engagement with the acetabular cup (not shown) secured to the patient's pelvis.

A transverse hole 18 extends through the prosthesis for engagement by a tool for extracting the prosthesis from the femur in the event a revision is required. In addition or alternatively, a threaded hole 19 is provided in the end of the body for receiving a tool which can provide a longitudinal force for withdrawing or inserting the prosthesis.

Another type of prosthesis as illustrated in FIG. 2 has a porous surface area 21 on the body for receiving ingrowth of cancellous bone for securing the prosthesis in the medullary canal. In the illustrated embodiment, the neck 22 of the prosthesis has a self-holding taper 23 at its proximal end for receiving a complementary female taper 24 in a head 25 which can thereby be removably secured to the prosthesis. A variety of self-holding tapers with different angles of taper and standard dimensions may be used. These include the Morse, Brown and Sharpe, Jarno, Sellers, Reed, American Standard and Metric tapers. Taper angles of 5% or less are customary. Self-holding tapers cause the shank, when seated firmly in the socket, to tend to stay in place by friction due to the small taper angle. For example, when the head is driven onto a Morse-type taper with a couple of mallet blows, it cannot be removed manually. A larger longitudinal force may be used for separating a self-holding taper.

A removable head for a prosthesis provides the opportunity for stocking heads with varying lengths of neck for fitting to a variety of standard bodies for mixing and matching to fit the prosthesis to an individual patient. For example, up to ten different dimensions of body may be matched with a dozen or so different heads with varying diameters and neck lengths.

For removing a prosthesis implanted in a femur, an ultrasonic transducer 26 (FIG. 3) is coupled to the prosthesis. At the end of the transducer there is a metal sleeve 27 having a socket 28 with a female self-holding taper matching the taper on the neck of the prosthesis. The intimate engagement of the self-holding taper provides high efficiency coupling of the ultrasonic vibrations from the transducer to the prosthesis.

The ultrasonic transducer may be any of a variety of known transducers. These may include electrostrictive, magnetostrictive or electromagnetic devices, as may be preferred by the equipment manufacturer. Each of these has certain advantages depending on the frequency range, amplitude of vibration, and power level.

The ultrasonic transducer is driven by an ultrasonic signal from a conventional power supply 29. Such power supplies typically permit the user to determine the frequency of oscillation and the power level of the ultrasonic signal sent to the transducer. For purposes of disrupting cancellous bone ingrown into the porous surface of a joint prosthesis, a frequency corresponding to a resonant frequency of the prosthesis is desirable for maximizing amplitude of vibration with a given signal strength. Some tuning of frequency for a particular prostheses implanted in bone may be employed in lieu of merely increasing signal strength. It is desirable to employ a frequency in the range of from about 20,000 to 40,000 Hertz, preferably around 25,000 Hertz.

For removing the prosthesis, the transducer is coupled to the self-holding taper on the prosthesis and the prosthesis is ultrasonically vibrated by applying a signal to the transducer. The vibration of the prosthesis disrupts cancellous bone at the surface of the prosthesis due to the impedance mismatch between the metallic prosthesis and the cancellous bone surrounding it. There is a substantial impedance mismatch between the portion of the prosthesis which does not have a porous surface and the surrounding cancellous bone, such as along the length of the shank, and the bone at the interface is readily disrupted. There is less of an impedance mismatch and also less energy transfer at the interface between the porous metal surface and the bony ingrowth. A somewhat higher energy input level is therefore required for disrupting cancellous bone adjacent to the surface of the porous ingrowth area.

After applying ultrasonic vibrations for several seconds, an attempt is made to withdraw the prosthesis. If the transducer is in the way, it may be removed before trying to withdraw the prosthesis to avoid damaging the transducer. In the event the prosthesis is not readily removed by application of pressure or moderate impact, the ultrasonic signal strength can be increased to try again to see if there has been adequate disruption of the cancellous bone at the interface with the porous surface.

Alternatively, the disruption of cancellous bone by the ultrasonic vibrations may be investigated by probing with a thin instrument passed along the body adjacent to the porous surface before an attempt is made to withdraw the prosthesis.

Some prostheses, such as the one illustrated in FIG. 1, have a head integral with the body rather than being connected thereto by a self-holding taper. The ultrasonic transducer may be coupled to such a prosthesis by way of a threaded hole, or a spherical socket may be used to mate with the spherical head and provide good energy transfer.

An alternative technique may be employed for disrupting cancellous bone adjacent to the porous surface of the prosthesis. According to this technique an ultrasonic transducer 31 (FIG. 1) is threaded onto a conventional osteotome 32 and the osteotome is inserted along the porous ingrowth surface of the prosthesis 10 for disrupting a narrow channel of cancellous bone. By repeatedly inserting ultrasonically vibrating osteotomes along different areas of the body of the prosthesis, sufficient cancellous bone can be disrupted to free the prosthesis from the bone and permit its withdrawal with limited trauma to the patient. This technique for disrupting cancellous bone may be used in areas readily accessible at the proximal end of the prosthesis and ultrasonic vibration of the entire prosthesis may be employed for disrupting cancellous bone adjacent to the distal end of the prosthesis.

It should be noted that disruption of the bone occurs at the impedance mismatch between the metal and the bone. There is sufficiently low energy transfer through the bone and other tissues to avoid significant damage to the cancellous bone or cortex remote from the interface. Preferably the energy level is kept low enough that there is insignificant disruption of cortical bone in places where the shank of the prosthesis contacts such bone.

When removing a porous ingrowth prosthesis by ultrasonically vibrating osteotomes, equipment similar that described in the Engelbrecht patent, supra, may employed, the disclosure of which is hereby incorporated by this reference. Osteotome blades are available with male threaded ends for attachment to handles or the like. The threaded end makes a convenient place for coupling an ultrasonic transducer to the osteotome. The threaded tip of a transducer may be placed in the threaded hole 19 in a prosthesis as illustrated in FIG. 1 for efficiently coupling the ultrasonic vibrations between the transducer and the prosthesis. The way of coupling the transducer to the osteotome is not of significance and other means may be employed. Coupling to the self holding taper of a prosthesis is preferred.

It will also be noted that the power levels required when a transducer is coupled to an osteotome are considerably less than when a transducer is coupled to the prosthesis itself, since the area of the interface at which cancellous bone is being disrupted is considerably different.

A technique for removing a prosthesis by ultrasonically vibrating it may also be employed where the prosthesis has a substantially smooth surface and is secured in the bone by a cement such as polymethylmethacrylate (PMMA). In such an embodiment the PMMA remains softened and can be readily disrupted while ultrasonic vibrations are being applied. When vibrations are discontinued, the PMMA may become more rigid. It is, therefore, desirable when removing a prosthesis which is cemented in place, to apply ultrasonic vibrations and a withdrawing force simultaneously. This assures that a minimum withdrawal force is used for withdrawing the component. Again, if the prosthesis is not removed readily with a withdrawing force which may be steady or in the form of impact, the power level may be increased until a reasonable withdrawing force is sufficient for withdrawing the prosthesis from the medullary canal.

After removing the femoral stem 10, the revision procedure further requires the removal of the PMMA from the femoral canal. By energizing various specialized tool bits with ultrasonic energy, the tools easily slice through the softened PMMA and separate the PMMA from the adjacent cancellous bone 15. A variety of ultrasonic energy-activated tool bits or tips can be used during the cement removal procedure. For example, a gouge can be used to debulk cement from a proximal area, a flat osteotome can be used to separate the cement from the cancellous bone, a slitter or a hoe can be used to slice through the cement, and a cement plug modification tool, such as a plug removal tool bit 44 shown in FIG. 5, can be used to remove a cement plug at the distal end of the femoral canal.

Thus, there has been provided in accordance with another aspect of the present invention a mechanical junction for facilitating the rapid attachment and removal of any of the plurality of tool bits during the course of a surgical procedure. In addition to permitting rapid connection and disconnection within the sterile field, the junction of the present invention achieves a high, evenly distributed compressive force to optimize propagation of ultrasonic energy from the transducer to a tool bit, while maintaining a relatively small outside diameter of the ultrasonic tool.

Referring to FIG. 5, there is illustrated an ultrasonic medical tool 40 comprising an ultrasonic handpiece transducer 42 and an ultrasonic energy-activated tool bit 44 coupled to the handpiece transducer 42 via an extender 46. A first junction 43 is illustrated at the proximal end 48 of extender 46, and a second junction 45 is illustrated at the distal end 49 of extender 46. As used herein, the words proximal and distal refer to proximity to the handpiece transducer which supplies the ultrasonic energy to the tool bit.

Preferably, the location of each junction between the transducer 42 and tool bit 44 occurs at an antinode of the ultrasonic oscillation to minimize mechanical stress at the junctions. Thus, for example, junctions in an assembled tool will preferably be distanced apart by a whole number multiple of the distance $\lambda/2$, where $\lambda$ equals the wavelength for a given frequency of ultrasonic oscillation. Preferably, the junctions will be located at multiples of $\lambda/2 \pm 20\%$ along the length of the assembled instrument. It should be noted that the junction(s) can occur at the nodes of oscillation so long as the junction is designed to withstand the increased mechanical stress at the nodal position. Due to the desirability of maintaining a relatively small tool diameter, however, together with efficient propagation, it is preferred that the junctions occur precisely at or approximately at antinodal positions.

For the cement removal process, it is desirable to employ a frequency in the range of from about 10,000 to about 100,000 Hz, preferably about 20,000 to about 60,000 Hz, and most preferably around 40,000 kHz. Thus, for example, in a most preferred embodiment of the present invention, detailed infra, antinodes are spaced approximately 2.4 inches apart in a 0,260 inch diameter extender comprising the preferred titanium alloy and operated at approximately 40 kHz. It is therefore understood that the dimensions disclosed below are exemplary for the specific tool and specific ultrasound frequency employed.

The length of the tool bit 44 and the length and number of extenders 46, discussed infra, is also influenced by its intended use. For example, when working inside the femoral canal, the length of the tool 44 together with the extender(s) 46 should allow the tool 44 to be appropriately positioned within the canal, but not so long as to impair the surgeon's ability to maneuver the tool. Generally, the depth of the femoral canal in a human adult is not greater than on the order of about 20 inches.

The length of the tool 44 is also influenced by the intended operating frequency for that particular tool. For most tools, maximum longitudinal oscillation at the distal end of the tool bit 44 is desirably obtained by positioning the tip to coincide with an antinode of the ultrasonic oscillation. Thus, as discussed above, the length of the tool 44 generally will equal a whole number multiple of $\lambda/2$ for the ultrasonic frequency employed and preferably will equal $\lambda/2$. For example, in a most preferred embodiment, for use in the cement removal procedure, the tool length will equal about 2.4 or 4.8 inches for operation at 40,000 Hz.

It is preferred that the outer diameter of each surgical component match the outer diameter of the component intended to be joined immediately adjacent thereto to eliminate surface irregularities. When working in environments where liquid such as blood or saline surrounds the tool, the transmitted ultrasonics can produce cavitations at projecting surfaces. Cavitation at areas other than the tool bit tip are undesirable because of the ultrasonic energy loss and because of the erosion effect on the surgical components. Thus, it is preferred that the outside diameters of the joined components be substantially identical at their interface so as to provide a substantially uniform external dimension through each junction.

The overall diameter of the tool bit 44 or extender 46 is limited only by the environment of its intended use. For example, in replacing the femoral component 10 of a hip joint replacement, the tool bit 44 diameter is limited by the interior diameter of the femoral canal which typically ranges between about 0.25 to about 0.75 inches. Preferably, the tool bit 44 diameter is sized even smaller to allow for the concurrent insertion into the femoral canal of additional apparatus such as irrigation and aspiration tubes, as well as a fiber optic visualization system.

The overall diameter also depends upon the configuration of the tool bit 44 tip. For example, a gouge may have a wider overall cross-sectional dimension than a slitter. In general, the diameter of the tool bit at the junction is less than about ½ inch and preferably less than about ⅜ inch. More preferably, the junction diameter is about 0.260 inches.

The diameter of the tool bit 44 along its axial length can be tailored to produce a desired longitudinal oscillation or stroke at a tool tip 51. As known in the art, by changing the diameter of the tool along its length, the amplitude of the oscillation will also change. Thus, by decreasing the tool diameter either gradually (i.e., in a Gaussian shape) or by stepped diameter, the amplitude can be adjusted to achieve a desired stroke at the tool tip 51.

Preferably, each tool bit is configured to function optimally or nominally optimally for its particular use. Decreasing the cross section of the tool increases the stroke, i.e., produces a positive gain in longitudinal oscillation. Moreover, where the tool includes stepped diameters, the location of the cross-sectional changes affect the degree of gain produced. The closer the location of the cross-sectional change to a node, the greater the gain realized. Thus, by controlling the change in cross section, the shape of the dimensional transition, and the location of the dimensional transition, a specific gain may be obtained to tailor the stroke of the tool for optimum performance.

Alternatively, the stroke of each tool bit is adjustable by controlling the power setting of the generator. For ergonomic reasons, however, it is preferred that each tool bit be tailored to operate nominally at its optimum without adjusting the generator power level.

In general, the stroke of the tool tip 51 (FIG. 5) should not be so great as to over stress the tool 44. For example, in a preferred embodiment of the present invention, with the diameter equal to 0.260 inches in a titanium alloy tool, the stroke is generally no more than about 0.004 inches peak-to-peak. It is understood, however, that the shape of tool or the tempering of the material comprising the tool can increase its ability to withstand greater stress at larger strokes. But it has been found that stroke lengths greater than about 0.008 inches peak-to-peak do not appreciably increase the effectiveness of the tool to remove cement or fashion the cancellous bone, at 40 kHz frequency.

More preferably, the longitudinal profile of the tool should be designed to produce a stroke length of from about 0.001 inches to about 0.004 inches, and most preferably a stroke length of about 0.002 inches for the majority of tool tip 51 configurations. For tool tips with relatively large surface area, the stroke is preferably larger, such as in the range of 0.002 to 0.004 inches peak-to-peak Preferably, the tool bits illustrated herein generally maintain a minimized thermal footprint. In other words, the tool bits are configured to minimize the frontal and side contact areas between the tool and the cement by including drafts or reliefs within the tool bit body. As a result, the ultrasonic energy concentrates at the working surfaces of the tool to optimize the performance of the tool. Energy dissipation by incidental contact with cement or tissue adjacent the surgical site is minimized.

Moreover, the tool bit configurations preferably minimizes the incidental dissipation of heat to adjacent tissue. The change of impedance at the interface surfaces between the tool bit and living tissue generates heat. The increased tissue temperature potentially increases the likelihood of denaturing protein in tissue and can produce localized necroses. Desirably, the configuration of the tool bits shown herein tend to reduce, if not eliminate, incidental contact with surrounding tissue, including cancellous bone.

Referring to FIG. 5, the illustrated tool bit 44 comprises a barb tip tool bit having a generally radially symmetrical body portion 70, which, preferably, is substantially cylindrical. A generally arrow-shaped opposing pair of projections 72 are positioned at the distal end of the tool bit 44 which ramp radially inwardly in the distal direction to form a sharp point. Preferably, the tool bit 44 additionally includes a second opposing pair of arrow-shaped projections 74 disposed on the proximal side of the first projections 72. The tool bit 44 additionally preferably comprises a substantially radially symmetrical distal portion 76 of reduced exterior dimension positioned between the projections 74 and the cylindrical body portion 70 to amplify the ultrasonic oscillations at the distal end of the tool bit, as known in the art and discussed above.

In use, the plug removal tool bit illustrated in FIG. 5 is inserted under ultrasonic energy into the cement plug which remains in the bottom of the femoral canal following removal of a cemented prosthesis. Softened cement flows up over the ramped surfaces and behind the barb of the energized tip, where it resolidifies upon interruption of power to the transducer. The tool may thereafter be manually retracted to pull the cement plug loose from the femoral canal.

Although FIG. 5 illustrated the tool bit 44 as being a barb tip tool bit, it is understood that other tool configurations, such as a gouge, slitter or hoe, can be used as well. For example, FIG. 14 illustrates a Poly Methyl Methacrylate modification tool 77. The disk drill tool bit 77 comprises an elongate body portion 78 and a radially outwardly extending annular flange 80 positioned at the distal end of the tool bit 77. The flange 80 is provided with a plurality of apertures 82 extending therethrough in the longitudinal direction. Preferably, the annular flange 80 is inclined radially inwardly in the distal direction to produce a substantially cone shaped working tip 83.

In use, the conical tip 83 is embedded in the cement plug under ultrasonic energy with some softened cement extruding through the apertures 82. The tool is mechanically withdrawn from the canal to extract the cement extruded through the apparatus. Preferably, the apertures 82 are sized and positioned to optimize the extraction of the cement, while at the same time retaining sufficient structural integrity to withstand the combination of ultrasonic energy and physical manipulation by the clinician. Generally, the tool comprises from about 4 to about 20 apertures 82 evenly spaced about the circumference of the conical tip 80. Preferably, about six to about ten apertures are provided.

It is also preferred that the body 78 have one or more diameter reductions 84 to amplify the ultrasonic oscillations at the distal end of the tool, as discussed above.

Figure 15:
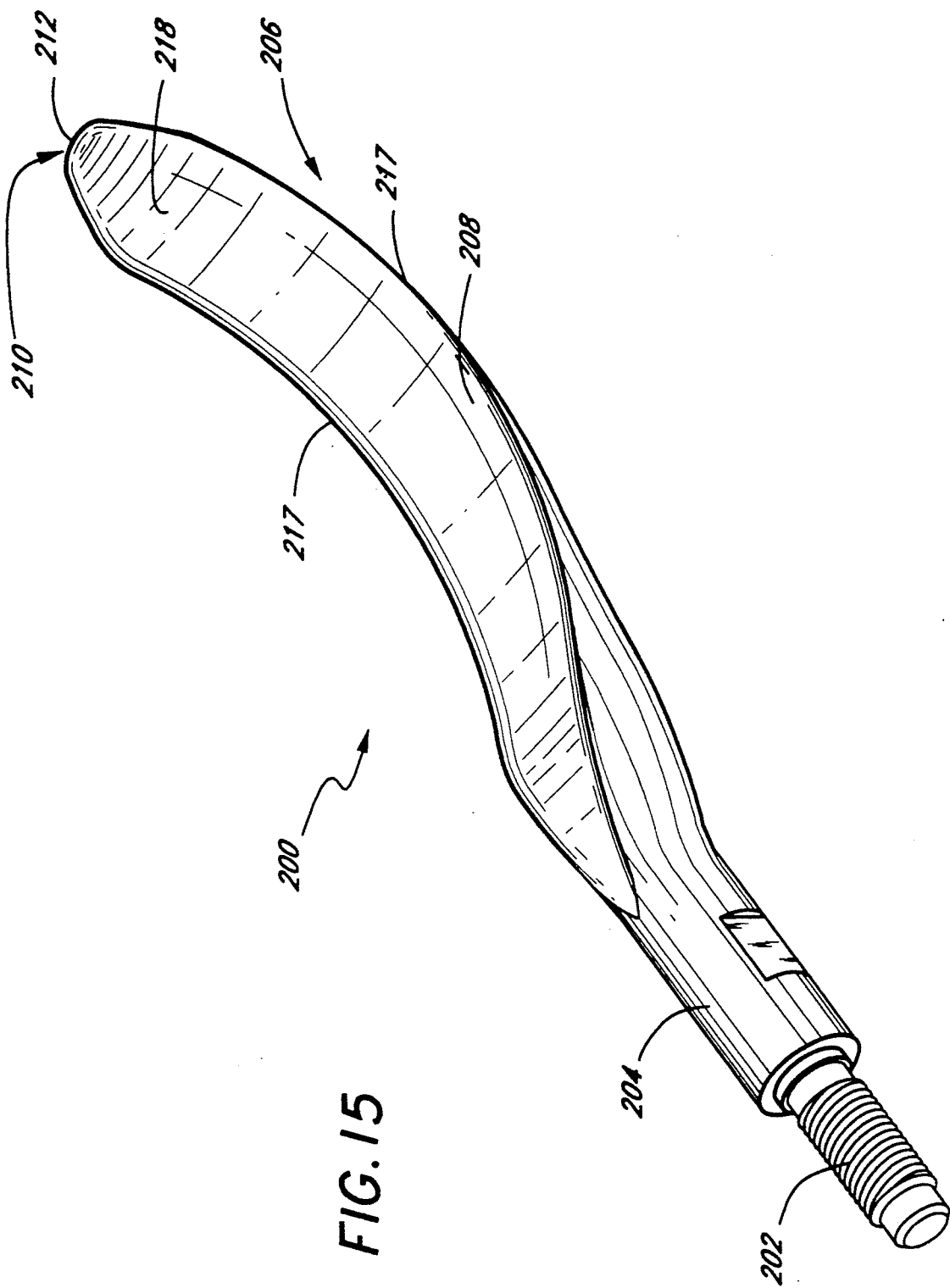
FIG. 15 is a perspective view of the acetabular tool bit of the present invention.
Figure 22:
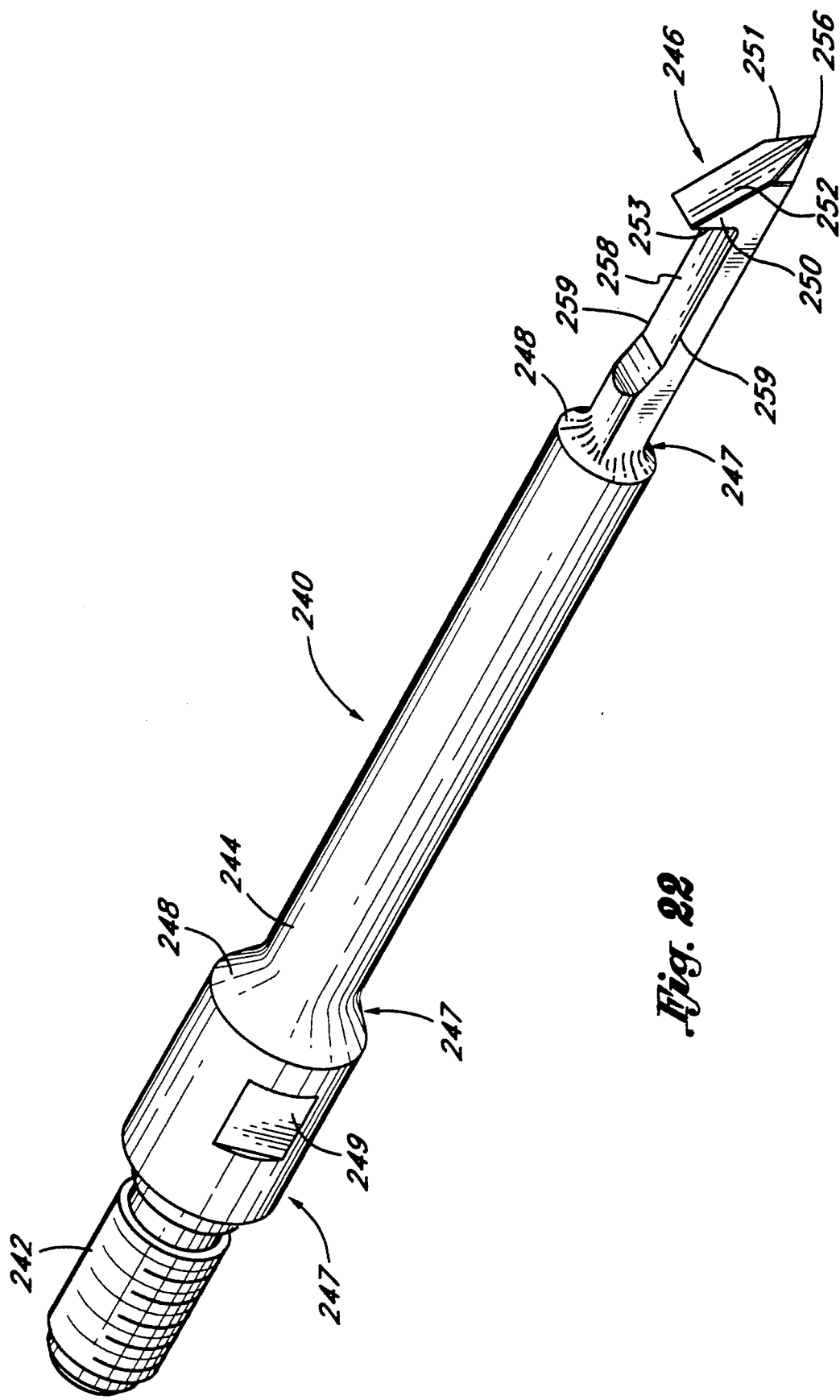
FIG. 22 is a perspective view of a barb tool bit of the present invention.

FIGS. 15 through 106 further illustrate alternative embodiments of Poly Methyl Methacrylate modification tools adapted for use with the present invention. It is contemplated, however, that those skilled in the art will appreciate that additional tool bit configurations can be designed in accordance with the teachings of the present invention.

The design of the tool bits described herein is preferably influenced by five basic design parameters to produce an optimally performing tool bit. First, the tool bits are tailored to produce a desired gain for the particular function of the tool bit in accordance with the discussion supra. Advantageously, each tool bit is designed to stroke at optimum oscillation for a set level of power. As a result, a surgeon can interchange tool bits without having to reset the power level of ultrasonic transducer every time he or she switches tool bits. Such optimization can be accomplished by routine experimentation by one of skill in the art, based upon the teachings herein.

Second, the configurations of the tool are also chosen to efficiently distribute mechanical stress throughout the tool bit and the tools are sized to provide adequate mechanical strength. Third, the configuration of each tool bit reflects the particular function performed by the tool. Fourth, the size of the tool bits are generally dictated by the environment of use, and preferably the dimensions are significantly smaller than the intended environment to permit the concurrent insertion of aspiration, irrigation and visualization equipment into the surgical site. Finally, the material of the tool bit is selected to efficiently propagate the ultrasonic energy, to be biologically compatible and to provide sufficient mechanical strength.

In addition, each tool bit, oscillating at approximately 40 kHz, provides the surgeon with both tactile and audio feedback indicating when the surgeon is cutting into cortical bone. The stokes of each tool bit have been selected to efficiently cut PMMA cement and/or cancellous bone, but resist cutting cortical bone. When the tool bits contact cortical bone, the oscillation of the tool bit against the cortical bone produces a high pitch sound, audibly indicating the contact. Consequently, the surgeon can sense both audibly and tactily the position of the tool bit relative to the surround tissue.

Although FIGS. 15 through 106 illustrate the tools as including a threaded male connector to facilitate coupling with an ultrasound transducer or waveguide (i.e., extender), it is understood that alternative connector designs, such as, for example, the spline/key-way connectors shown in FIGS. 7-9 and discussed below, may be used as well. In addition, although the preferred use of the tool bits disclosed below is in connection with cement removal from the acetabulum and femur, it is contemplated that these tool may be used equally well in connection with cement modification associated with other procedures relating, for example, to knees, shoulders, wrists, elbows and fingers.

FIGS. 15–18 illustrates an acetabular tool bit 200 comprising a connector 202, a cylindrical shank 204, and a thin arcuate cup 206. The arcuate cup 206 comprises a concave shaped surface 208 having a radius of curvature preferably generally matched to the spherical radius of the external surface of an acetabular component cemented into the acetabulum of the pelvic bone. In other words, the arcuate cup 206 has a radius of curvature, both in the longitudinal direction and in the transverse direction, generally matching the radius of curvature of the exterior surface of the generally hemispherical acetabular component, as illustrated in FIGS. 17 and 18 respectively. In a preferred embodiment, the spherical radius of curvature equals approximately 28 mm to match a conventional acetabular component for implantation into a human adult.

In the longitudinal direction, the arcuate cup 206 forms a sufficiently long arc capable of reaching around the acetabular component to break the mechanical bond at the component/cement interface generally over the exterior surface of the acetabular component. Preferably, the arcuate cup 206 has an arc length measured in the longitudinal direction ranging between 60° and 120°, and more preferably equal to about 85°.

Preferably, the arcuate cup 206 is provided with an elongate orientation which generally follows the axis of the shank 204. Stated differently, the arcuate cup is positioned to minimize the extent of offset between the longitudinal axis of the shank 204 and the concave surface 208 of the arcuate cup 206. As a result, the acetabular tool bit 200 has less tendency to whip and thus can have a thinner configuration at its distal end 210 because the mechanical stress on the arcuate cup 206 is reduced.

The distal end 210 of the acetabular tool bit 200 tapers to a relatively thin edge 212 to easily slip through the cement and get good entry into the cement behind the acetabular component. In addition, the thin edge 212 gives a minimum thermal footprint which concentrates the ultrasound energy on the cutting edges. Preferably, the arcuate cup 206 has a thickness proximate to its distal end 210 less than 0.100 inch, more preferably less than 0.050 inch, and most preferably equal to about 0.030 inch measured approximately 0.200 inch on the proximal side of the distal end 210.

The arcuate cup 206 preferably includes a draft 214 along each of its periphery edges 217 on a convex 216 surface. The drafts 214 channel the cement towards the convex surface 216 of the arcuate cup 206 when cutting through the PMMA cement. Additionally, the drafts 214 reduce the thermal footprint of the acetabular tool bit 200.

The present configuration has some tendency to whip as the ultrasound energy propagates around the curved arcuate cup 206. To compensate for the resulting mechanical stress, the thickness of the arcuate cup 206 tapers in the distal direction down to the desired tip thickness, as illustrated in FIG. 17. In the most preferred embodiment, the thickness of the arcuate cup 206 tapers from approximately 0.100 inch at its proximal side to approximately 0.030 inch at a point proximate to the distal end 210.

In order to minimize the thermal footprint of the tool, it is preferred that the acetabular tool bit 200 have a width of no more than about 20 mm, measured in the transverse direction as illustrated in FIG. 16. The width of the tool, however, should not be too narrow as to be difficult to maneuver in the cement. Preferably, the width of the tool ranges between about 6 and 16 mm and more preferably equals about 11 mm.

Viewed from the angle illustrated in FIG. 16, the distal end 210 of the acetabular tool has a narrowed, generally blunt, rounded nose 218 to facilitate insertion of the tool bit 200 and to channel the cement around the edges 217 of the tool bit 200. In addition, the generally blunt, rounded nose 218 tends to prevent the surgeon from digging into the cancellous bone by providing a surface which gives the tool a distinctly different feel when cutting from cement into the cancellous bone. Preferably, the distal end 210 further includes a radius 219 along the inner side of the blunt nose 218 to prevent the nose 218 from catching on any surface irregularities on the exterior of the acetabular component.

The acetabular tool bit 200 decreases in cross-sectional area distally to produce a desired gain in the tool, as discussed above. Preferably the tool strokes at approximately 0.001 to 0.004 inch, peak to peak, and more preferably at about 0.0025 inch.

A surgeon uses the acetabular tool bit 200 to remove the acetabular component from the acetabulum. The surgeon inserts the distal end 210 of the tool in the cement layer behind the acetabular component and follows the radius around until the surgeon has generally inserted the entire arcuate cup 206 of the acetabular tool bit 200. If the acetabular component is metal, the component will "sing" as the tool skims between the component/cement interface. The surgeon works around the entire circumference of the acetabular component by inserting and retracting the acetabular tool bit 200. Preferably, the surgeon leads the tool bit 200 with the blunt nose 218 as opposed to the longitudinal edges 217 of the tool bit 200. The surgeon continues the procedure until the completely breaking the mechanical bond between the acetabular component and the cement. The surgeon can then "pop" the acetabular component out of the pelvic bone with minimum trauma.

FIGS. 19-21 illustrate a short osteotome 220 comprising a connector 222, a generally cylindrical shank 224 and a thin flat blade 226. The shank 224 has a generally circular cross section which tapers distally on two opposing sides of the tool from a transition point 228 to the flat blade 226, as best seen in FIG. 21. This configuration tailors the gain of the tool to produce the desired stroke of approximately 0.0015 inch, enhances mechanical strength, and provides symmetric ultrasonic wave propagation along the length of the tool. Preferably, two substantially flat surfaces 230 ramping proximally from the flat blade 226 on opposite sides of the tool form the generally constant taper of the shank 224, as shown in FIGS. 19 and 21. This configuration provides adequate mechanical strength to allow the surgeon to use the osteotome 220 in a variety of ways.

As shown in FIG. 20, the blade 226 flares outwardly relative to the shank 224. The blade 226 has a substantially rectangular shape with sharpened edges 232 around it periphery. Although the preferred use of the tool requires cutting by only a distal end 234 of the tool, the longitudinal sides 236 of the blade are preferably sharpened to make the osteotome 220 more versatile.

Preferably, the distal end 232 of the blade includes rounded corners 238 having a radius that matches, or more preferably is less than, the spherical radius of the acetabular component. The rounded corners 238 allow a surgeon to smoothly draw the distal end 234 of the blade 226 sideways within the acetabulum. In addition, the rounded corners tend to prevent the surgeon from unintentionally cutting into the cancellous bone. Sharp corners provide little or no tactile response when the surgeon starts to cut into the cancellous bone. Rounded edges, on the other hand, provide a tool surface instead of a point, and the surgeon tactily recognizes when the blade 226 begins to penetrate into the cancellous bone.

The blade 226 has a width at the distal end 234 sufficient to efficiently cut the cement remaining in the acetabulum and to easily maneuver within the cavity. Preferably the blade 226 width ranges between about 6 and 12 mm, and more preferably equals about 9.5 mm wide at the distal end.

The blade preferably has a thickness, measured in the transverse direction of FIG. 21, sufficient to produce a slot in the cement severing the cement sheet while maintaining a minimized thermal footprint. Preferably, the blade has a thickness ranging between 0.020 and 0.060 inch, and more preferably equals about 0.040.

After removing the acetabular component with the acetabular tool bit 200 and debulking the cement mantle with gouges or scoops, the surgeon removes the remaining cement in the acetabulum by using the short osteotome 220. The surgeon cuts the remaining, concave, generally hemispherical cement layer into several pie-shape wedges with the distal end 234 of the short osteotome 220 and subsequently pries each cement wedge away from the cancellous bone.

FIGS. 22-27 illustrate a barb tool bit 240 used to extract cement plugs anchoring an acetabular component into the acetabulum. The barb tool bit 240 comprises a connector 242, an elongated, cylindrical shank 244, and a barb 246.

The elongated, cylindrical shank 244 preferably includes at least one step concentrator 247 (i.e., a step in its diameter) to tailor the gain of the barb tool bit 240 to function optimally; i.e., to preferably stroke at approximately 0.001 to 0.004 inch, peak to peak, and more preferably at about 0.0015 inch, peak to peak at 40 kHz. Because the barb tool bit 240 only requires a gain sufficient to produce a stroke of about 0.002 inch, the step concentrator 247 can be located closer to antinodes to reduce the stress at the location of the step and to reduce the overall gain of the tool bit 240. In addition, the longitudinal profile as illustrated in FIGS. 23-25, is preferably designed to improve visualization, irrigation and aspiration by decreasing the diameter of the tool along its length. The reduced cross-section further allows the barb tool bit 240 to insert into tighter areas. Fillets 248 blend together the diameter steps 247 to improve the mechanical strength of the tool bit 240 at the transition locations.

In a most preferred embodiment, the shank 244 has a diameter at a proximal end 247 equal to about 0.260 inch and steps down to a diameter of approximately 0.150 inch on the distal side of the wrenching flats. Proximate to a distal end 251 of the barb tool bit 240, the shank 244 preferably includes a second step 247 in diameter down to approximately a 0.100 diameter.

The barb 246 comprises a generally half arrowhead-shaped projection 250 extending radially and having a surface 252 ramping radially outwardly in the proximal direction from the distal end 251 of the barb tool bit 240. The angle between the ramped surface 252 and the tool longitudinal axis facilitates the penetration of the barb 246 into the cement and provides enough area on surface 253 on the proximal side of the barb 246 to leverage the cement plug out of the pocket. Preferably, the angle ranges between 20° and 75°, more preferably ranges between 30° and 60°, and most preferably equals 45°.

The barb 246 attaches to the distal end of the shank 244, with a fillet 254 improving the strength of the juncture to compensate for the torque applied on the barb 246 during use, as will be discussed below. At the distal end 251, the barb 246 includes a sharp tip 256 to ease insertion of the barb 246 into the cement. In other words, the sharpened tip 256 allows the surgeon to mechanically position the tool bit tip at a precise location before ultrasonically energizing the bit 240. This prevents the distal end 251 of the bit 240 from skating over the surface 253 of the cement or cancellous bone.

The barb 246 preferably has a size easily insertable into small pockets of cement. The greatest cross-sectional dimension of the barb 246, in a plane transverse to the axis of the shank 244, is generally less than about 10 mm, more preferably between 2 and 6 mm, and most preferably equal to approximately 4 mm (0.150 inch). The width of the barb 246, however, should not be so small as to strip out by itself, i.e., not have enough leverage area on surface 253 on the proximal side of the barb. It is also preferred that the barb 246 has a limited length, measured along the longitudinal axis of the tool from the leverage surface to the tip 256, so that the barb 246 can be inserted into shallow pockets of cement.

On the proximal side of the barb 246, the shank preferably includes a recess 258 to receive cement flowing behind the barb 246 during use. The recess 258 also improves the leverage of the barb 246 as more cement flows behind the barb 246 and the shape edges 259 of the recess 258 tend to resist rotation of the tool bit 240 in solidified cement.

The surgeon uses the barb tool bit 240 after removing the acetabular component with the acetabular tool bit 200 and after removing the cement lining the acetabulum in the pelvic bone with a combination of gouges, scoops and osteotomes. The barb 246 facilitates removal of small pockets of cement used to anchor the acetabular component into the pelvic bone. The surgeon, with the aid of the ultrasonics, forces the barb 246 into the pocket of cement to a point completely embedding the entire barb 246. With the barb tool bit 240 still ultrasonically energized, the surgeon rotates the barb through an angle, such as 90°, to position virgin cement on the proximal side of the barb 246. After de-energizing and letting the cement cool for approximately 10 to 15 seconds, the surgeon manually (i.e., without ultrasonics) extracts the cement out of the pocket by retracting the barb tool bit 240.

FIGS. 28-33 illustrate a porous gouge 260 used to remove a porous prosthesis from a femoral canal, such as schematically illustrated in FIG. 1. The porous gouge 260 comprises a connector 262, an elongated cylindrical shank 264, and a thin arcuate blade 266. The arcuate blade 266 has a concave surface 268 extending along the length of the blade 266. Preferably the concavity of the blade 266 generally matches the curvature of a conventional porous prosthesis. In a most preferred embodiment, the concave surface 268 of the blade has a radius of approximately 0.280 inch.

The blade 266 has a length sufficient to sever the ingrown bone along the length of the prosthesis. Due to the nature of this tool, its overall length is greater than the generally half wave length of most of the tools described herein. In a most preferred embodiment the blade 266 has a length of approximately 5 inches for use with a ⅓ porous coated implant and a length of approximately 7 to 8 inches for use with a 4/5 coated implant.

The blade 266 preferably has a thickness in the radial (thin) direction sufficiently thin as to not over stress the adjacent bone when inserted between the implant and the cancellous bone (i.e., act as a wedge). Preferably, the blade 266 has a thickness less than 0.100 inch, and more preferably equal to about 0.040 inch.

The blade 266 has a width in the transverse direction sufficient to provide adequate mechanical strength for the thin blade 266 to be rigid at a 0.004 inch peak-to-peak stroke, but still be flexible. Preferably, the blade width equal about 5-11 mm., and more preferably equals 7 mm.

To reduce the thermal footprint of the tool and produce a uniform thickness in the blade 266, it is preferred that the blade include a convex surface 220 opposite the concave surface 268, having a curvature generally matching that of the concave surface 268. In addition, a distal end 272 of the tool includes a radius 274 to reduce the thermal footprint and concentrate the energy at the resulting sharp edge 276.

The arcuate blade 266 connects to the shank 264 proximate to the wrench flats 278. The tool gets most of its gain from the dramatic change in cross-section which occurs close to a node at a proximal end 277. To cut the cancellous and cortical bone ingrowth, the desired gain produces a stroke of about 0.003 to 0.005 inch.

To assist the mechanical action of the ultrasonics in severing the mechanical bond at the implant/bone interface, it is preferred that the distal end 272 of the blade have a roughened surface 279 to enhance cavitation. Sufficient cavitation generally doubles the effectiveness of the tool's ability to cut through the bone. When the cavitation bubbles implode, thousands of pounds of energy releases at the interface of the implosion, destroying the immediate tissue structure. Preferably, the surface roughness ranges between 20 and 100 microns, and extends about 0.25 to 0.50 inch from the distal end 272 of the blade 266 in the proximal direction, as schematically illustrated in FIGS. 28, 29 and 31. In addition, use of the gouge 260 at lower frequency, such as, for example, 20 kHz, will substantially increase the energy in the cavitation bubbles and the effective emulsification.

The distal end 272 of the blade 266 can also include scallops 275 along the edges 273 to assist in cutting bone when working the tool sideways in a manner similar to a sawing action.

In use, the surgeon inserts the porous gouge 260 at the interface between the cancellous bone and the implant. The surgeon continues to apply a force in the distal direction until the surgeon has fully inserted the gouge 260. At this point, the surgeon works the gauge 260 back and forth, and a little bit sideways, to cut through the cancellous bone and cortical bone that is ingrown into the curved porous surface of the prosthesis implant.

Figure 34:
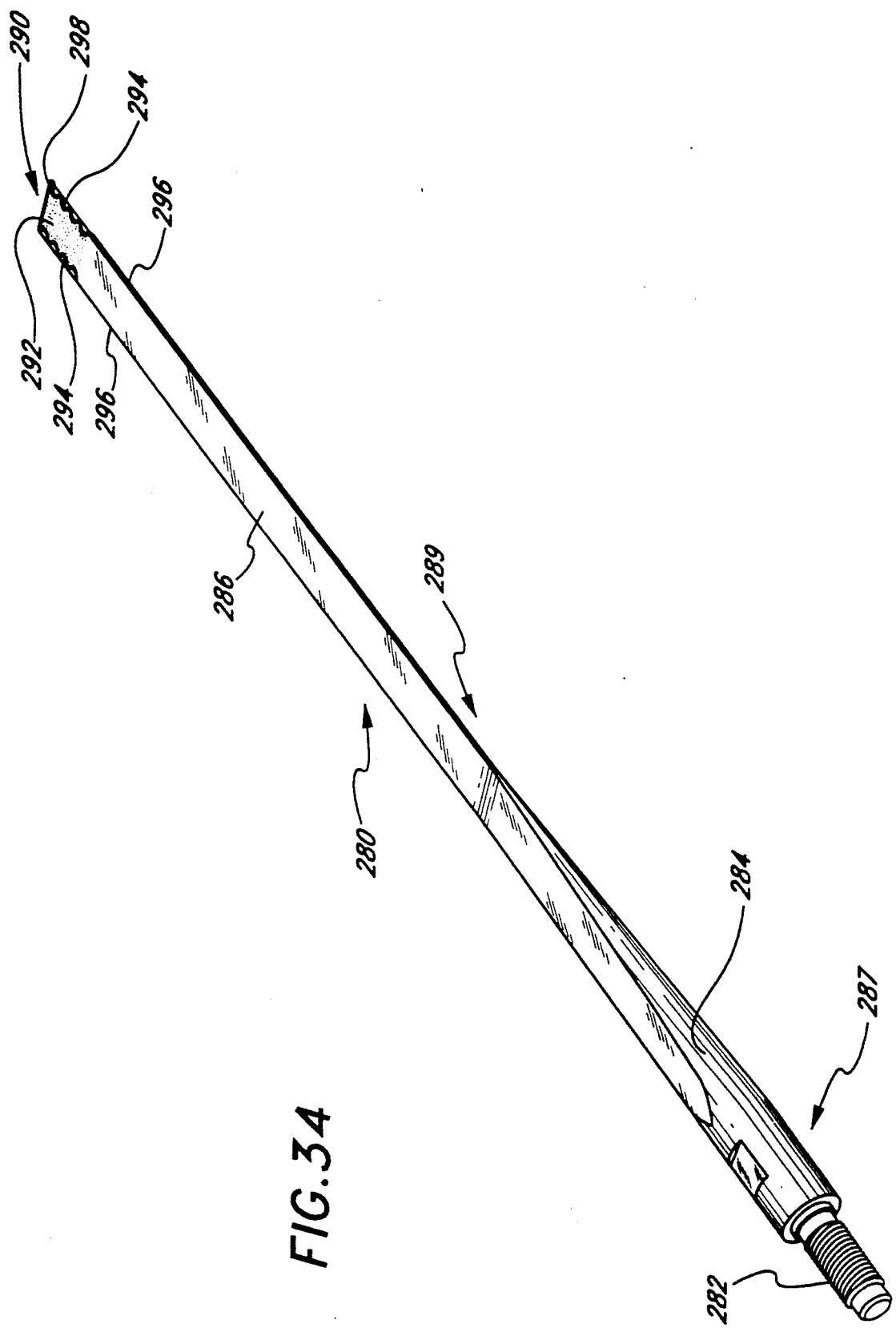
FIG. 34 is a perspective view of a long osteotome of the present invention.

The surgeon uses a long, flat osteotome 280 to sever the ingrown bone along the flat sides of the porous prosthesis. FIGS. 34–36 illustrate such a long osteotome 280 comprising a connector 282, a generally cylindrical shank 284 and a thin flat blade 286.

Referring to FIG. 34, the shank 284 has a generally circular cross section at a proximal end 287 which tapers distally from two opposing sides of the tool into the flat blade 286. This configuration tailors the gain of the tool to produce the desired stroke of approximately 0,004 inch, peak to peak, provides adequate mechanical strength, and provides symmetric ultrasonic wave propagation along the length of the tool. Preferably, two substantially flat surfaces 288 ramping proximally from the flat blade 286 on opposite sides of the tool form the generally constant taper of the shank 284, as shown in FIGS. 34 and 36.

The flat blade 286 connects to the distal end 289 of the shank 284 and extends for a sufficient length to enable the osteotome 280 to slip between the interface of the porous prosthesis surface and the cancellous bone. Due to the nature of this tool, its overall length is greater than the half wave length of most of the tools described herein. In a most preferred embodiment the blade 286 has a length of approximately 5 inches for use with a ⅜ porous coated implant. For a 4/5 coated implant, the length is about 7 to 8 inches. The latter embodiment can include an insulation coating on the proximal portion of the blade to lessen heat generation along the length of the blade by minimizing sound transfer and frictional heat.

The blade 286 preferably has a thickness in the radial direction sufficiently thin as to not over stress the adjacent bone when inserted between the implant and the cancellous bone (i.e., act as a wedge). Preferably, the blade has a thickness less than 0.100 inch, and more preferably equal to about 0.040 inch.

The blade 286 has a width sufficient to provide adequate mechanical strength for the thin blade 286 to be rigid at a 0.004 inch, peak-to-peak, stroke, but still be flexible. Preferably, the blade has a width of approximately 4–10 mm, and more preferably equal to 6 mm.

At a distal end 290, the blade preferably includes a toughened surface 292 and or scallops 294 along its periphery edges 296, the importance of which has been previously discussed in relation to the porous gouge 260.

The blade 286 includes a sharpened edge 298 at the distal end 290 to help the surgeon mechanically position the blade 286 prior to energizing the osteotome 280. The sharpened edge 298 also minimizes the thermal footprint to concentrate the ultrasonic energy at the edge 298 of the blade 286.

Figure 37:
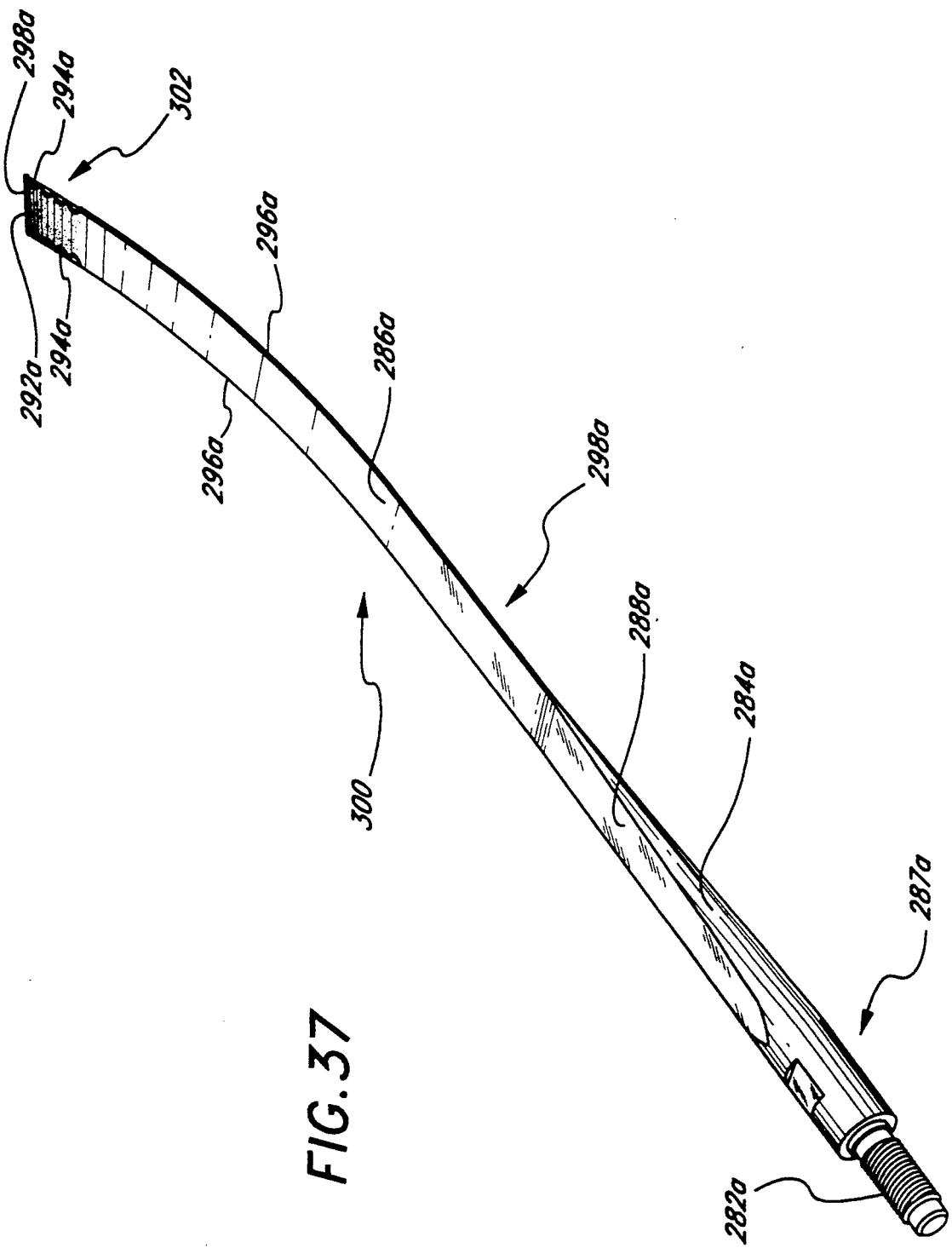
FIG. 37 is a perspective view of a long, curved osteotome of the present invention.
Figure 46:
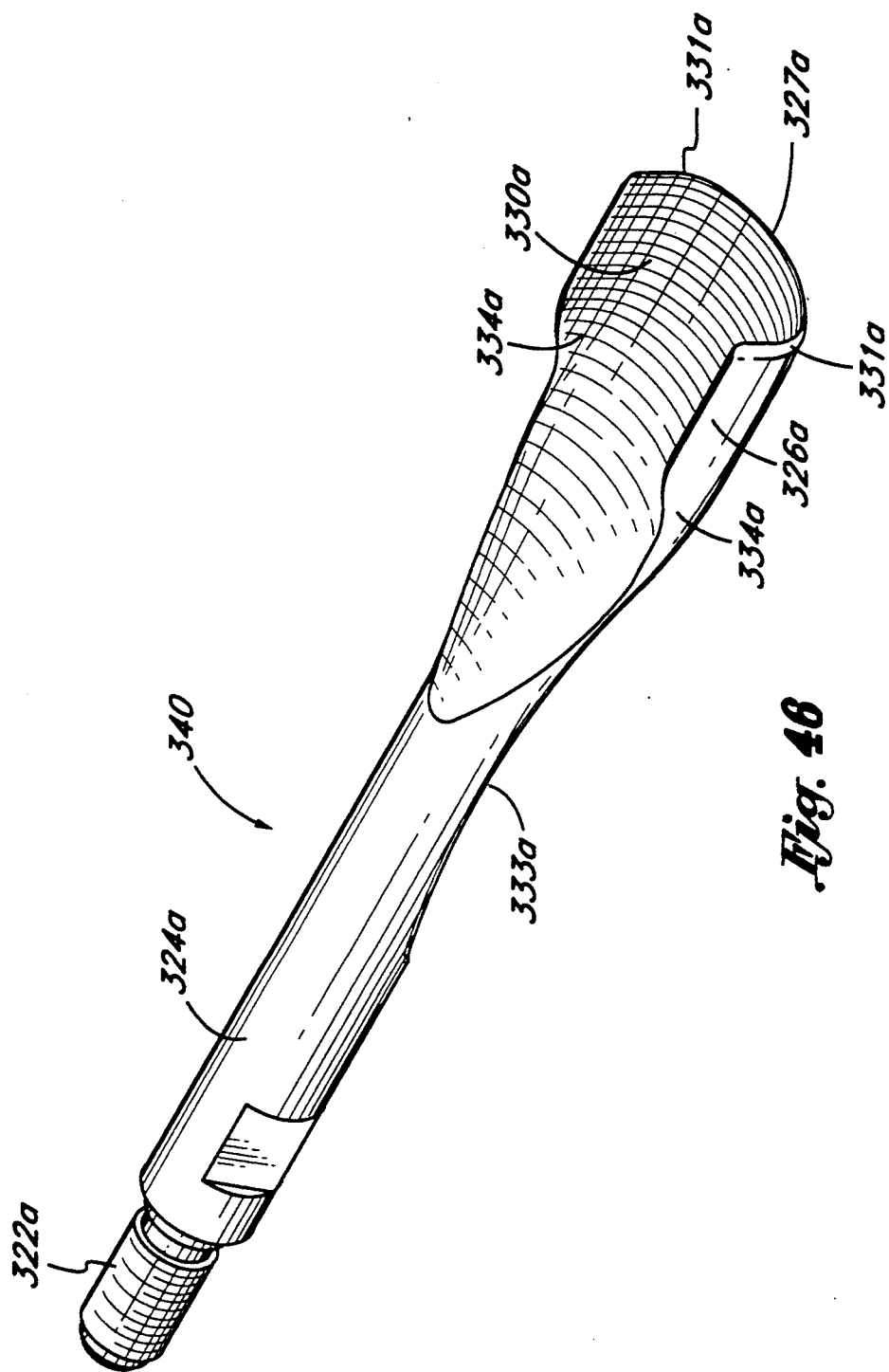
FIG. 46 is a perspective view of a large gouge of the present invention.

FIGS. 37–39 illustrate another embodiment of a long osteotome 300 having a curved end 302 for use with correspondingly configured implant surfaces. The curved osteotome 300 is configured in accordance with description of the long, flat osteotome illustrated in FIGS. 34–36. To aid in reference to the above disclosure, like numbers with an "a" suffix have been used to identify similar elements.

The surgeon uses the long, flat, flexible osteotomes 280, 300 to skinny along the flat side of the prosthesis. Preferably, the ultrasonic tool bit "sings" up against the metal implant breaking the mechanical bond between the implant prosthesis and the cancellous and cortical bone without changing the structure of the surrounding bone. Using a combination of porous gouges 260 and osteotomes 280, 300, the surgeon breaks the implant/bone interface around the entire circumference of the implant. The surgeon subsequently removes the prosthesis manually.

When working with a 4/5 porous prosthesis, the surgeon preferably makes an initial cut using the shorter of the long osteotomes 280, 300, and then use the longer blades to finish the job. If the surgeon started with the longer osteotome, the surgeon most likely will put too much force on the thin, flexible blade causing the tool bit to whip and break. By first preparing the area with the shorter osteotome, the sides of the severed implant and cancellous bone will support a portion of the blade of the longer osteotome.

After removing a cemented (PMMA) prosthesis implant, the surgeon debulks the majority of the cement mantle from the femoral canal using a combination of gouges and scoops. FIGS. 40–45 and 46–51 illustrate two embodiments of gouges 320, 340 comprising a connector 322, 322a, a generally cylindrical shank 324, 324a and a shovel-nosed tip, respectively. The following description is applicable to both of the illustrated embodiments, except where indicated to the contrary. Where appropriate, like numbers with an "a" suffix have been used to indicate like features of the two embodiments for ease of understanding.

The shovel-nose tip 326, 326a has a generally semicircular cross section at a distal end 327, 327a having a radius less than the radius of the femoral canal to protect against the edges of the shovel-nose tip 326, 326a from digging into the cancellous bone adjacent to the cement. Preferably, the dimension across the shovel-nose tip 326, 326a in the transverse direction, as illustrated in FIGS. 41 and 47, ranges between 5 and 22 mm, and more preferably equals either 8, 10, 13, 16 or 19 mm. FIGS. 40–45 illustrate a preferred embodiment of the gouge 320 having a shank 324 cross-sectional dimension equal to about 0.260 inch and a shovel-nose tip 326 cross-sectional dimension equal to about 8 mm. FIGS. 46–51 illustrate another preferred embodiment of a gouge 340 having a shank crosssectional dimension equal to about 0.260 inch and a shovelnose tip 326a cross-sectional dimension equal about 16 mm.

As best illustrated in FIGS. 40–41 and 46–47, the shovel-nose tip 326, 326a includes an arcuate channel 330, 330a extending from the distal end 327, 327a towards the shank 324, 324a in a generally uniform conical taper. The radius of curvature of the arcuate channel 330, 330a decrease linearly in the proximal direction such that the arcuate channel 330, 330a inclines by an angle α (a rake angle) with respect to the longitudinal axis of the gouge 320, 340. The rake angle α is preferably sufficient to separate the cement cut away from the cement mantle from the cement wall. The angle α preferably ranges between 3° and 45°, more preferably ranges between 7° and 15°, and most preferable equals about 10° or 11°. FIGS. 41 and 47 illustrate the generally conical section shape of the arcuate channel 330, 330a, decreasing linearly in the transverse dimension in the proximal direction.

Referring to FIGS. 42 and 48, the distal end 327, 327a of the shovel-nose tip 326, 326a has a thin, generally sharp cutting edge 331, 331a to concentrate the ultrasonic energy at the distal end 327 of the gouge 320, 340.

On the side of the shovel-nose tip 326, 326a opposite from the arcuate channel 330, 330a, the shovel-nose tip 326, 326a includes a generally flat surface disposed proximate to the distal end 327, 327a. In use, the flat surface 332, 332a allows the shovel-nose tip 326, 326a to skate along the cement layer, without uncontrollably diving or rising through the cement mantle. The gouge 320, 340 also includes a concave draft 333, 333a on the proximate side of the flat surface 332, 332a to provide a relief on the proximal side of the shovel-nose tip distal end 327, 327a. The draft 333, 333a minimizes the thermal footprint of the gouge 320, 340 by reducing the amount of surface contact area between the gouge 320, 340 and the cement. In the most preferred embodiment, the draft forms an angle $\phi$ relative to the flat surface equal to about 9°.

Referring to FIGS. 41 and 47, longitudinal sides 334, 334a of the gouge 320, 340 taper in the proximal direction, coinciding with the shape of the conical section arcuate channel 330, 330a. In order to minimize the thermal footprint of the gouge 320, 340, the longitudinal sides 334, 334a of the gouge 320, 340 may includes a pair of diametrically opposite drafts 335 to reduce the cross-sectional diameter on the proximate side of the shovel-nose distal end 327. In the preferred embodiment illustrated in FIGS. 41 and 43, the drafts 335 are angled from the longitudinal axis by approximately 4° and extend from the distal end 327 for about 0.80 inch before tapering in the transverse direction out to the cross-sectional dimension of the shank 324. In other embodiments of the gouge 340, where the cross-sectional diameter of the distal end 327a is about 0,100 inch or greater than the cross-sectional dimension of the shank 324a, the configuration of the longitudinal edges 334a taper back to the shank 324a at a sufficiently large draft angle, not requiring further drafting.

The gouge 320, 340 decreases in cross-sectional area distally to produce a desired gain in the tool, as discussed above. Preferably the tool strokes at approximately 0.001 to 0,004 inch, peak to peak, and more preferably at about 0.0015 inch, peak-to-peak.

The shovel-nose tip 330, 330a preferably has thickness, measured in the transverse direction, sufficiently thin to produce the desired gain, but thick enough to provide adequate mechanical strength. Preferably, the shovel-nose tip 330, 330a has a thickness ranging between 0,020 inch and 0.100 inch, and more preferably equal to 0.032 inch.

A surgeon may use the gouge 320, 340 to debulk the majority of the cement comprising the cement mantle circumscribing the femoral canal. Working proximal to distal, the surgeon scoops out the cement. Smaller size gouges 320, such as an 8 mm gouge, may also be use to remove cement from the cement bone interface.

FIGS. 52-57 illustrate another embodiment of a gouge, specifically a "v-gouge" 360. The v-gouge 360 comprises a connector 362, a shank 364 and a shovel-nose tip 366 having a "V" shape in transverse cross-section. As a result of its shape, the v-gouge 360 tends to have a smaller thermal footprint than the gouges discussed above.

The shovel-nose tip 366 includes a channel 367 having a generally pyramidal sectional shape which tapers in depth from shallow at the proximal end to deep at the distal end. The degree of taper preferably ranges between 2° and 45°, and more preferably equals about 9°. The pyramidal sectional shape of the channel 367 provides a smooth cross-sectional transition for an even distribution of stress and improved mechanical strength. In addition, the pyramidal sectional shape of the channel 367 improves maneuverability of the tool. Because the proximal end 368 of the gouge has a narrower width than a distal end 369, the surgeon can laterally move the proximal end 368 of the tool within the trough cut by the distal end 369 to guide the distal end 369 moving in the distal direction.

As best illustrated in FIG. 56, the channel 367 has a generally "v" shape in transverse cross-section. At the distal end of the v-gouge, an angle $\theta$ is formed between opposite walls 370 of the channel 367. Preferably, angle $\theta$ equals about 70° to 110°, and more preferably equals about 90°.

The v-gouge 360, similar to the gouges discussed above, minimizes the thermal footprint of the tool by inclining a draft 371 on its bottom side 372, as seen in FIGS. 54 and 55. The draft 371 has a generally concave shape and is positioned on the proximal side of the distal end 369 to prevent the bottom side 372 of the v-gouge 360 from dragging in the cement. In the most preferred embodiment, the draft 371 forms an angle relative to the longitudinal axis equal to about 7°.

Likewise, the longitudinal sides 373 of the shovel-nose tip 366 taper towards the shank 364 to reduce the thermal footprint of the v-gouge 360. Preferably, the longitudinal sides 373 coincides with the sides of the channel 367. The draft angle formed between the longitudinal sides and the longitudinal axis is preferably greater than 4° and more preferably equal to about 6°.

The shovel-nose tip 366 has a wall thickness between the channel wall and the longitudinal sides 373 sufficiently thick to provide adequate mechanical strength while minimizing the thermal footprint of the tool and maximizing the amount of cement being cut. Preferably, the thickness is less than 0,100 inch, more preferable less than 0.050 inch, and most preferable equal to about 0.028 inch.

It is preferred that the shovel-nose tip 366 include a flat surface 374 positioned opposite from the channel 367, as illustrated in FIG. 54. The flat surface allows the v-gouge 360 to skate along the cement without wandering up or down unless forced in those directions.

Figure 52:
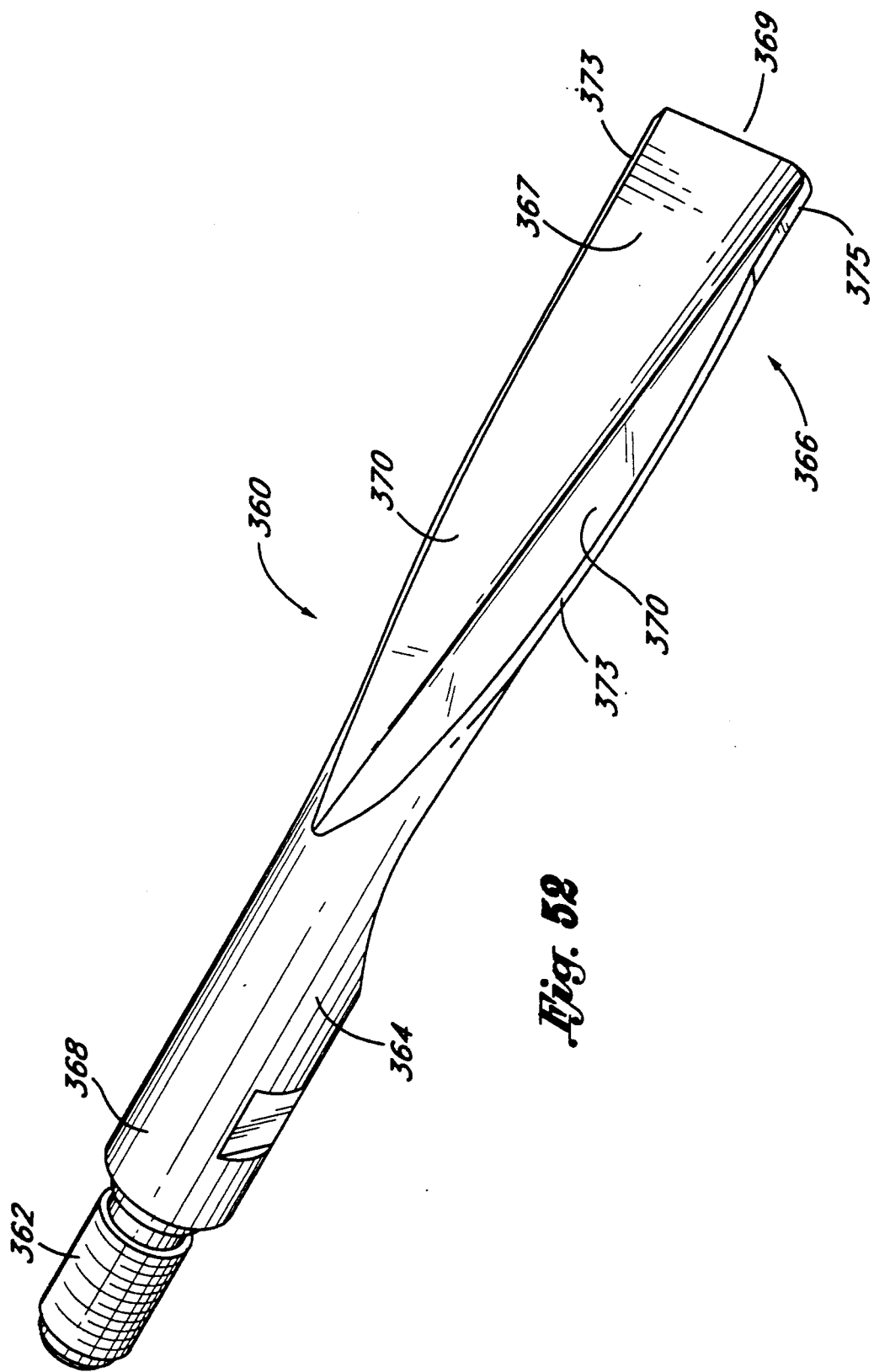
FIG. 52 is a perspective view of a V-gouge of the present invention.

Referring to FIG. 52, the shovel-nose tip 366 includes a sharp edge 375 along the distal end to facilitate cutting from proximal to distal by concentrating the ultrasound energy at the leading edge of the gouge 360.

The v-gouge 360 decreases in cross-sectional area distally to produce a desired gain in the tool, as discussed above. Preferably the tool strokes at approximately 0.001 to 0.004 inch, peak-to-peak, and more preferably at about 0.0015 inch, peak-to-peak. The shovel-nose tip 366 is preferably positioned such that the cross-sectional area change is most dramatic close to the node so that the gain is even greater than if the change is made closer to an antinode.

The surgeon can use the v-gouge 360 in at least two different ways. The surgeon can use the v-gouge 360 to cut a groove in the cement cylinder from proximal to distal or can rotate the v-gouge 360 through an angle, for example 45°, and use the v-gouge 360 as a traditional gouge for debulking or separating/splitting purposes.

FIGS. 58-63 and 64-69 illustrate two embodiments of scoops 380, 400, each comprising a connector 382, 382a, a shank 384, 384a, and a shovel-nose tip 386, 386a. The following description is applicable to both of the illustrated embodiments, except when indicated to the contrary. Where appropriate, like numbers with an "a" suffix have been used to identify like features of the two embodiments for ease of understanding. The principal difference between the scoop and the gouge is that the shovel-nose tip of the scoop is offset from the longitudinal axis of the shank.

The shovel-nose tip 386, 386a has a generally semicircular cross section at a distal end having an exterior radius less than the radius of the femoral canal to protect against the edges of the shovel-nose tip 386, 386a from digging into the cancellous bone adjacent to the cement. Preferably, the dimension across the shovel-nose tip 386, 386a in the transverse direction, as illustrated in FIGS. 63 and 68, ranges between 5 and 22 mm, and more preferably equals either 8, 9.5, 13, 16 or 19 mm. FIGS. 59-63 illustrate a preferred embodiment of the scoop 380 having a shank 384 cross-sectional dimension equal to about 0.260 inch and a shovel-nose tip 386 cross-sectional dimension equal to about 8 mm. FIGS. 64-69 illustrate another preferred embodiment of the scoop having a shank 384a cross-sectional dimension equal to about 0.260 inch and a shovel-nose tip 386a cross-sectional dimension equal about 16 mm.

As best illustrated in FIGS. 58-59 and 64-65, the shovel-nose tip 386, 386a includes an arcuate channel 387, 387a extending from a distal end 388, 388a towards the shank 384, 384a in a generally uniform conical section taper. The radius of curvature of the arcuate channel 387, 387a decrease linearly in the proximal direction such that the arcuate channel 387, 387a inclines by an angle α (i.e., a rake angle) with respect to the longitudinal axis of the tool bit. The rake angle α is preferably sufficient to separate the cement cut away from the cement wall. The rake angle α preferably ranges between 3° and 60°, more preferably ranges between 10° and 25°, and most preferable equals about 17°.

FIGS. 59 and 65 illustrate the generally conical section shape of the arcuate channel 387, 387a, having a decreasing transverse dimension in the proximal direction.

Figure 58:
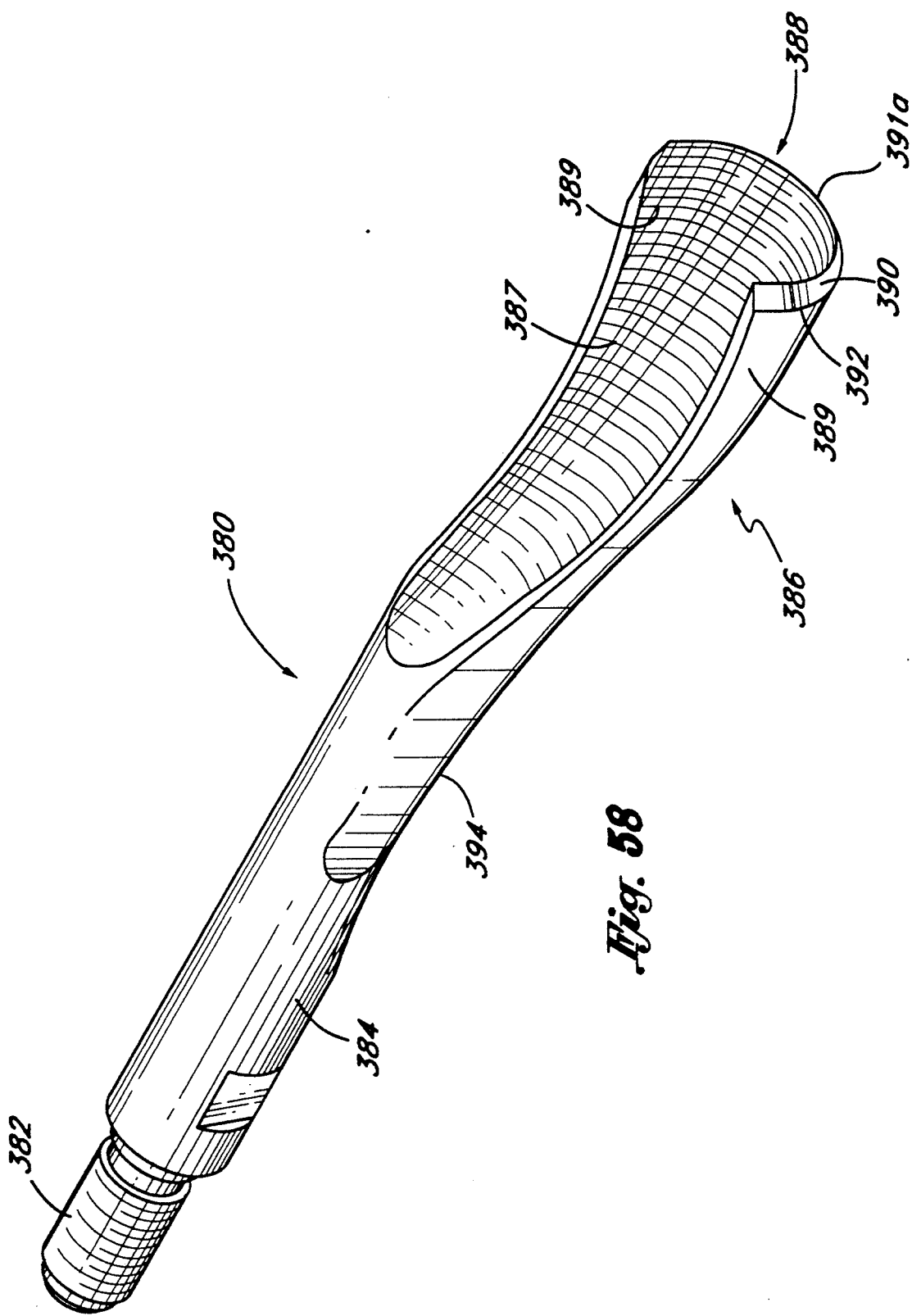
FIG. 58 is a perspective view of a scoop of the present invention.
Figure 64:
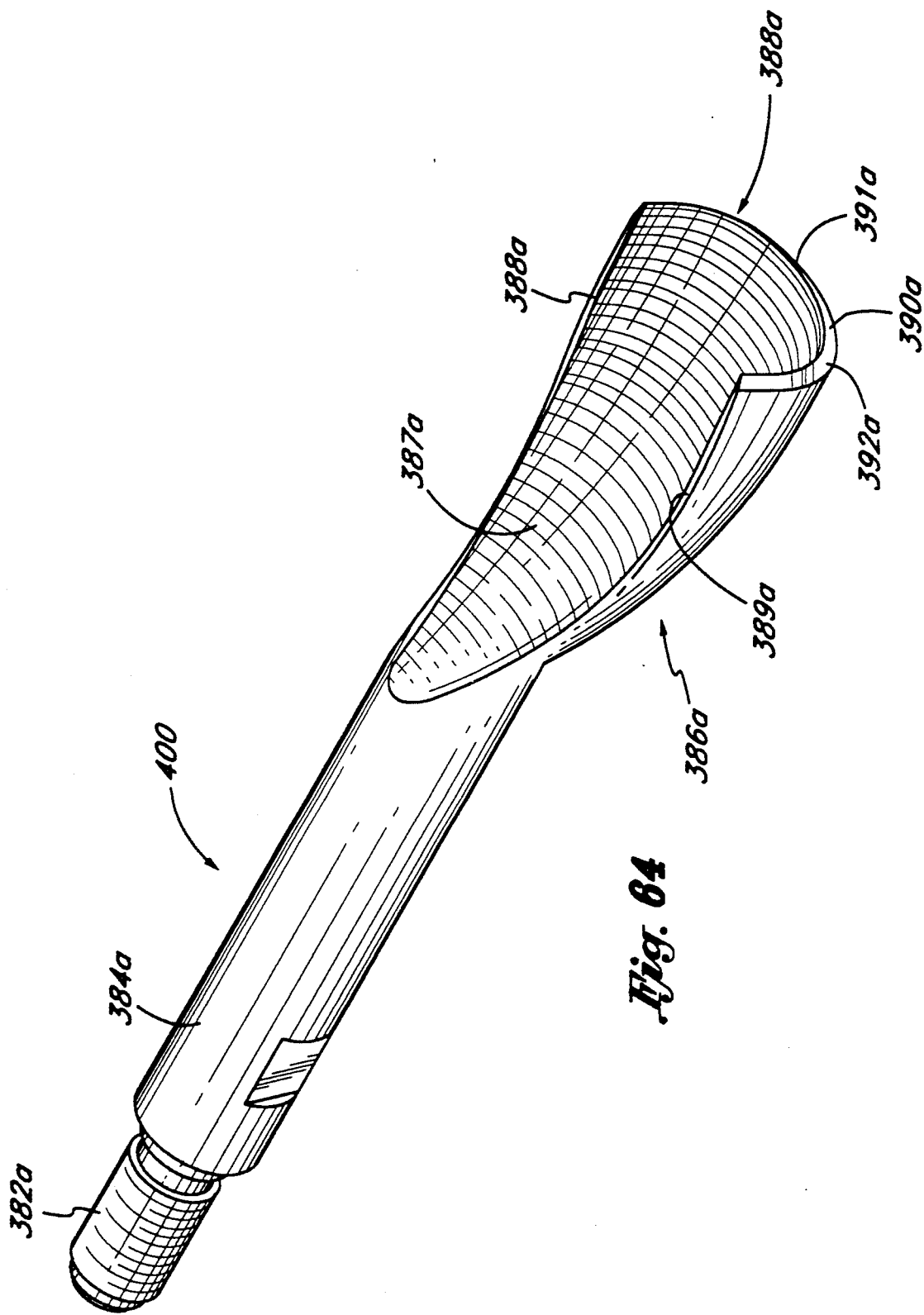
FIG. 64 is a perspective view of a large scoop of the present invention.

As seen in FIGS. 58 and 64, the arcuate channel 387, 387a includes longitudinal walls 389, 389a which are plumbed high to take a large scoop out of the cement mantle. Preferably, the walls 389, 389a extend in the transverse direction, as illustrated in FIGS. 60 and 66, from the bottom of the channel 387, 387a upwardly to a point proximate to the center-line of the shank 384, 384a.

Referring to FIGS. 60 and 66, the distal end 388, 388a of the shovel-nose tip 386, 386a has a thin, generally sharp cutting edge 390, 390a to concentrate the ultrasonic energy at the distal end 388, 388a of the tool bit.

Preferably, the cutting edge 390, 390a is positioned on an inner edge 391, 391a of the shovel-nose tip 386, 396a (i.e., at the distal end 388, 388a of the arcuate channel 387, 387a) to improve the tactile feel of the scoop 380, 400. If the cutting edge 390, 390a is positioned on the outer edge 392, 392a, the scoop 380, 380a has a greater tendency to wander and dive into the cancellous bone.

On the side of the shovel-nose tip 386, 386a opposite from the arcuate channel 387, 387a, the shovel-nose tip 386, 386a includes a generally flat surface 393, 393a disposed proximate to the distal end, as illustrated in FIGS. 60 and 66. In use, the flat surface 393, 393a allows the shovel-nose tip 386, 396a to skate along the cement layer, without wandering up or down.

In the smaller scoop 380 (i.e., the scoop having small frontal cross-sectional dimensions), the scoop includes a concave draft 394 on the proximate side of the flat surface 393 to provide a relief on the proximal side of the shovel-nose tip distal end 388, as illustrated in FIG. 60. The draft 394 minimizes the thermal footprint of the scoop 380 by reducing the amount of surface contact area between the scoop 380 and the cement. In the most preferred embodiment, the draft forms an angle $\beta$ relative to the flat surface 393 equal to about 17°. In larger embodiments of the scoop 400 (e.g., 9.5 through 19 mm wide scoops), the configuration of the shovel-nose tip bottom surface 402 tapers back to the shank at a sufficiently large draft angle, not requiring further drafting as illustrated in FIG. 66.

Referring to FIGS. 59 and 65, longitudinal sides 395, 395a of the scoop 380, 400 taper in the proximal direction, coinciding with the shape of the generally conical section arcuate channel 387, 387a. In order to minimize the thermal footprint of the smaller scoop 380, the longitudinal sides 395 of the scoop 380 may includes a pair of diametrically opposite drafts 396 to reduce the cross-sectional diameter on the proximate side of the shovel-nose distal end 388. In a preferred embodiment as illustrated in FIG. 59, the drafts 395 are angled from the longitudinal axis by approximately 5° and extend from the distal end 388 for about 0.80 inch before tapering in the transverse direction out to the cross-sectional dimension of the shank 384. In other embodiments of the scoop 400, as illustrated in FIG. 65, where the cross-sectional diameter of the distal end 388a is about 0,100 inch or greater than the shank 384a cross-sectional dimension, the configuration of the longitudinal sides 395a taper back to the shank 384a at a sufficiently large draft angle, not requiring further drafting.

The scoop 380, 400 decreases in cross-sectional area distally to produce a desired gain in the tool, as discussed above. Preferably the tool strokes at approximately 0.001 to 0.004 inch, peak to peak, and more preferably at about 0.0015 inch, peak-to-peak.

The shovel-nose tip 386, 386a has thickness, measured in the transverse direction, sufficiently thin to produce the desired gain, but thick enough to provide adequate mechanical strength. Preferably, the shovel-nose tip 386, 386athickness ranges between 0,020 and 0,100 inch, and more preferably equals about 0.032 inch.

The surgeon may use the scoop 380, 400 to debulk the cement mantle circumscribing the femoral canal, working proximal to distal. The scoop 380, 400 provides the surgeon with a tool able to stand off from the side walls of the femoral canal and to cut the cement wall without interference with the shank 384, 384a of the tool. As a result, the scoop 380, 400 improves visualization, and is particularly useful at the distal end of the canal, especially where the femoral canal has a bend. The smaller scoops 380 are designed for slitting the cement cylinder longitudinally and the larger scoops 400 are primarily designed for debulking.

Figure 70:
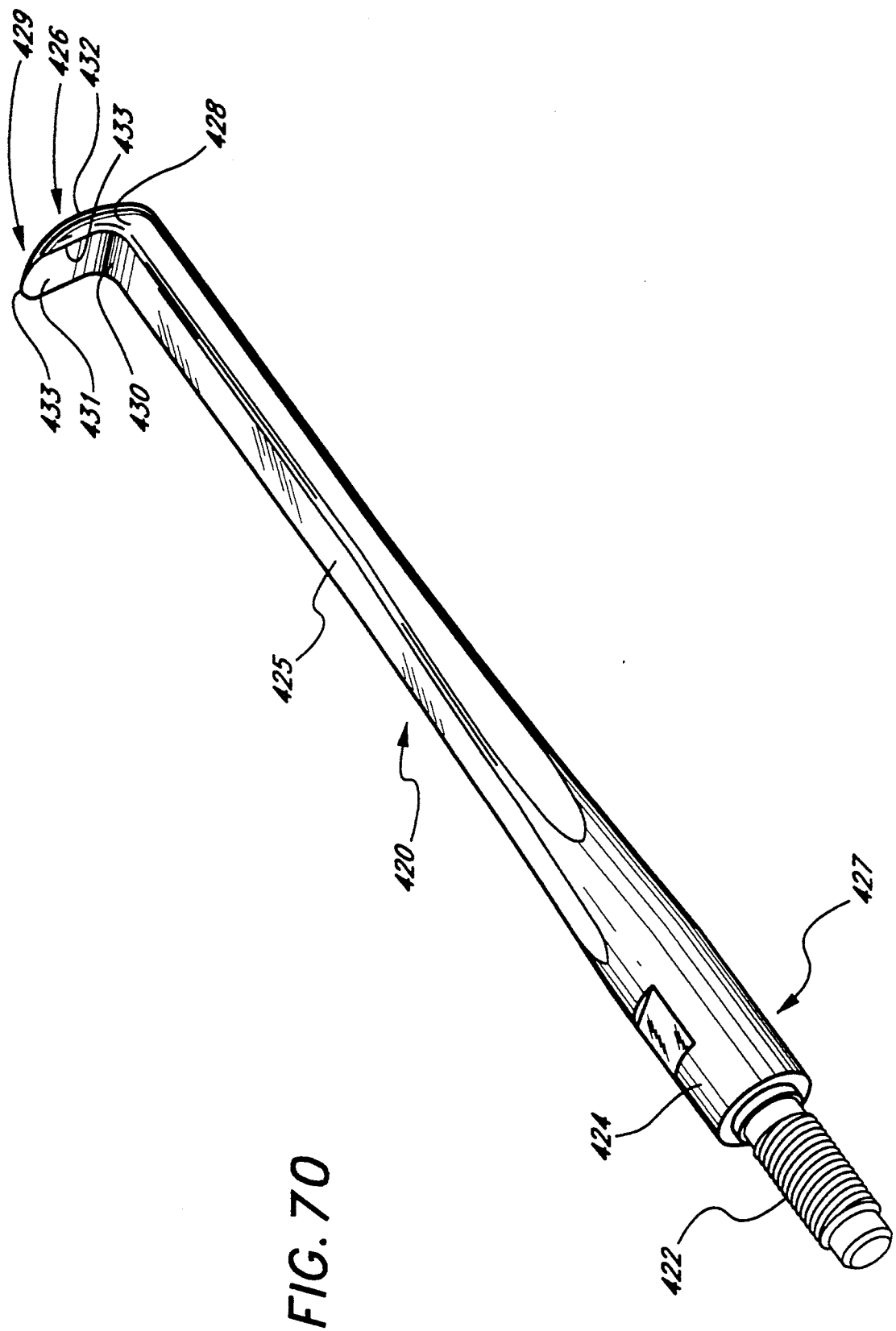
FIG. 70 is a perspective view of a hoe tool bit of the present invention.
Figure 79:
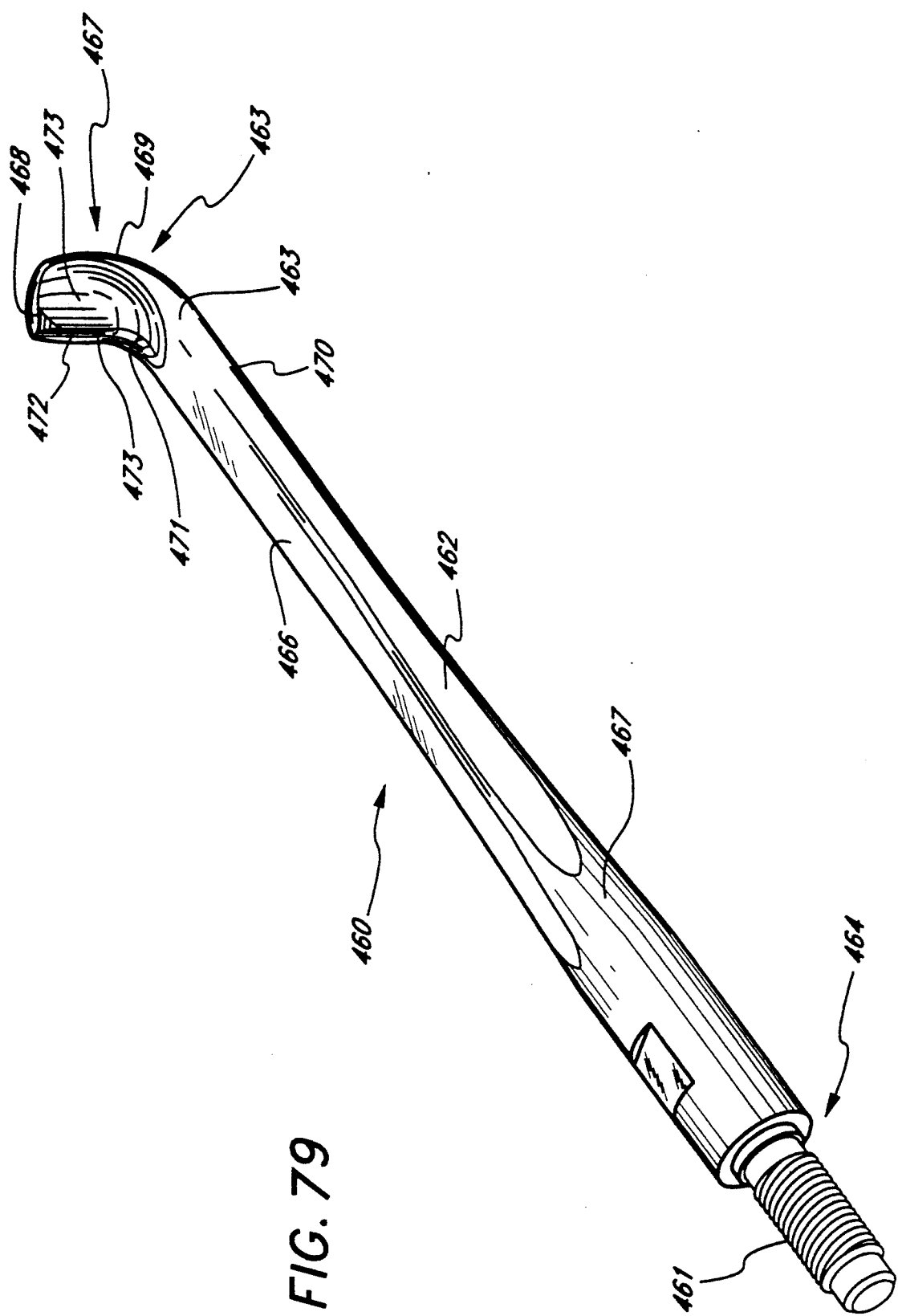
FIG. 79 is a perspective view of a single slitter tool bit of the present invention.

After the majority of the cement mantle has been removed, a thin cylinder of cement remains around the femoral canal. The surgeon may use a combination of a hoe (FIG. 70) 420, a dual slitter (FIG. 74) 440 and/or a single slitter (FIG. 79) 460 to structurally weaken the remaining cement cylinder circumscribing the wall of the femoral canal.

FIGS. 70-73 illustrate the hoe 420 comprising a connector 422, a generally cylindrical shank 424 and a blade 426. The shank 424 has a generally circular cross section at a proximal end 427 which smoothly tapers to a rectangular cross section at a base 428 of the blade 426. From the perspective illustrated in FIG. 72, the shank 424 has a generally exponential shaped profile formed by a pair of surfaces 425 disposed on diametrically opposite sides of the shank 424. The generally exponential configuration of the shank 424 tailors the gain of the shank 424 to produce the desired stroke of approximately 0.0015 inch, peak-to-peak at 40 kHz, distributes the stress along the length of the tool to provide adequate mechanical strength, and provides symmetric ultrasonic wave propagation along the length of the shank 424. In the most preferred embodiment, the shank 424 has a cross-sectional dimension equal to approximately 0.260 inch proximate to the proximal end 427 of the hoe and tapers to 0.100 inch proximate to the base 428 of the blade 426.

As illustrated FIG. 71, the shank 424 also tapers in the transverse direction along the length of the shank 424 from the proximal end 427 to the blade 426. In the most preferred embodiment, the shank 424 has width, measured in the transverse direction, proximate to the proximal end 427 of about 0.260 inch which linearly tapers to a width proximate to a distal end 429 of about 0.200 inch.

The blade 426 is formed on the distal end of the shank 424 at angle designed to use the blade 426 to cut into and separate the cement cylinder into sectional elements. Preferably the angle between the longitudinal axis and the blade 426 equals approximately 80°-100°, and more preferably equals about 90°. A fillet 430 smoothly joins a proximal surface 431 of the blade 426 with one of the shank surfaces 429 to improve the mechanical strength of the juncture. Likewise, a radius smoothly blends the opposite shank surface 429 into a distal surface 432 of the blade 426.

Referring to FIG. 72, the blade 426 includes the substantially flat proximal surface 431 and the convex distal surface 432 which blend together to form sharp edges along the top edge 434 and side edges of the proximal surface 431. Preferably, the top edge 433 is rounded having a radius equal to or less than a typical radius of the femoral canal, as best seen in FIG. 73. In the most preferred embodiment, the top edge 433 has a radius equal to approximately 0.187 inch. The convex distal surface 432 has a radius of curvature sufficient to minimize the thermal footprint of the blade 436 and to provide enough material between the surfaces 431, 432 in order for the tool to have adequate strength to resist failure when a force is applied on the blade 426 in the longitudinal direction.

The proximal surface 431 of the blade 426 has a length ranging between 1 and 10 mm and more preferably equal to about 4.5 mm. The blade 426 has a width, measured in the transverse direction as shown in FIG. 71, sufficient to provide adequate mechanical strength as the top edge 433 of the blade 426 rotates around the circumference of the femoral canal. Preferably, the width of the blade 426 is less than 20 mm, more preferably ranges between 1 and 10 mm, and most preferably equals about 5 mm (i.e., 0.200 inch). The blade 426 also has a thickness, i.e., the distance between the proximal surface 431 and distal surface 432 in the longitudinal direction, sufficient to provide adequate mechanical strength as the surgeon draws the blade 426 in the proximal direction. In the most preferred embodiment, the blade has a thickness proximate to its base approximately equal to 0.055 inch.

The surgeon uses the hoe 420 to make circumferential cuts inside the cylinder of cement mantle to separate the cylinder into sectional lengths. The surgeon inserts the tool into the femoral canal and sinks the sharp edge 433 into the cement down to the cement/bone interface. Preferably, the cement mantle has previously been debulked down to a wall thickness of approximately 2 to 3 mm. With the sharp edge of the hoe 420 at the cement/bone interface, the surgeon makes a circumferential cut to sever the cement cylinder into sectional lengths. As the hoe blade 426 rotates through the cement, the cement flows to the sides 434 of the blade 426, forming a groove down to or close to the cancellous bone. Preferably, the surgeon makes several circumferential cuts along the length of the femoral canal to produce general cylindrical segments of cement, each about 3 inches long.

The surgeon can also use the hoe 420 for retrograde cement cutting, i.e., cutting from distal to proximal, for clean up. The hoe 420 has a slight whipping action so that as the surgeon draws the hoe 420 proximally, the hoe 420 mechanically kicks up cement embedded in the interstices of cancellous bone. Therefore, it is preferred that surgeons use the dual slitter 440 and/or single slitter 460 for retrograde cement cutting.

FIGS. 74-78 illustrate the dual slitter 440. The dual slitter 440 comprises a connector 442, a shank 444 and an arcuate blade tip 446. The shank 444 has a generally circular cross section at a proximal end 447 which smoothly tapers to a rectangular cross section at a base 448 of the arcuate blade tip 446. From the perspective illustrated in FIG. 76, the shank 444 has a generally exponential shaped profile formed by a pair of surfaces 449 disposed on diametrically opposite sides of the shank 444. The generally exponential configuration of the shank 444 tailors the gain of the dual slitter 444 to produce the desired stroke of approximately 0.0015 inch, peak-to-peak at 40 kHz, distributes the stress along the length of the shank 444 to provide adequate mechanical strength, and provides symmetric ultrasonic wave propagation along the length of the shank 444. Preferably, a transition point 450 between the tapering cross-section and the proximal end 447 is located proximate to the antinode. In the most preferred embodiment, the shank 444 has a cross-sectional direction equal to approximately 0.260 inch proximate to the proximal end 447 of the dual slitter 440 and tapers to 0.100 inch proximate to the base 448 of the arcuate blade tip 446.

Figure 74:
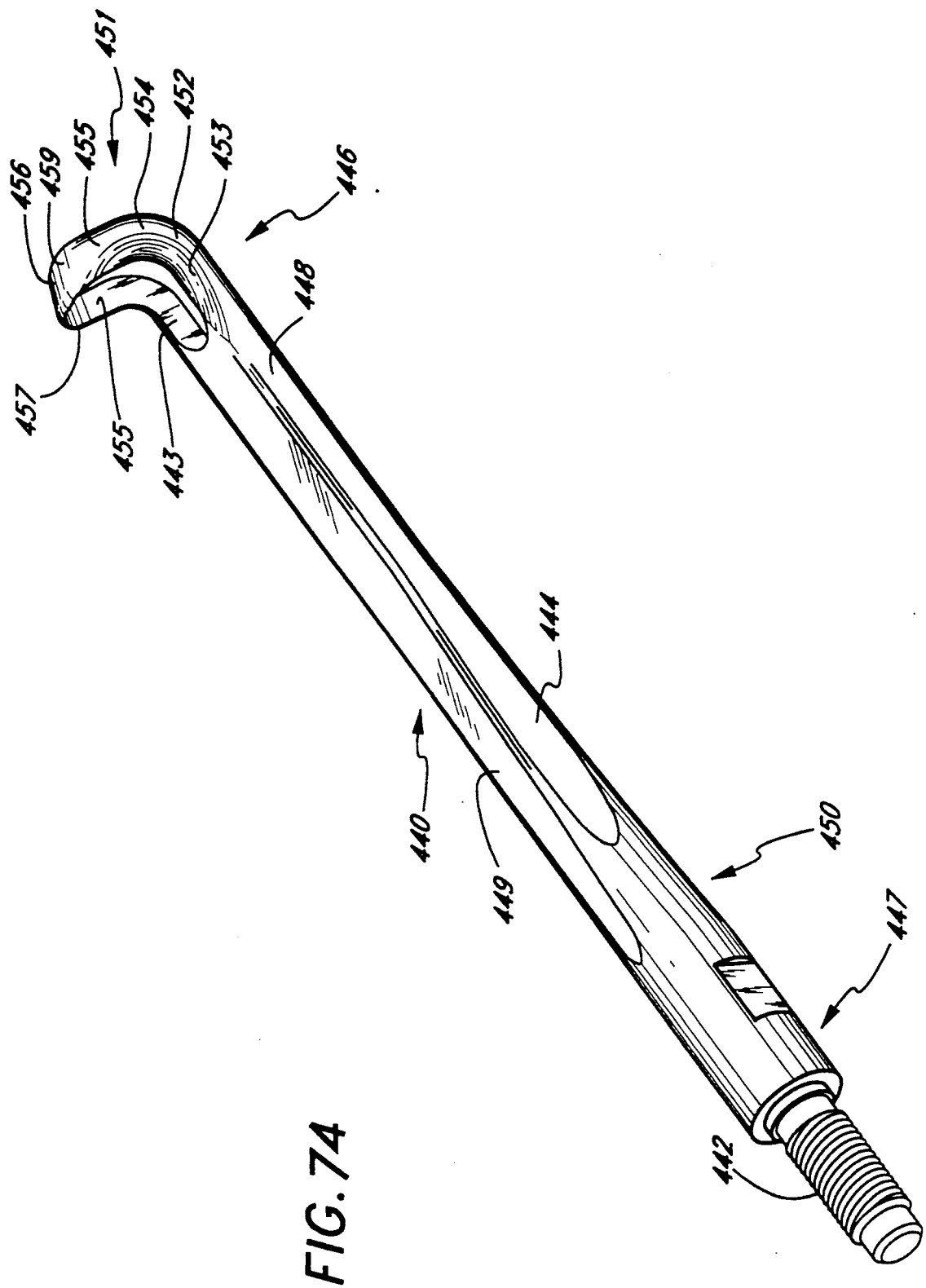
FIG. 74 is a perspective view of a dual slitter tool bit of the present invention.

The arcuate blade tip 446 is formed on distal end 451 of the shank 444 to project in the transverse direction, as illustrated in FIG. 74 at an angle of about 90° with respect to the longitudinal axis of the shank 444. Preferably, the arcuate blade tip 446 smoothly blends into the shank 444 to reduce the extent of whipping produced at a transverse end of the arcuate blade tip 446. In other words, as viewed from the perspective illustrated in FIG. 74, the arcuate blade tip 446 includes a curved transition section 452 connecting a longitudinal section 453 with a transverse section 454. The configuration illustrated in FIG. 74 whips to a small extent when ultrasonically energized, which assists in the cutting action of the tool, but not to an extent causing the tool to mechanically fail.

The transverse section 454 of the arcuate blade tip 456 has a generally inverted "U"-shaped configuration formed by a pair of generally parallel transverse sides 455 and troughing section 456. A cutting lip 457, having, a generally inserted "U"-shape configuration forms a proximal edge on the transverse sides 455 and the troughing section 456.

The troughing section includes an inner surface 458 (as shown in FIGS. 76 and 78) which extends from the cutting lip towards a distal end 452 a rake angle $\mu$, relative to the longitudinal axis of the shank 444, sufficiently large to kick the cut cement flowing over the inner surface 458 outwardly, away from the cut cement cylinder, to lessen the amount of cement fellow back into the cut cement trough. The rake angle $\mu$ preferably ranges between 15° and 75°, and more preferably equals about 45°.

The arcuate blade tip 446 preferably has a planing surface 459 having a radius less than the radius of the femoral canal to protect against the edges of the blade 446 digging into the cancellous bone adjacent to the cement. Preferably, the planing surface 459 has a radius less than 3.5 mm for use at the distal end of the femoral canal, and more preferably equals about 2.5 to 3 mm.

The planing surface 459 drafts from the cutting lip in the distal direction at a draft angle $\pi$ sufficiently small to reduce the tendency of the arcuate blade tip 446 from diving into the cancellous bone and sufficiently large to enable the cutting lip 457 to sink down to the cement/bone interface. Preferably the draft angle $\pi$ ranges between 5 and 25 degrees, and more preferably equals about 15 degrees.

The drafts on both sides of the cutting lip, i.e., the inclined inner surface 458 and the draft on the planing surface 459, minimizes the thermal footprint of the arcuate blade tip 446. As a result, the ultrasonic energy concentrates along the cutting lip 457 to facilitate the cutting action of the dual slitter 440.

The longitudinal section of the arcuate blade includes a recess 443 disposed adjacent to the longitudinal section 453 provide a relief for the cement kick up by the troughing section 456.

The surgeon may use the dual-slitter 440 to longitudinally severe a cement cylinder segment defined between the circumferential cuts made by the hoe 420. The surgeon settles the planing surface 459 of the arcuate blade tip 446 in the circumferential groove down to the cement/bone interface. Preferably, the cylinder at this point has a wall thickness equal to about 2 to 3 mm. The surgeon uses the dual slitter 440 in a retrograde manner, dragging the arcuate blade tip 446 along the cement/bone interface from distal to proximal at a rate of about 2 to 3 mm per second.

As the dual slitter 440 is drawn in the proximal direction, the cutting lips 457 on the longitudinal sides 455 cut generally parallel slots in the cement. The cutting lip 447 of the troughing section 456, disposed between the longitudinal sides 455, cuts the cement away from the bone. The cement flows between the longitudinal sides 455 and over the inner surface 458 which kicks the cement away from the cement cylinder to remove the severed cement from the cut trough. The surgeon subsequently removes the severed strip of cement from the femoral canal with forceps, tweezers or the like. Advantageously, the dual slitter 440 cuts a trough wide enough for the surgeon to locate the last cut by tactile feel or by visual inspection.

The surgeon may also use the single slitter 460 to longitudinally severe the cement cylinder. FIGS. 79-82 illustrate the single slitter 460 which comprises a connector 461, a shank 462 and a plow blade 463.

The shank 462 has a circular cross section at a proximal end 464 which smoothly tapers to a rectangular cross section at a base 465 of the plow blade 463. From the perspective illustrated in FIG. 81, the shank has a generally exponential shaped profile formed by a pair of surfaces 446 disposed on diametrically opposite sides of the shank 462. The generally exponential configuration of the shank 462 tailors the gain of the shank 462 to produce the desired stroke of approximately 0.0015 inch, peak-to-peak at 40 kHz, distributes the stress along the length of the tool to provide adequate mechanical strength, and provides symmetric ultrasonic wave propagation along the length of the shank 462. Preferably, a transition point 467 between the tapering cross-section and the proximal end 464 is located proximate to the antinode. In the most preferred embodiment, the shank 462 has a cross-sectional dimension equal to approximately 0.260 inch proximate to the proximal end 464 of the slitter 460 and tapers to 0.100 inch proximate to the base 465 of the blade 463.

As illustrated FIG. 80, the shank 462 also tapers in the transverse direction along the length of the shank 462 from the proximal end 464 to the blade 463. In the most preferred embodiment, the shank has width, measured in the transverse direction, proximate to the proximal end 464 of about 0.260 inch which linearly tapers to a width proximate to a distal end 467 of about 0.120 inch.

The plow blade 463 is formed on the distal end of the shank 462 to project in the transverse direction, as illustrated in FIG. 81, at an angle of approximately 90°. Preferably, the plow blade 463 smoothly blends into the shank to reduce the extent of whipping produced at a transverse end 468 of the plow blade 463. In other words, as viewed from the perspective illustrated in FIG. 81, the plow blade includes a curved back surface 469 having a radius blending into the back side of shank 470, and a fillet 471 blending the plow blade 463 into the shank 462. The configuration illustrated in FIG. 81 whips to a small extent when ultrasonically energized, which assists in the cutting action of the tool, but not to an extent causing the tool to mechanically fail.

The plow blade 463 includes a generally rule-shape cutting edge 472 extending along the length of the plow blade 463 on its proximal side. Sides 473 of the blade 463 taper outwardly from the cutting edge 472 to define a width between the sides 473 sufficient to provide adequate mechanical strength and to maintain a minimum thermal footprint. Preferably, the width of the plow blade 463 is as thin as possible to minimize the thermal footprint and concentrate the ultrasonic energy at along the narrow footprint of the plow blade. In the most preferred embodiment, the sides 473 of the plow blade 463 taper outwardly at about a 45° with respect to the longitudinal axis of the shank to a point defining a width of approximately 3 mm.

At the transverse end 468, as seen in FIG. 82, the plow blade 463 section includes a radius sized smaller than the radius of the femoral canal to prevent the edges to the slitter from scoring the cancellous bone at the cement/bone interface. Preferably, the radius is less than 0,250 inch, and more preferably equal to about 0.062 inch.

Referring to FIG. 81, the transverse end 468 of the plow blade 463, the plow blade 463 includes a curved distal surface 474 having a radius blending into a tip 475 to minimize the thermal footprint of the transverse end 468 in contact with the bone. In addition, the slight draft of the curved distal surface 474 helps the plow blade 463 sink into the cement, down to the cement/bone interface. In the most preferred embodiment, the distal surface 474 has a radius of about 0.140 inch.

The surgeon may use the single slitter 460 to longitudinally severe a cement cylinder segment defined between the circumferential cuts made by the hoe 420. The surgeon settles the tip 475 of the plow blade 463 in the circumferential groove down to the cement/bone interface. Preferably, the cylinder at this point has a wall thickness equal to about 2 to 3 mm. The surgeon uses the single slitter 460 in a retrograde manner, dragging the plow blade tip 475 along the cement/bone interface from distal to proximal at a rate of about 2 to 3 mm per second.

As the surgeon draws the single slitter 460 in the proximal direction, the cutting edge 472 along the plow blade 463 cuts the cement similar to a plow. The cement separates at the cutting edge 472 and flows over the sides 473 of the plow blade 463. On the distal side of the plow blade 463, some cement may reflow into the cut trough. Irrigation of the surgical site, however, reduces reflow because the irrigation fluid causes the cement to solidify quicker than air cooling alone.

By proceeding to divide up the cement cylinder in the forgoing manner, the surgeon produces a weakened structure which the surgeon can pry away from the surrounding cancellous bone. With a first longitudinal cut, the cylindrical section has been reduced, in structural terms, to a folded sheet having little mechanical strength. Subsequent longitudinal cuts, with either the dual slitter or the single slitter, section the folded layer of cement into segments which the surgeon can pry away from the cancellous bone using manual osteotomes. By repeating this procedure incrementally around the circumference of and down the length of the femoral canal, the surgeon can efficiently remove the entire cement cylinder without significantly damaging the surrounding tissue.

Having removed the femoral cement cylinder mantle, preferably as described above, the surgeon removes a cement or polyethylene plug at the distal end of the femoral canal. The surgeon may use any of the following tools and procedures to remove such plug.

FIGS. 83-87 illustrate a plug puller 480 comprising a connector 481, a shank 482 and a barbed tip 483. The elongated, cylindrical shank 482 preferably includes a step concentrator 484 (i.e., a step in its diameter) to tailor the gain of the barbed tool bit 480 to function optimally; i.e., to preferably stroke at approximately 0.001 to 0.004 inch, peak to peak, and more preferably at about 0.0015 inch, peak to peak at 40 kHz. The larger the transverse cross-sectional size of the barbed tip 483, the more gain needed for a fixed level power setting of the driving unit. In the most preferred embodiment, in which the barbed tip 483 has a transverse width of approximately 0.260 inch, it is preferred that the stepped concentrator 484 be located proximate to an antinode to minimize the gain realized and to reduce the mechanical stress at the conical concentrator 484.

In a most preferred embodiment, the shank 482 has a diameter at a proximal end 485 equal to about 0.260 inch and steps down to a diameter equal to about 0.150. Advantageously, the conical concentrator 484 includes a fillet 486 forming a transition between the smaller diameter and the cone to improve the mechanical strength of the shank 482, as known in the art.

The barbed tip 483 includes a generally arrow-shaped opposing pair of projections 487 positioned proximate to a distal end 488 of the barbed tip 483. The projections 487 ramp radially inwardly in the distal direction to converge into a sharp point 489 at the distal end 488 of the barbed tip 483. Preferably, an angle formed between a ramp surface 490 of the projection 487 and the longitudinal axis of the plug puller 480 is less than 45°, and more preferably is equal to about 30°.

The transverse width of each projection 487 has sufficient size to define a sufficiently large leverage surface 491 to facilitate the removal of the cement plug. The transverse width of the barbed tip 483, however, is preferably as small as possible to facilitate insertion into the narrow distal end of the femoral canal.

Preferably, the barbed tip 483 additionally includes a second opposing pair of arrow-shaped projections 492 disposed on the proximate side of the first pair of projections 487. The second pair of projections are preferably positioned at a sufficient distance from the leverage surfaces 491 of the first pair of projection 487 to prevent the barbed tip 483 from stripping out of the cement when retracted.

The barbed tip 483 includes the sharp point 489 at the distal end 488 to ease insertion of the plug puller 480 into the cement plug. In other words, the sharpened tip 489 allows the surgeon to mechanically position the tool bit tip 489 at a precise location before ultrasonically energizing the bit 480.

As illustrated in FIG. 83, the pairs of projections 487, 492 are positioned along a shaft 493 which extends from the tip 489 in the proximal direction along an axis generally aligned with the longitudinal of the shank 482. The shaft 493 preferably has a diameter sufficiently sized to provide adequate mechanical strength and to minimize the thermal footprint of the barbed tip 483 (i.e., the surface area of the tool in contact with the cement). In addition, the shaft 493 may have a smaller diameter than the shank 482 to increase the gain at the distal end of the tool in a manner similar to a stepped concentrator, as previously described.

On the proximal side of the projections 487, 492, the shaft includes fillets 494 to improve the mechanical strength of juncture between the projections 487, 492 and the shaft 493, as known in the art.

The barbed tip 483 preferably additionally includes a generally circular disk 495 circumscribing the distal end of the shank 482 and positioned between the distal end of the shank 482 and the shaft 493. The disk 495 provides the surgeon with tactile feel to indicate when the barb projections 487,492 have fully been inserted into the cement plug. Preferably, the disk 495 includes a pair of longitudinal notches 496 disposed at the circumferential edge of the disk 495 to provide pressure relief for fluid or cement on the distal side of the disk 495.

The surgeon, with the aid of ultrasonics, forces the barbed tip 483 into the cement plug positioned at the distal end of the femoral canal to a point completely embedding the barbed projections 487, 492. The surgeon can sense when the barbs 487, 492 have fully inserted as the disk 495 contacts on the plug. Where the disk 495 has a cross-sectional dimension generally equaling the diameter of the distal end of the femoral canal, fluid and cement on the distal side of the disk flow through the notches 496 to relieve the pressure on the distal side of the disk 495.

With the plug puller 480 still ultrasonically energized, the surgeon rotates plug puller 480 through an angle, such as 90°, to position virgin cement on the proximal side of the projections 487, 492. After de-energizing and letting the cement cool for approximately 10 to 15 seconds, the surgeon manually (i.e., without ultrasonics) extracts the cement plug out of the canal with the use of a slide hammer or like tool coupled to the proximal end 485 of the plug puller 480.

FIGS. 88-92 illustrates another embodiment of a disk drill 500, designed to extract cement from the cement plug located at the distal end of the femoral canal. The disk drill 500 comprises, a connector 501, an elongated shank 502, and a generally conical tip 503. The elongated, cylindrical shank 502 preferably includes at least one stepped concentrator 504 (i.e., a pronounced step in its diameter) to tailor the gain of the tool bit 500 to function optimally; i.e., to preferably stroke at approximately 0.001 to 0.004 inch, peak to peak, and more preferably at about 0.0015 inch, peak to peak at 40 kHz. The larger the size of the disk 503, the more gain needed for a fixed level power setting of the driving unit.

In one preferred embodiment, where the conical tip 503 has a diameter of about 0.500 inch, it is preferred that the stepped diameter 504 occur close to a node to increase the amount of gain achieved by the stepped configuration. In another preferred embodiment, the conical tip 503 has a diameter of approximately 0.375 inch and the step in the shank diameter occurs close to an antinode because this tool demands less gain to produce the desired stroke. The overall diameter of the conical tip 503 is limited by the diameter of the femoral canal proximate to the cement plug.

In a most preferred embodiment, the shank 502 has a diameter at the proximal end equal to about 0.260 inch and steps down to a diameter ranging between 0.075 and 0.150, and more preferably between approximately 0.100 and 0.125 inch. Advantageously, the shank 502 includes a fillet 505 forming a transition between the stepped diameters to improve the mechanical strength of the shank 502, as known in the art.

The length of the tool bit 500 also varies to tailor the gain of the tool bit 500 and tunes the tool bit for the same frequency as the rest of the tool bits.

Figure 88:
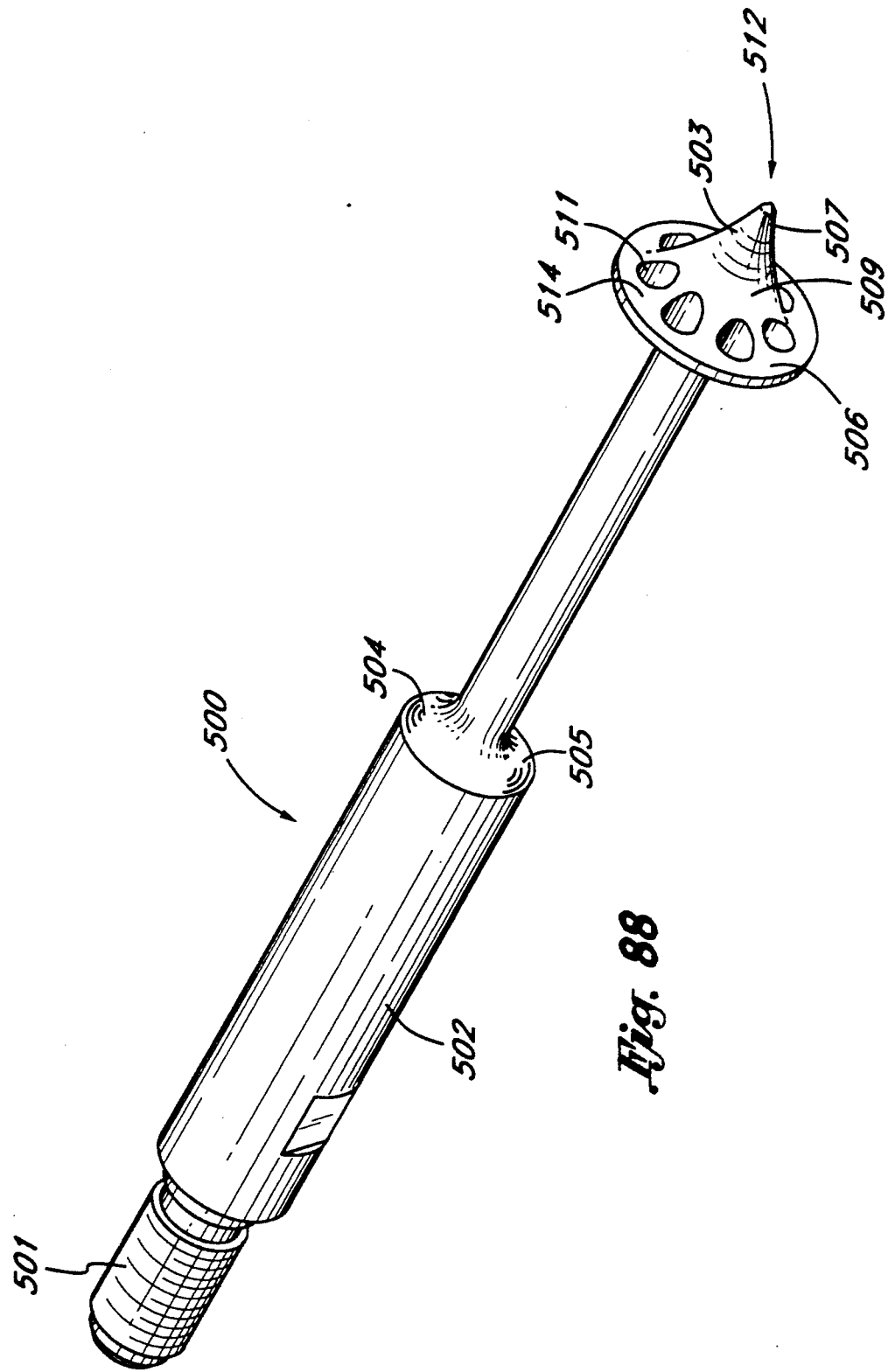
FIG. 88 is a perspective view of a disk drill of the present invention.

The conical tip 503 connects to the distal end of the shank 502, as illustrated in FIG. 88. The conical tip 503 tapers distally from a base 506 to a vertex 507. Preferably, as shown in FIG. 88, a surface 509 of the tip 503 has an arcuate taper from the base 506 to the vertex 507, with the arcuate taper having a radius of curvature.

A fillet 510 smoothly joins the surface of the shank 502 distal end with the base 506 proximal side.

The conical tip 503 includes a plurality of apertures 511 piercing through the tip base 506, the axis of each aperture 511 being generally parallel to the longitudinal axis of the tool. Although FIGS. 88 and 92 illustrate the apertures 511 as having a circular configuration, it is understood that other aperture configurations, such as, for example, a truncated conical section shape or a trapezoidal section shape, may be used as well. Preferably, the apertures 511 are sized and spaced about the conical tip 503 to minimize the surface area on the distal side 512 of the conical tip 503 without sacrificing the structural strength of the webbing 514 between each aperture 511 and the shank 502. More preferably, the apertures 511 are evenly spaced around a radius of the conical tip 503, maintaining approximately 0.030 inch between each aperture edge 513, between each aperture edge 513 and the circumferential edge of the conical tip 514, and between each aperture edge 513 and the diameter of the shank 502, as illustrated in FIG. 92. The number of apertures 511, therefore, preferably depends upon the diameter of the conical tip 503 and the above recited design requirements.

In one preferred embodiment, the conical tip 503 has a diameter of 0.500 inch, a shank 502 diameter proximate to the conical tip 503 equal to 0.125 inch, and five 0.125 inch diameter holes 511 spaced evenly about a 0.362 diameter circle, each spaced apart by 72°. In another preferred embodiment, the conical tip 503 has a diameter of 0.280 inch, a shank 502 diameter proximate to the conical tip 503 equal to 0.100 inch, and six 0.055 inch diameter holes 511 evenly spaced 60° apart about a 0.187 diameter circle. In a further preferred embodiment, the conical tip 503 has a diameter of 0.375 inch, a shank 502 diameter proximate to the conical tip 503 equal to 0.125 inch, and seven 0.067 inch diameter holes evenly spaced 51° apart about a 0.248 inch circle.

In use, the vertex 507 contacts a cement plug and melts the PMMA material immediately. Further travel in the distal direction causes the cement to flow around the tapered nose of the disk drill 500 and through the holes 511. Slight rocking rotation of the tool improves its effectiveness. Preferably, the tool is advanced distally for about an inch and then retracted from the femoral canal. The surgeon subsequently wipes off the extruded PMMA and repeats the process. A surgeon may also use the disk drill 500 to remove cement from the sides of the canal, especially when debulking, in either the normal proximal to distal direction or in the distal to proximal direction.

Figure 93:
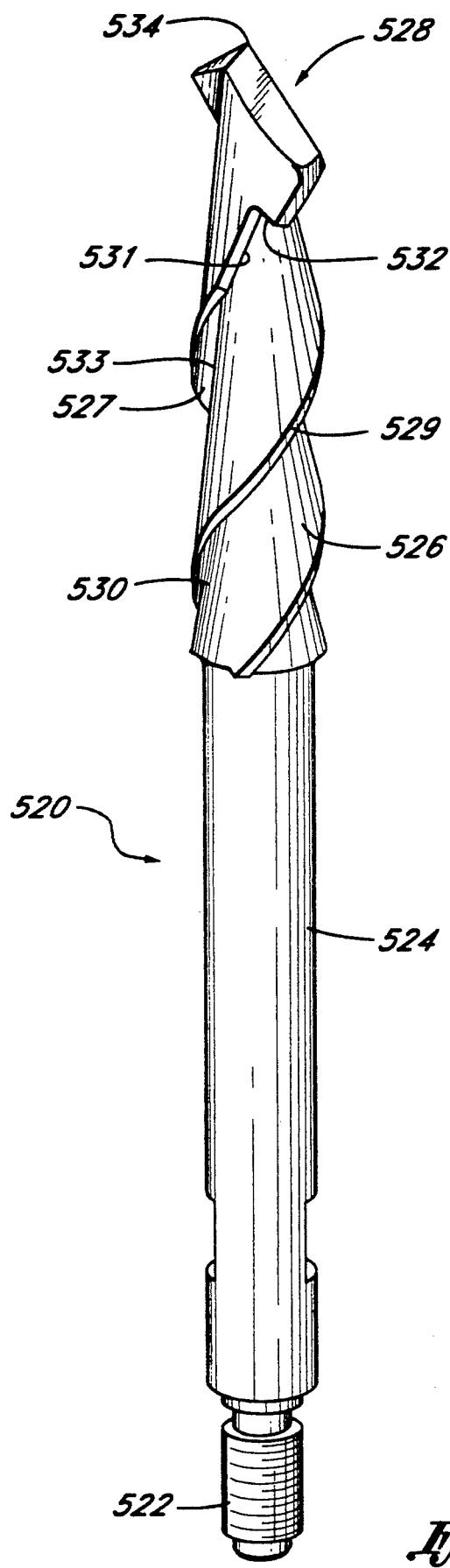
FIG. 93 is a perspective view of a push drill of the present invention.

A push drill 520, as illustrated in FIGS. 93-97, offers the surgeon the ability to use a single tool bit either as a plug puller or as a plug drill. FIG. 93 illustrates the push drill 520 comprising a connector 522, an elongated, cylindrical shank 524 and a drill tip 526.

Referring to FIG. 93, the drill tip 526 is formed on the distal end of the shank 524. The drill tip 526 has a parabolic flute 527 spiraling from a distal end 528 about the longitudinal axis of the push drill 520 in the proximal direction. The flute 527 has a length less than the length of a standard cement plug and preferably as short as possible to enable the direction of travel of the drill tip to change while drilling, as would be necessary when used with a cement plug having a curvature along its length. In the most preferred embodiment, the flute 527 has a length equal to about 1.00 inch.

The flute 527 has a sufficiently large rake angle (i.e., a helix angle) to permit pushing the drill tip 526 into the cement plug with a force of about 2 to 10 pounds applied in the distal direction. The rake angle preferably ranges between 20° and 70°, and more preferably ranges between about 30° and 60°. Within the preferred range of rake angles, it is further preferred that the flute 527 have a pitch P measured from the center line of one land 529 (i.e., the periphery portion of the drill body between the flute 527) to the center line of an adjacent land 529

(as shown in FIG. 95) within the range of from about 0.20 to 0.75 inch, and more preferably equal to about 0.45 inch.

The drill tip 526 has a transverse cross sectional dimension sized smaller than the interior diameter of the distal end of the femoral canal adjacent to the plug. Preferably, the drill tip 526 diameter is less than 1.00 inch, and more preferably equals either 0.750, 0.625, 0.500, 0.375, or 0.250 inch; the cross-sectional dimension being selected depending on the cross section dimension of the plug and the amount of cement that the surgeon wants to remove.

The drill tip 526 preferably includes a second parabolic flute 530 positioned about the longitudinal axis of the push drill 520 diametrically opposite the first parabolic flute 527. In the most preferred embodiment, the distance between a land 527 formed between the first flute 527 and second flute 530 and an adjacent land 527, likewise formed between the first flute 527 and the second flute 530, is equal to about 0.45 inch.

The drill tip 526 includes a pair of diametrically opposed notches 531 formed in the lands 529 on opposite sides of the drill tip 526. Each notch 531 generally has a "V" shape with a distal edge 532 cut generally perpendicular to a tangent of the land 529, as illustrated in FIG. 94. As a result, when the surgeon manually retracts (i.e., without ultrasonics) the push drill 520, the cement in the notch 531 behind the distal edge 532 squarely abuts against the distal edge 532 to improve the holding power of the drill tip 526 in the cement plug. The notch 531 preferably extends across the land 529 towards the axis of the drill tip 526 to a point adjacent a web 533 (i.e., the central portion of the drill tip 526 that joins the ends of the lands 529), to maximize the surface area of the distal edge 532.

The notches 531 are positioned on the drill tip 526 as close to the distal end 538 as possible to minimize the depth to which the drill tip 526 needs to be embedded for pulling out the cement plug, without significantly weakening the distal end 528 of the drill tip 526. Preferably, the notches 531 are located at least 0.125 inch from the distal end 528 of the drill tip 526 on its proximal side.

The push drill 528 includes a sharp tip 534 disposed at its distal end 528 defining a point angle Λ. Preferably, the point angle is sufficiently large to give the distal end 528 of the push drill 520 a low angle of attack to permit the surgeon to easily push the drill tip 526 through the cement plug. Preferably, the point angle Λ is larger than 45° and more preferably equal to about 60°.

In the most preferred embodiment, the shank 524 has a uniform cross sectional dimension equal to about 0.260 inch and a length of about 1.50 inch. The drill tip 526 has a cross-sectional area less than the shank 524, and thus the reduction in cross section produces a gain. Preferably, the drill tip 526 strokes at about 0.001 to 0.003 inch, and more preferably at about 0.0015 inch for a small cross sectional dimension drill tip 526 (e.g., 0.250 inch) and about 0.002 inch for a larger cross sectional dimension drill tip 526 (e.g., 0.750 inch).

In use, the surgeon forces the energized push drill 520 into the cement plug by applying a force of preferably about 5 pounds in the distal direction. As the distal end 528 of the drill tip 526 passes through the cement, the cement flows through the flutes 527, 530 and into the notches 531. The surgeon preferably embeds the drill tip 526 in the cement plug to a depth of about 0.50 inch.

When using the push drill 520 as a plug puller, the surgeon de-energizes the tool bit and waits approximately 10 seconds for the cement to solidify around the drill tip 526. The surgeon can subsequently extract the plug by using a slide hammer coupled to the proximal end of the push drill 520, as known in the art.

The surgeon may also use the push drill 520 to bore through the cement plug to produce a cement cylinder removable with the tools and procedures discussed supra. After embedding the drill tip 526 to a depth of about 0.50 inch, the surgeon de-energizes the push drill 420 and waits for about 5 seconds. The surgeon subsequently rotates the push drill 520 to break off the distal end of the cement helicals contained in the flutes 527, 530 of the drill tip 526 and retracts the push drill 520 in the proximal direction. The surgeon then wipes off the cement helicals from the drill tip 526 and repeats the procedure as required.

FIGS. 98-102 illustrates a trephine 540 comprising a connector 541, an elongated cylindrical shank 542, and a generally tubular head 543 having an opening 544 at its distal end.

Figure 98:
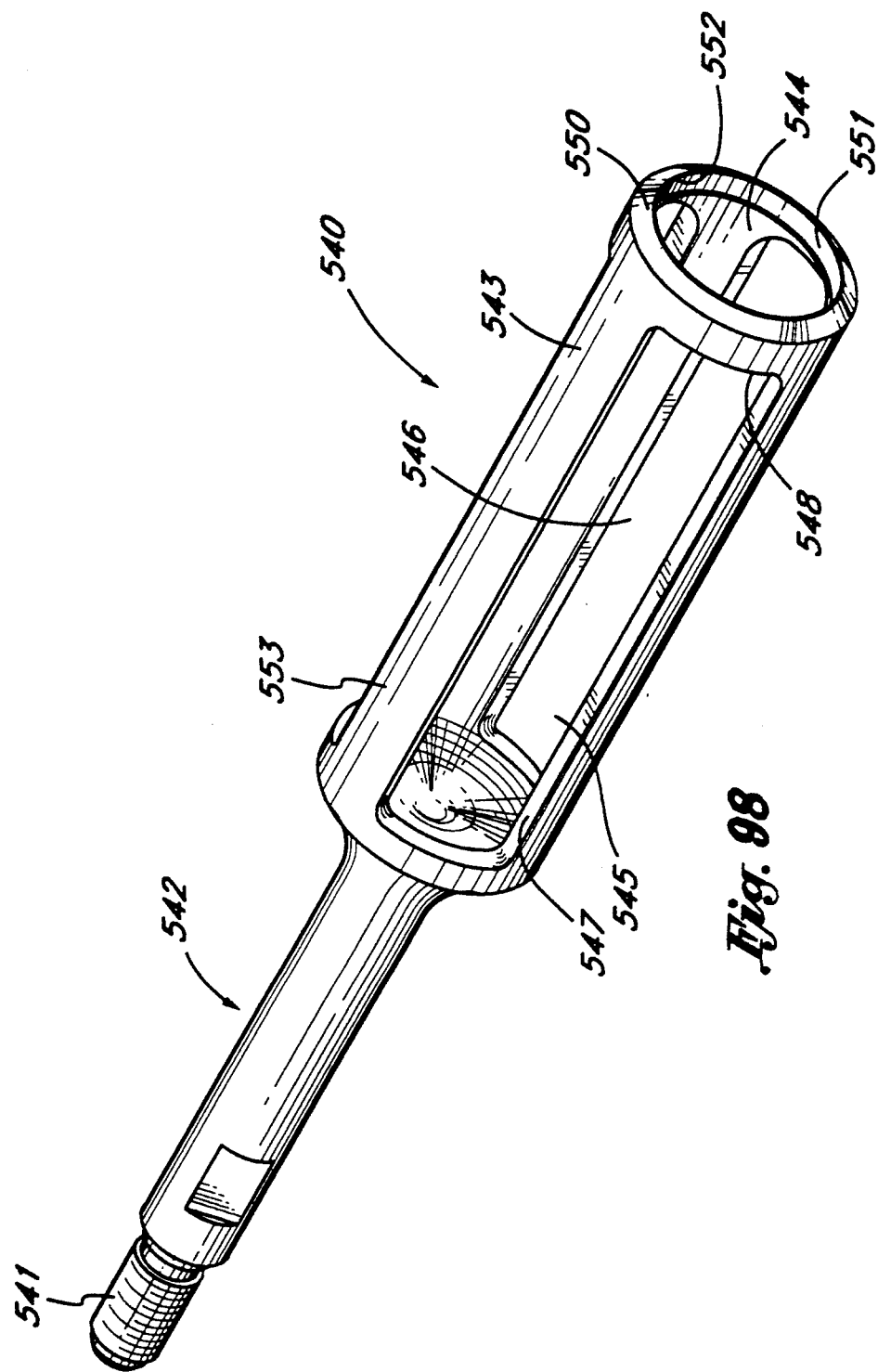
FIG. 98 is a perspective view of a trephine of the present invention.

As shown in FIG. 98, the shank 542 diverges radially outwardly into the hollow head 543. Preferably, the outer diameter of the head 543 has a size commensurate with the diameter of the distal end of the femoral canal.

The head 543 includes at least one generally rectangular window 545 opening into an interior cavity 546 of the head 543. The trephine 540 as shown in FIG. 93, preferably has three rectangular windows 545 to maximize visualization into the interior cavity of the head 543 during use. It is contemplated, however, that virtually any number and/or configuration of windows 545 can be used with lesser visualization.

Preferably, the windows 545 are symmetrically spaced about the circumference of the head 543 to ensure symmetrical propagation of ultrasound along the longitudinal axis of the tool.

For manufacturability purposes, the windows 543 may include a chamfer along edges 547 of the windows 543. An edge 548 on the distal side of the window 545, however, preferably is perpendicular to the longitudinal axis of the tool to form an abutment surface 549 between the cement and the tool thus providing leverage on the cement when retracting the tool to pull the cement out with the tool. The windows 545 provide a vent for the cement pushed into the tubular head 543 during use and facilitate the removal of the cement from the tubular head 543.

The walls of the tubular head 543 have a thickness, measured in the transverse direction, sufficient to resist flexure and withstand the stresses produced by the propagating ultrasound energy. At its distal end, the head 543 includes a chamfer 550 circumscribing an opening 544 and a counterbore 551 to form a sharp edge 552 at the distal end of the tool for knifing into a cement plug.

Although the transverse dimension of the trephine 540 increases distally, the cross-sectional area of the tool decreases to produce a desired ultrasonic gain. The position at which the shank 542 diverges into the head 543 is located proximate to a node to produce the desired gain.

The length of the head 543 is preferably dictated by the length of a nominal plug and the mechanical structural limitations imposed on struts 553 between the windows 545.

The surgeon uses the trephine 545 to core out the cement plug to form a cylinder which is subsequently removed with the other tool bits and procedures described above. The trephine 540 also allows the surgeon to work on the cement plug with a portion of another tool embedded in the plug, as would be the case, for example, if the plug puller 480 or disk drill 500 broke during use.

Figure 103:
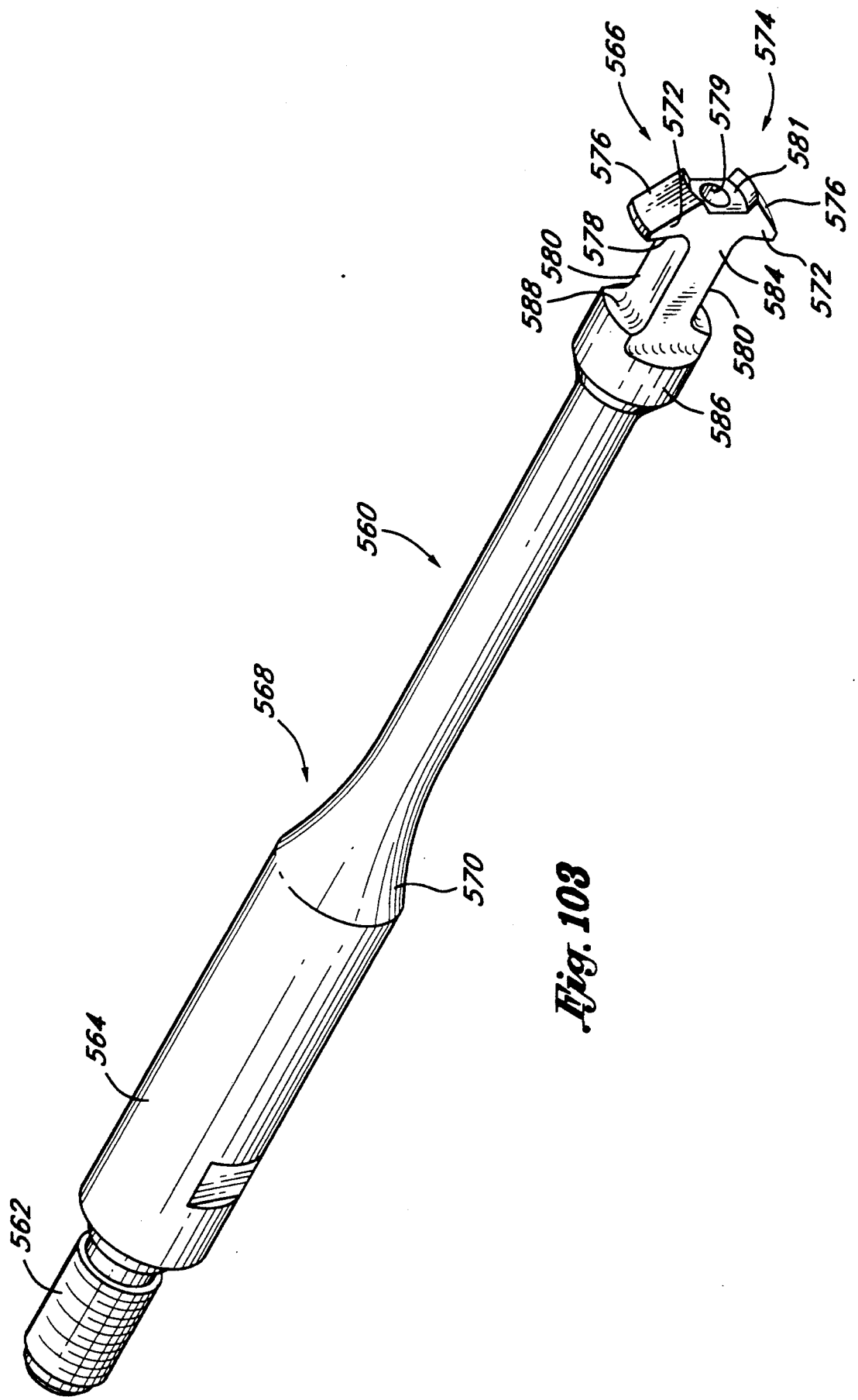
FIG. 103 is a perspective view of a poly-plug puller tool bit of the present invention.

FIGS. 103-110 illustrate a poly-plug puller 560 used to extract a polyethylene plug 561 (see FIGS. 108-110) of the type used to occlude the distal end of the femoral canal. As shown in FIG. 103, the poly-plug puller comprises a connector 562, a shank 564 and a barbed tip 566.

The elongated, cylindrical shank 564 preferably includes a conical concentrator 568 (i.e., a conical shaped change in its diameter) to tailor the gain of the poly-plug puller 560 to function optimally; i.e., to preferably stroke at approximately 0.001 to 0.004 inch, peak to peak, and more preferably at about 0.0015 inch, peak to peak at 40 kHz. In the most preferred embodiment, the conical concentrator 568 is located proximate to an antinode with the shank decreasing in cross section from 0.260 inch to 0.150 inch to minimize the gain realized and to reduce the mechanical stress at the conical concentrator 568. Advantageously, the conical concentrator 568 includes a fillet 570 forming a transition between the stepped diameters to improve the mechanical strength of the shank 564, as known in the art.

Referring to FIG. 104, the barbed tip 566 includes a generally arrow-shaped opposing pair of projections 572 positioned proximate to a distal end 574 of the barbed tip 566. The projections 572 ramp radially inwardly in the distal direction. Preferably, an angle formed between a ramp surface 576 of the projection 572 and the longitudinal axis of the poly-plug puller 560 is less than 60°, and more preferably is equal to about 45°.

Figure 110:
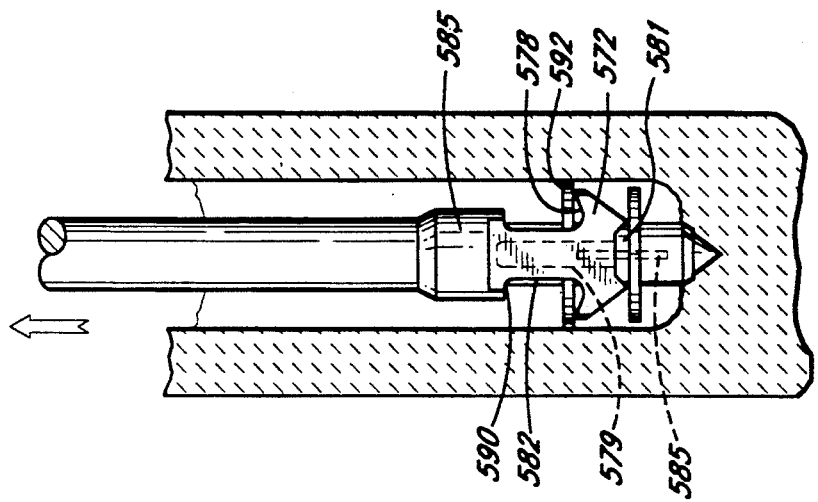
FIG. 110 is a partial cross-sectional view schematically illustrating the poly-plug puller tool bit of FIG. 103 in a position ready to extract the polyethylene plug from the femoral canal.

At its distal end 574, the barbed tip 566 includes an elongated cylindrical shaped aperture 579 extending along the longitudinal axis and opening onto generally concave section 581, as best seen in FIGS. 103 and 106. As shown in FIGS. 104 and 110, the concave section 581 includes a pair of sides 583 which slope in the proximal direction into the aperture 579 to channel a pin 585 of the polyethylene plug 561 into the aperture 579 as the barbed tip 566 passes through the plug 561. The aperture 579 has a sufficient size and length to receive the pin 585 during the removal process.

The transverse width of each projection 572 has sufficient size to define a sufficiently large leverage surface 578 to facilitate the removal of the polyethylene plug 561. The transverse width of the barbed tip 566, however, is preferably as small as possible to facilitate insertion into the narrow distal end of the femoral canal.

The leverage surfaces 578 preferably cant distally with respect to the longitudinal axis of the barbed tip 566 at an angle preferably greater than 5°, and more preferably equal to about 15°. The canted leverage surface 578 functions similar to a hook, biting into the polyethylene plug 561 when retracted.

As shown in FIG. 104, the barbed tip 566 includes a pair of diametrically opposed recesses 580 on the proximal side of the projections 572 to permit the flow of plastic behind the projections 572, thus improving the grip between the leverage surfaces 578 and the polyethylene plug 561. Between the recesses 580, the barbed tip 566 includes a shaft 584 having a cross section commensurate with a cylindrical segment 582 of the polyethylene plug 561. The commensurate fit between the cylindrical segment 582 and shaft 584 stabilizes the barb tip 566 relative to the polyethylene plug 561 which tends to facilitate a clean removal of the plug 561.

On the proximal side of the shaft 584, the barbed tip 566 includes a stop 586 having a cross section larger than the cylinder segment 582. The minimum distance between the leverage surfaces 578 and a distal side 588 of the stop 586 is greater than a distance between a proximal end 590 of the cylindrical segment 582 and the distal side of a plug disk 592, as illustrated in 110. Consequently, the stop 586 provides the surgeon with a tactile indication of when the projections 572 are positioned on the distal side of the plug disk 592.

Figure 109:
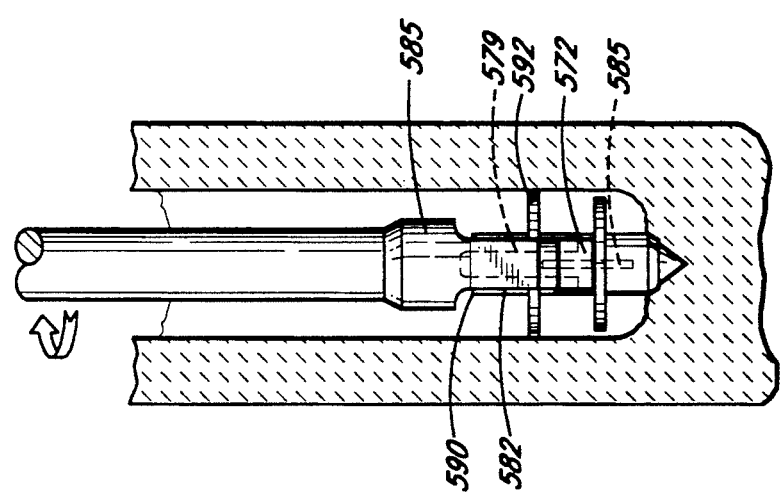
FIG. 109 is a partial cross-sectional view schematically illustrating the insertion of the poly-plug puller tool bit of FIG. 103 into the polyethylene plug.
Figure 108:
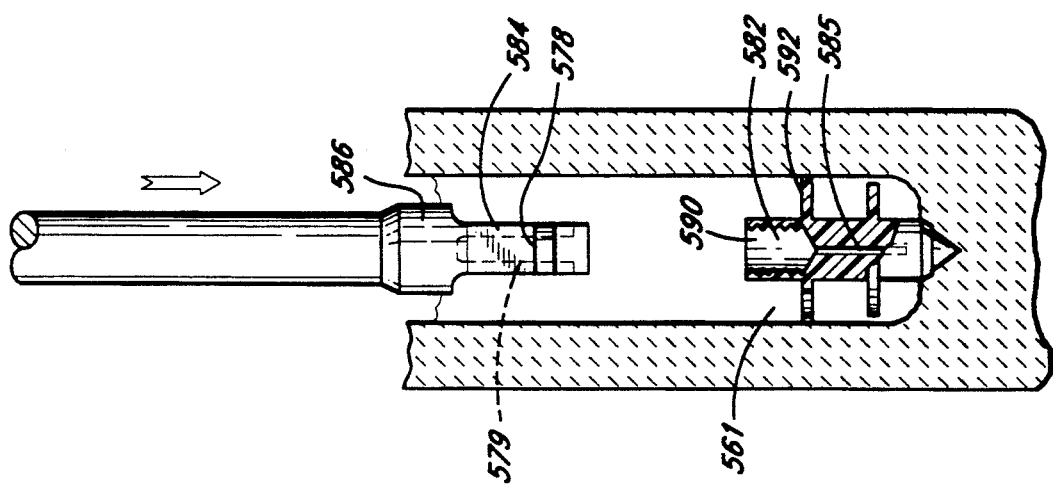
FIG. 108 is a partial cross-sectional view of a distal end of a femoral canal schematically illustrating a partial cross section of a polyethylene plug and a distal end of the poly-plug puller tool bit of FIG. 103.

In use, the ramp surfaces 576 of the barbed tip 566 engage the proximal end 590 of the cylindrical segment of the plug 561. As the surgeon applies a force distally, the projections 572 melt through the cylindrical segment wall 582 with the concave section 581 engaging the pin 585 and channeling it into the aperture 579, as schematically illustrated in FIG. 109. The barbed tip 566 passes through the plug 561 to a point where the stop 586 abuts the proximal end 590 of the cylindrical segment 582, as illustrated in FIG. 109. At this point, the projections 572 are positioned on the distal side of plug disk 592.

The surgeon subsequently rotates the barbed tip 566 through an angle, such as 90°, to position an unmelted portion of the disk 592 on the proximal side of the projections 572. As the barbed tip 566 rotates, plastic may flow into the recesses 580 adjacent to the leverage surfaces 572. The plastic is allowed to cool for about 15 seconds by interrupting the ultrasonic energy before the poly-plug puller 560 is retracted, either manually or with a slide hammer or the like, to remove the plug 561 from the femoral canal.

The ultrasonic energy conducting extender 46 will be understood by reference to FIGS. 5 and 6. The extender 46 enables the tool bit 44 to be spaced apart from the transducer 42 and acoustically couples the tool bit 44 to the transducer handpiece 42, as shown in FIG. 5. The length of the extender 46, like the tool bit 44, is influenced by the operating wavelength and by its intended use.

Preferably, the extender length coincides with the wavelength of the ultrasonic oscillation to position the handpiece/extender junction and the extender/tool junction at antinodes of the oscillation. More preferably, the length of the extender 46 equals 2.022 inches, 4.453 inches or 6.849 inches, plus or minus 20%, preferably plus or minus less than 10%, more preferably plus or minus less than 5% and most preferably plus or minus no more than about 1%.

It is also preferred that the extender 46 includes a stepped diameter with a large fillet 47, as shown in FIG. 6, to amplify the ultrasonic energy, as discussed above in the context of the tool diameter. However, for successive extenders, it is understood that extenders may be provided having a substantially uniform cross-sectional dimension throughout.

Figure 8:
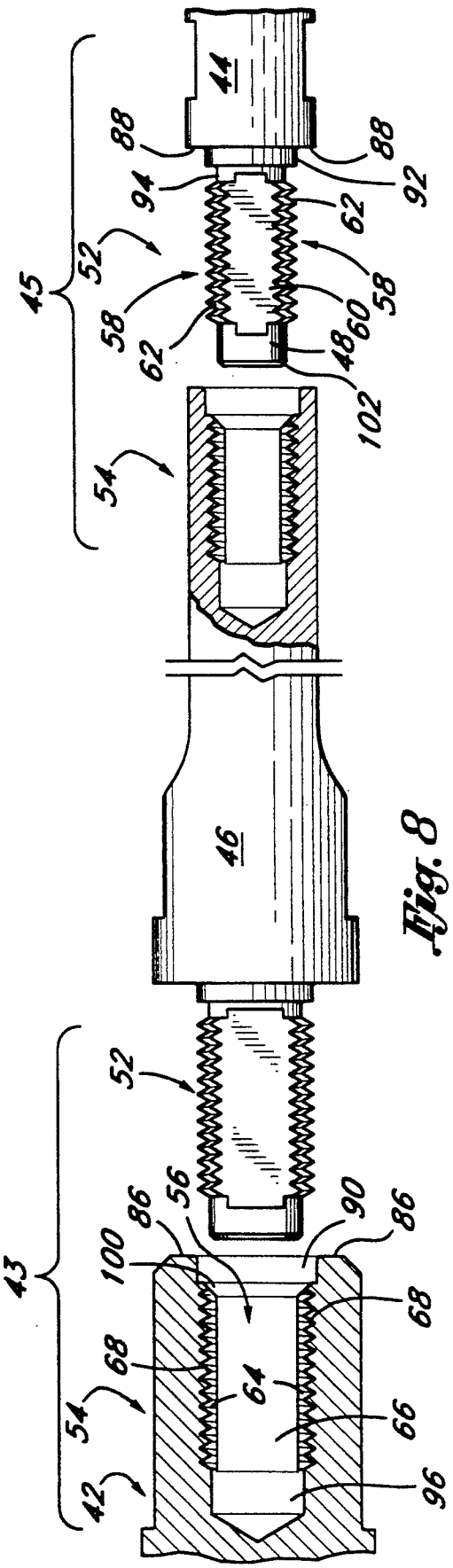
FIG. 8 is an exploded partial cross-sectional view of the junctions of FIG. 7.

Referring to FIG. 8, the tool bit 44 connects to the extender 46 via a second junction 45. Likewise, the extender 46 connects to the handpiece 42 via a first junction 43. It is contemplated that the structure of the first and second junctions 43, 45, apart from diameter, will be substantially identical, and the discussion herein of one will be understood as applying equally to both, unless specified to the contrary.

FIGS. 7-9 illustrate the junctions 43, 45 which comprise a generally cylindrical male component 52 and a tubular female component 54 comprising a generally cylindrical recess 56 adapted to receive the male component 52. These components quickly connect by inserting the male component 52 into the female component 54 and rotating one component with respect to the other component, preferably through a relatively short rotational arc, and optimally about ninety° plus or minus 10°.

When joined, the junction 43 produces a relatively high axial compression force, which is preferably uniformly distributed symmetrically about the contact surfaces between the two components to optimize the transfer of ultrasonic energy across the junction 43. Non uniform distribution of the axial compression force about the longitudinal axis of the junction 43 tends to decrease the efficiency of the transfer of energy across the junction 43, and can cause unwanted transverse motion (whipping) and may lead to premature mechanical failure.

Although FIGS. 6 through 12 illustrate the male component 52 extending in a proximal direction, it is understood that the relationship of the male and female components can be reversed.

Referring to FIGS. 8 and 9, the male component 52 comprises at least two axially extending splines 58 spaced apart by at least two axially extending flats 60. Preferably, the male component 52 comprises two diametrically opposed splines 58 and two diametrically opposed flats 60, alternatively positioned around the circumference of the component, as seen in FIG. 9.

Each spline 58 comprises a plurality of external threads 62 preferably configured in accordance with the American National Standard for Unified Threads ("UN"). It will be understood that other thread configurations, such as the American National Standard Acme Screw Threads ("Acme"), can be used as well. It has been found preferable, however, to employ the UN thread design instead of others, such as the Acme thread design, primarily for manufacturing ease.

Advantageously, the thread pitch and the pitch diameter of the threads 62 and the length of the splines 58 are selected to produce high axial compression between the components without structural failure. It is also preferable to select a generally standard thread for manufacturing convenience. Additionally, the threads must engage to produce high axial compression with little rotation. Preferably, circumferentially, 75% of the threads engage with rotation of no more than about 90° plus or minus 10°. For example, in one preferred embodiment the splines 58 comprise a series of 10-28 UNS-2A threads along a length of 0.315 inches, and in another embodiment, the splines 58 comprises a series of ¼-28 UNF-2A threads along a length of 0.435 inches. In general, the spline preferably comprises about 12 interrupted threads.

In general, the junction 43 has a minimum of 45° of total engagement between the spline threads to produce the high axial compression without mechanical failure. Preferably, the junction has an engagement between about 90-179° and most preferably about 173° (48% of 360°=172.8°). Thus, in a most preferred embodiment, the sum of the lengths of the threads 62 on the male component measured in a circumferential direction preferably range from 90° to 179°, and more preferably equal 173°.

The circumferential length of each spline thread 58 (i.e., the circumferential width of each spline) depends upon the number of splines 58 employed. For example, in a most preferred embodiment having two splines, the length of the thread 62 in a single spline along the circumferential direction range between 45° and 89.5°, and preferably equal 86.5°.

The female component 54 likewise comprises at least two axially extending splines 64 and at least two axially extending flats 66, disposed on the recess circumference 56 in a corresponding relationship with the flats and splines on the male component, as best seen in FIGS. 7, 12 and 13. Preferably, the female component 54 comprises two diametrically opposed splines 64 and two diametrically opposed flats 66 alternatively positioned around the circumference of the recess 56, as best seen in FIG. 12. Each spline 64 comprises a plurality of internal threads 68 configured to match and engage with the threads 62 on the male component 52.

As discussed above, the sum of the length of the threads 68 around the circumference of the recess 56 is preferably not less than about 90° and not greater than about 179°, and most preferably equal 173°. Each spline thread length depends upon the number of splines employed. For example, in a most preferred embodiment having two splines 64, the threads 68 of each spline 64 extend around the circumference of the recess 56 for at least approximately 45°, but less than approximately 89.5°, and preferably equal 86.5°.

The two splines 64 and two flats 66 alternately disposed on the interior circumference of the female component recess 56 provide an axial key-way 67 for receiving the two opposing splines 58 on the male component 52, as shown in FIG. 12. The male component 52 is inserted into the recess 56 of the female component 54 and rotated to interlock the corresponding splines on the male and female components, as shown in FIG. 13. It is desired that minimum rotation of one component with resect to the other component will produce a junction which achieves a relatively high efficiency of energy transmission therethrough.

In general, it has been found that a high compression across the junction symmetrically distributed about its longitudinal axis optimizes energy propagation. Preferably, the thread 62, 68 design of the junction 50 produces greater than about 300 pounds of axial compression force between the components with rotation of about 90°±10%. More preferably, a compression in excess of about 500 pounds will be achieved. Axial compressions of about 675 lbs. for a junction having an outside diameter of about 0.260 have been measured. Compressions in excess of about 1500 lbs. have been measured with an outside diameter of 7/16 inch, and in excess of about 2300 lbs. have been measured for diameters of 0.750 inches. As a result of higher compression, the ultrasonic pressure wave propagates across the junction with minimal energy loss.

It is preferred that the points of contact between the two joined surgical components be symmetric about the longitudinal axis of the male component 52 to uniformly distribute the compression force about the junction 43 in the radial direction. As a result, the ultrasonic oscillation maintains its propagation along the longitudinal axis of the joined surgical components without deflection from that axis. If deflection occurs, the tool will tend to whip resulting in undesired heat build-up and loss of energy at the tool tip 51.

In this regard, the female component 54 preferably additionally comprises an annular engagement surface 86 on the proximal end thereof which contacts a corresponding annular engagement surface 88 of the male component 52. Preferably, the engagement surface 86 of the female component 54 extends radially outwardly along a plane substantially perpendicular the axis of the internal recess 56, and the engagement surface 88 of the male component 52 extends radially outward along a plane substantially perpendicular to the axis of the male component 52. Referring to FIG. 7, as the splines 58, 64 interlock, the two components draw together to force the engagement surfaces 86, 88 against each other, resulting in an axial compression force across the junction 50.

Preferably, the engagement surfaces 86, 88 are smoothly polished to produce a substantially liquid-tight seal between the components as the surfaces abut. In addition to optimizing energy propagation, a liquid-tight seal reduces cavitation erosion of the components at the junction 50 and thereby extends the life of each component.

In a preferred embodiment, the female component 54 additionally comprises an axially extending, generally cylindrical counterbore 90 at the distal end of the recess 56 for receiving a generally cylindrical shank barrel 92 on the proximal end of the male component 52. The counterbore 90 and the shank barrel 92 are preferably centered with respect to the longitudinal axis of the male component 52. Preferably, the shank barrel 92 smoothly fits into the counterbore 90 to center the female component 54 with respect to the male component 52.

Advantageously, the male component 52 further comprises an undercut region 94 positioned between the engagement surface 88 and the spline 58 so that the spline threads 62 are fully formed (i.e., no run-out region). As a result, the splines 58 can be reduced in overall length, as will be understood in the art.

Referring to FIG. 8, the female component 54 preferably additionally includes a generally cylindrical pilot recess 96 for receiving a corresponding generally cylindrical tip barrel 98 at the proximal end of the male component 52. Preferably, the diameters of the pilot recess 96 and the tip barrel 98 substantially coincide with the minor diameter of the threads 62, 68. Advantageously, the pilot recess 96 and the tip barrel 98 are centered about the longitudinal axis of the male component 52 for optimizing the concentricity of the engagement surfaces 86, 88 between the components to optimize the longitudinal transfer of ultrasonic energy through the junction 43.

To facilitate rapid interconnection between the components, the female component 54 preferably additionally comprises an annular internal chamfer 100 and the male component 52 additionally comprises an annular tip chamfer 102. When the male component 52 is inserted into the female component 54, the chamfers 100, 102 ease the insertion by funneling the components together. Additionally, the edges of the leading spline threads 62 of the male component 52 preferably include a chamfer 104 to ease the engagement between the splines 58, 64 of the male component 52 and female component 54.

Referring to FIGS. 10 through 13, it is preferred that the surgical components include alignment arrows 106 etched on the exterior surface of the components to aid in the connection process. By aligning the arrows, the splines 58 of the male component 52 align with the key-way 67 of the female component 54, as seen in FIGS. 10 and 12. By rotating the components as shown in FIG. 11, the splines 58,64 of the two components interlock, as shown in FIG. 13. Flat opposing surfaces are provided on the exterior surface of all parts to receive a wrench to facilitate tightening and untightening of the junctions.

Those skilled in the art can manufacture the disclosed junction 43 by processes known in the art. For example, the generally cylindrical male component 52 and the shank barrel 92 thereto can be cut into an end of the shank of a surgical component, such as the extender 46 or the tool bit 46. The threads 62 can either be cold rolled onto the cylinder or preferably machine cut into the cylinder. The flats 64 can then be milled onto the component thereby interrupting the threads 62. Finally, the tip barrel 98 can be cut onto the distal end of the male component 52 such as by lathing operations well known in the art and the chamfers 102, 104 similarly added thereto.

The recess 56 of the female component 54 can be made by drilling the pilot hole recess 96 into the end of a surgical component. The counterbore 90 then can be milled and a portion of the pilot hole 96 tapped with the appropriate internal threads by processes known in the art. The flats 66 can be milled and broached into the recess 56 thereby interrupting the threads 68 on the recess 56 wall. Finally, the internal annular chamfer 100 can be drilled or milled to form a smooth transition from the counterbore 90 to the threaded recess 56.

The tool bits 44, 200, 220, 240, 260, 280, 300, 320, 340, 360, 380, 400, 420, 440, 460, 480, 500, 520, 540 and 560, and extenders 46 herein can be manufactured from any of a variety of materials known in the art. Preferably, high quality factor materials are used due to their known superiority in propagating ultrasonic energy. More preferably, a 400 series stainless steel or titanium is used because of their relative biocompatibility and their strength. Most preferably, a high grade titanium, such as Ti-6Al-4V alloy (aircraft grade 5), AA sonic inspected, is used.

An ultrasonic technique may also be employed for implanting an original or a replacement prosthesis during revision surgery. The preparation of a cavity in which a prosthesis is placed can be tedious and careful shaping of the cavity is important so that a tight fit is obtained. This is particularly significant for implantation of prostheses having porous surfaces for ingrowth of cancellous bone. At present such a cavity is formed by drilling and reaming to form a cavity of roughly the right shape and size and then finishing the cavity with a rasp or series of rasps complementary to the shape of the prosthesis, which are hammered or pressed into the medullary canal.

In practice of this invention at least the final reaming of the cavity is done by ultrasonically vibrating an object having the same shape as the prosthesis, with sufficient energy to disrupt cancellous bone, and pressing the ultrasonically vibrating object into the cancellous bone for forming a cavity complementary to the prosthesis. Preferably the object has rasp-like teeth which further aid in disrupting cancellous bone so that the object can be pressed into the cavity without excessive force which could fracture the cortex.

The object employed for forming a cavity in the cancellous bone complementary to the prosthesis may be a rasp that is inserted and temporarily left in place for testing and other procedures before the prosthesis is implanted. Preferably the object comprises the prosthesis itself. Thus, as illustrated in FIG. 4, a prosthesis 36 such as the femoral component of a hip joint has a plurality of rasp-like teeth on surface areas 37 on at least the tapering body portion of the prosthesis. An exemplary size for the rasp-like teeth is about 400 micrometers peak-to-peak. An ultrasonic transducer 38 is coupled to the self-holding taper 39 on the neck of the prosthesis as hereinabove described. As the prosthesis is ultrasonically vibrated by the transducer, it is pressed into the cavity and the teeth cut cancellous bone until the prosthesis fits tightly in the cavity. The transducer can then be removed and the prosthesis left in the cavity so formed.

It is not important that the scarf produced by the teeth on the prosthesis be removed from the cavity. On the contrary, it is not unusual to pack a portion of the cavity with fragments of cancellous bone and tissue removed in forming the cavity to assure a tight fit of the prosthesis. Such materials appear to promote growth of cancellous bone and may enhance fixation of a porous ingrowth prosthesis in the cavity. It is desirable to employ teeth with a spacing from about 50 to 400 micrometers since that is appropriate for ingrowth of cancellous bone. Thus, the newly grown cancellous bone between the teeth tends to secure the prosthesis in the cavity. In other words, the teeth are analogous to the porous surface on conventional ingrowth type prostheses.

Although limited embodiments have been described and illustrated herein, it will be readily appreciated by those skilled in the art that there may be many modifications and variations of practice of this invention. For example, although coupling the ultrasonic transducer to the self-holding taper on a prosthesis is particularly desirable, any of a variety of coupling means may be employed. As should already be apparent from the description, these techniques may be employed in combination with other conventional techniques for loosening and removing a prosthesis from a joint.

Further, although described in the context of a hip joint replacement, it will be apparent that similar techniques may be used with implants of shoulder joints, knees and the like, or with pins used for reinforcing bone. For example, ultrasonic vibrations may be used for implanting the keel of the tibial component of a knee joint. Ultrasonic vibration of a rasping object may be used for final shaping of the cavity for an acetabular cup. It is, therefore, to be understood that within the scope of the appended claims, this invention may be practiced otherwise then as specifically described.

It is claimed:

1. A medical apparatus, comprising:
an ultrasonic transducer; and
an ultrasonic energy-activated tool coupled to said ultrasonic transducer for conducting a medical procedure under ultrasonic energy, said tool comprising:
an operating tip on the distal end of the tool; and
a male connector component on the proximal end of said tool for coupling said tool to said ultrasonic transducer, said male connector component comprising:
a shank barrel configured to engage a correspondingly shaped recess defined by a female connector component; and
a stud member having a tip barrel and an interrupted threaded portion, said threads interrupted by a pair of diametrically opposed longitudinal flats, said threaded portion disposed between said shank barrel and said tip barrel, said tip barrel being configured to engage a correspondingly shaped recess defined by the female connector component, said shank barrel and said tip barrel being concentrically positioned about a longitudinal axis of said stud member to concentrically position the male connector component with the female connector component when engaged.

2. A medical apparatus, comprising:
an ultrasonic transducer; and
an ultrasonic energy-activated tool coupled to said ultrasonic transducer for conducting a medical procedure under ultrasonic energy, said tool comprising:
an operating tip on the distal end of the tool; and
a female connector component on the distal end of said tool for coupling said tool to said ultrasonic transducer, said female connector component comprising:
an engagement surface to abut a corresponding surface of a male connector component coupled to said ultrasonic transducer;
a recess having a threaded portion interrupted by a pair of diametrically opposed longitudinal flats; and
a counterbore configured to snugly receive a portion of said male connector component to concentrically position the male connector component with said female connector component when engaged, said counterbore being disposed between said engagement surface and said threaded portion.

3. The tool of claim 1 additionally comprising a shank connecting said distal operating tip to said connector, said shank and said operating tip having a combined longitudinal length equal to a multiple of half of a wave-length of said propagating ultrasonic energy within plus or minus 20 percent of said half of a wave-length.

4. The tool of claim 3 wherein said combined length of said shank and said operating tip generally equals a multiple of half of a wave-length of said propagating ultrasonic energy.

5. The tool of claim 1, wherein said operating tip comprises an operating surface extending radially and angled in the proximal direction.

6. The tool of claim 5, wherein said operating tip comprises an arrow-shaped projection, a portion of which forms said operating surface.

7. The tool of claim 1, wherein said operating tip comprises a leverage surface proximal of a distal end to provide leverage to remove material proximal of said leverage surface from said surgical site.

8. The tool of claim 7, wherein said leverage surface is generally normal to a longitudinal axis of said tool.

9. The tool of claim 1, wherein said tool has an overall cross-sectional dimension less than a cross-sectional dimension of a central canal of a bone at said surgical site.

10. The tool of claim 9, wherein said cross-sectional dimension of said tool is said to permit the concurrent insertion into said canal of aspiration and irrigation equipment.

11. The tool of claim 1, wherein said tool comprises a titanium alloy.

12. The tool of claim 1, wherein said titanium alloy is a high grade Ti-6Al-4V alloy (aircraft grade 5), AA sonic inspected.

13. The tool of claim 2, wherein said distal operating tip comprises a pair of opposing arrow-shaped projections which ramp radially inward in the distal direction and converge in a point.

14. A method of removing adhesive from a bone cavity, said adhesive of the type modified by ultrasonic energy, said method comprising the steps of:
  positioning an ultrasonic energy-activated tool in contact with adhesive in the bone cavity, said tool comprising a generally arrow-shaped projection having a leverage surface;
  energizing said tool with ultrasonic energy;
  embedding said projection of said tool in the adhesive;
  rotating said tool through an edge of less than 360° to position said leverage surface of said tool beneath unmodified adhesive;
  deenergizing said tool with said leverage surface positioned beneath unmodified adhesive;
  leveraging adhesive surrounding said tool from the cavity in the bone; and
  retracting said tool from said cavity to remove a portion of said adhesive.

15. The method of claim 14 wherein said tool is embedded in the adhesive while the tool is energized.

16. The method of claim 14 wherein said tool is rotated less than 180° to positioned said leverage surface beneath unmodified adhesive.

17. A method of removing material from an interior surface of a bone, said material of the type modifiable by ultrasonic energy, said method comprising the steps of:
  providing an ultrasonic energy-activated tool comprising a leverage surface;
  modifying a portion of the material with ultrasonic energy to provide a pathway for advancing said leverage surface through modified material;
  advancing said leverage surface of said tool through said pathway;
  rotating said tool to interlock said leverage surface beneath unmodified material proximal to said leverage surface; and
  retracting said tool from said interior surface to remove a portion of the material.

18. The tool of claim 1, wherein said operating tip comprises an axially extending body having a distal tip and a generally arrow-shaped lateral projection comprising a ramped surface inclined radially outwardly in the proximal direction and terminating at an intersection with a leverage surface, said leverage surface positioned between said intersection and said body, and being sized and positioned relative to a longitudinal axis of said tool so as to rotatably interlock beneath unmodified material proximal of said leverage surface.

19. The tool of claim 18, wherein an angle between said leverage surface and said longitudinal axis of said tool is between about 75° and about 135°.

20. The tool of claim 18, wherein said operating tip comprises a second generally arrow-shaped projection positioned on a side of said body generally opposite from that of said first projection.

21. The tool of claim 20, wherein said second projection is positioned directly opposite said first projection.

22. The method of claim 14, wherein said positioning step comprises positioning said ultrasonic energy-activated tool in contact with adhesive located at a distal end of a medullary canal.

23. The method of claim 22, wherein said medullary canal is formed in a femur.

24. The method of claim 14, additionally comprising the steps of:
  providing an ultrasonic energy transducer;
  connecting said ultrasonic energy-activated tool to said ultrasonic transducer by rotating said tool with respect to said transducer through an arc of less than about 180°; and
  producing an axial compressive force between said ultrasonic energy-activated tool and said ultrasonic transducer which is equal to or greater than about 300 pounds.

25. The method of claim 14, wherein said adhesive comprises poly methyl methacrylate.

26. The method of claim 14, wherein said step of energizing said tool with ultrasonic energy comprises:
  coupling said ultrasonic energy-activated tool to an ultrasonic transducer; and
  energizing said transducer to oscillate said tool within the range of from about 10 kHz to about 100 kHz.

27. The method of claim 14, wherein said step of energizing said tool with ultrasonic energy comprises oscillating said tool such that a distal end of said tool has a stroke length within the range of from about 0.001 to about 0.004 inches.

28. The method of claim 14, wherein said rotating step comprises rotating said leverage surface of said tool through an arc of less than 360 degrees.

29. The method of claim 17, wherein said step of modifying a portion of the material comprises the steps of:
  ultrasonically vibrating said tool; and
  contacting the material with said tool.

30. The method of claim 17, wherein said modifying step comprises the steps of:
  ultrasonically vibrating said tool; and
  contacting the material with said tool to modify the material.

31. The method of claim 30, wherein said step of vibrating said tool comprises the steps of:
  coupling said tool to an ultrasonic transducer; and
  energizing said ultraonic transducer.

* * * * *

UNITED STATES PATENT AND TRADEMARK OFFICE
CERTIFICATE OF CORRECTION

PATENT NO. : 5,318,570

DATED : June 7, 1994

INVENTOR(S) : Larry L. Hood et al.

It is certified that error appears in the above-indentified patent and that said Letters Patent is hereby corrected as shown below:

```
Column 42, line 61, replace "is said" with --is sized--.
Column 43, line 16, replace  "an edge" with --an angle--.
```

Signed and Sealed this

Seventh Day of February, 1995

Attest:

BRUCE LEHMAN

*Attesting Officer*     *Commissioner of Patents and Trademarks*